(12) United States Patent
Coats et al.

(10) Patent No.: US 7,652,005 B2
(45) Date of Patent: Jan. 26, 2010

(54) TRICYCLIC δ-OPIOID MODULATORS

(75) Inventors: Steve Coats, Quakertown, PA (US); Scott L. Dax, Landenberg, PA (US); Bart DeCorte, Southhampton, PA (US); Li Liu, Doylestown, PA (US); Mark McDonnell, Lansdale, PA (US); James J. McNally, Souderton, PA (US)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 12/248,150

(22) Filed: Oct. 9, 2008

(65) Prior Publication Data

US 2009/0042871 A1    Feb. 12, 2009

Related U.S. Application Data

(62) Division of application No. 11/313,635, filed on Dec. 21, 2005, now Pat. No. 7,439,239.

(60) Provisional application No. 60/638,315, filed on Dec. 22, 2004.

(51) Int. Cl.
C07D 471/08 (2006.01)
A61K 31/5415 (2006.01)
A61K 31/538 (2006.01)

(52) U.S. Cl. .................. 514/225.2; 544/42; 514/225.5

(58) Field of Classification Search .............. 544/42; 514/225.2, 225.5
See application file for complete search history.

(56) References Cited

U.S. PATENT DOCUMENTS

| | | | |
|---|---|---|---|
| 2,368,006 A | 1/1945 | Cusic | |
| 2,784,185 A | 3/1957 | Schuler | |
| 2,901,478 A | 8/1959 | Schuler | |
| 3,179,665 A | 4/1965 | Schmutz | |
| 3,305,547 A | 2/1967 | Stach et al. | |
| 3,470,188 A | 9/1969 | Kaiser et al. | |
| 3,557,287 A | 1/1971 | Berde et al. | |
| 3,931,232 A | 1/1976 | Bender et al. | |
| 3,987,042 A | 10/1976 | Gueremy et al. | |
| 4,086,350 A | 4/1978 | Zirkle | |
| 4,275,209 A | 6/1981 | Lassen et al. | |
| 4,356,184 A | 10/1982 | Deason et al. | |
| 4,666,907 A | 5/1987 | Fortin et al. | |
| 4,777,177 A | 10/1988 | Traber et al. | |
| 5,502,049 A | 3/1996 | Garret et al. | |
| 6,004,983 A | 12/1999 | Andersen et al. | |
| 6,114,354 A | 9/2000 | Andersen et al. | |
| 6,153,626 A | 11/2000 | Pelcman et al. | |
| 7,060,711 B2 | 6/2006 | Lubbert et al. | |
| 7,432,257 B2 | 10/2008 | Coats et al. | |
| 7,439,239 B2 | 10/2008 | Coats et al. | |
| 7,553,850 B2 | 6/2009 | Dax et al. | |
| 2003/0018447 A1 | 1/2003 | Florschuetz | |
| 2003/0166672 A1 | 9/2003 | Lubbert et al. | |
| 2005/0009860 A1 | 1/2005 | Carson et al. | |
| 2006/0030585 A1 | 2/2006 | Dax et al. | |
| 2006/0135522 A1 | 6/2006 | Carson et al. | |
| 2006/0135524 A1 | 6/2006 | Carson et al. | |
| 2006/0135763 A1 | 6/2006 | Coats et al. | |
| 2006/0148823 A1 | 7/2006 | Coats et al. | |
| 2006/0287297 A1 | 12/2006 | DeCorte et al. | |
| 2008/0306111 A1 | 12/2008 | Carson et al. | |
| 2008/0318937 A1 | 12/2008 | Coats et al. | |
| 2009/0042871 A1 | 2/2009 | Coats et al. | |

FOREIGN PATENT DOCUMENTS

| | | |
|---|---|---|
| DE | 2009555 | 10/1970 |
| EP | 0005607 B1 | 11/1979 |
| EP | 1049676 B1 | 11/2000 |
| EP | 1306376 A1 | 5/2003 |
| EP | 1321169 A1 | 6/2003 |
| FR | 2290202 A1 | 6/1976 |
| GB | 1128734 | 7/1966 |
| WO | WO9828275 A1 | 7/1998 |
| WO | WO9900376 A1 | 1/1999 |
| WO | WO0146191 A1 | 6/2001 |
| WO | WO0166543 A2 | 9/2001 |
| WO | WO0172303 A1 | 10/2001 |
| WO | WO0236573 A2 | 5/2002 |
| WO | WO0248122 A2 | 6/2002 |
| WO | WO03035646 A2 | 5/2003 |
| WO | WO04026030 A2 | 4/2004 |
| WO | WO04035541 A1 | 4/2004 |
| WO | WO04092165 A1 | 10/2004 |
| WO | WO05003131 A1 | 1/2005 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Ananthan, S.: The AAPS Journal 2006, 8(1): E118-E125.
Berge, S.M. et al.: Pharmaceutical Salts; J. Of Pharmaceutical Sciences (1977) 66(1): 1-19.
Bidlack, J.M. et al.: 8-Carboxamidocyclazocine: A Long-Acting, Novel Benzomorphan; The J. of Pharm. & Exper. Therapeutics (2002) 302(1): 374-380.

(Continued)

Primary Examiner—Kahsay T Habte

(57) ABSTRACT

The invention is directed to delta opioid receptor modulators. More specifically, the invention relates to tricyclic δ-opioid modulators. Pharmaceutical and veterinary compositions and methods of treating mild to severe pain and various diseases using compounds of the invention are also described.

81 Claims, No Drawings

OTHER PUBLICATIONS

Biemans et al.: Journal of Organic Chemistry, 1996, 61:9012-9015.
Boyd, R.E. et al.: Synthesis and Binding Affinities of 4-Diarylaminotropanes, a New Class of Delta Opioid Agonists; Bioorg. & Med. Chem. Letters (2000) 10: 1109-1111.
Calderon, S.N. et al: "SNC 80 and Related Opioid Agonists", Current Pharmaceutical Design, 2004 10:733-742.
Calo, et al.: British Journal of Pharmacology 2002, 136:303-311.
Carson, J.R. et al., N-Alkyl-4[(8-azabicyclo[3.2.1]-oct-3-ylidene)phenylmethyl]- benzamides, μ and δ opioid agonists: a μ address; Bioorganic & Med. Chem. Letters (2004) 14:2113-2116.
Catalog Frontier Scientific, Logan, UT. (online hppt://www.frontiersci.com/browse.php?browse=Boronic%20acid Apr. 2, 2007).
Chang et al.: Molecular Pharmacology, 1984, 26:484-488.
Commercial 2-Bromo-Phenols from Sigma-Aldrich.
Commercial 4-piperidinones.
Connor, M. et al.: Opioid Receptor Signalling Mechanisms; Clinical and Exper. Pharmacology and Physiology (1999) 26: 493-499.
Dorwald, F.Z.: Side Reactions in Organic Synthesis (2005) Wiley: VCH, Weinheim p. 1X of Preface: 1-15.
Dörwald, F.Z.: Side Reactions in Organic Synthesis (2005) Wiley: VCH, Weinheim p. 1X of Preface & Chapter 8: 279-308.
Erchegyi et al.: Journal of Medicinal Chemistry, 2003, 46:5587-5596.
Frontier Scientific (Logan, UT) Commercial Boronic Acids (Provided by the Examiner).
Furness, M.S. et al.: Probes and Narcotic Receptor-Mediated Phenomena. 27.[1] Synthesis and Pharmacological Evaluation of Selective δ-Opioid Receptor Agonists from 4-[αR?)-α(2S,5R)-4- Sub stituted-2,5-demethyl-1-piperazinyl-3            -methoxybenzyl-]-N,N-diethylbenzamides and Their Enantiomers; J. Med. Chem. (2000) 43:3193-3196.
Gilbert, P.E. et al.: The Effects of Morphine- and Nalorphine-Like Drugs in the Nondependent, Morphine-Dependent and Cyclazocine-Dependent Chronic Spinal Dog; The J. Of Pharm. And Exp. Thera. (1976) 198(1): 66-82.
Gould, P.L.: Salt selection for basic drugs; Intl J. of Pharmaceutics (1986) 33: 201-217.
Gribble, G.W. et al.: Sodium Triacetoxyborohydride[1]; Encyclopedia of Reagents for Organic Synthesis online @ http://www.mrw.interscience.wilev.com/eros/articles/rs112/sect0.html Apr. 24, 2007.
Gross, R.A. et al.: Dynorphin A and cAMP-dependent protein kinase independently regulate neuronal calcium currents; Proc. Natl. Acad. Sci. (1990) 87: 7025-7029.
Hancock, B.C. et al.: Characteristics and Significance of the Amorphous State in Pharmaceutical Systems; J. of Pharm. Sciences (1997) 86(1): 1-12.
Hutchins, R.O. et al.: Selective Reductive Displacement of Alkyl Halides and Sulfonate Esters with Cyanoborohydride Reagents in Hexamethylphosphoramide; J. Org. Chem. (1977) 42(1): 82-91.
Jones, M. Jr.: Organic Chemistry Norton, New York (1997):578-591.
Kaiser, C. et al,: "Analogs of Phenothiazines. 5. Synthsis and Neuropharmacological Activity of Some Piperidylidene Derivatives of Thioxanthenes, Xanthenes, Dibenzoxepins, and Acridans." J. Med. Chem., 1974:57-61, vol. 17, No. 1.
Kenakin, T. et al.: The ligand paradox between affinity and efficacy: can you be there and not make a difference?; Trends in Pharm. Sciences (2002) 23(6): 275-280.
Kruzsynski et al.: Journal of Peptide Research, 2005, 66:125-131.
Le Bars, D. et al.: Animal Models of Nociception; Pharmacological Reviews (2001) 53: 597-652.
Lord, John a.H. et al.: Endogenous opioid peptides: multiple agonists and receptors; Nature (1977) 267: 495-499.
Loughhead, David G.: "Unusual Reductions Induced by Formic Acid";Tetrahedron Letters, 1998, 5701-5702.
Mansour, A. et al.: Anatomy of CNS opioid receptors; Trends in Neuroscience (1988) 11(7): 308-314.
Nieschulz, O. et al.: "Pharmacological studies on 10-(1-methyl-3-piperidyl)-2 methoxyphenothiazine and related compounds"; Arzneimittel-Forschung 1960, 10, 156-165.

Pert, C.B. et al.: Opiate Receptor: Demonstration in Nervous Tissue; Science (1973) 179: 1011-1014.
Pozharskii et al.: Molecular Rings Studded With Jewels; Heterocycles in Life and Society, Wiley, 1997, pp. 1-6.
Quock, R.M. et al.: The δ-Opioid Receptor: Molecular Pharmacology, Signal Transduction, and the Determination of Drug Efficacy; Pharmacological Reviews (1999) 51(3): 503-532.
Sharma, S.K. et al.: Dual regulation of adenylate cyclase accounts for narcotic dependence and tolerance; Proc. Natl. Acad. Sci. (1975) 72(8): 3092-3096.
Still, W. Clark et al.: Rapid Chromatographic Technique for Preparative Separations with Moderate Resolution; J. Org. Chem. (1978) 43(14): 2923-2925.
Structures in copending U.S. Appl. No. 11/195,231.
Sun, X. et al.: Synthesis and Opioid Receptor Binding Properties of Conformation-Rigidified Analogues of 8-Carboxamidocyclazocine and 8-Formamidocyclazocine; Abstract of Papers 229th ACS Natl Meeting NY 2005.
Tao, et al.: Synthesis and structure-activity relationships of novel poly(ADP-ribose) polymerase-1 inhibitors; Bioorganic & Medicinal Chemistry Letters, 2006, 16:938-942.
Thomas, J.B. et al.: 4-[(8-Alkyl-8-azabicyclo [3.2.1] octy1-3 -y1)-3 -arylanilino]-N,N- diethylbenzamides: High Affinity, Selective Ligands for the Delta Opioid Receptor Illustrate Factors Important to Antagonist Activity; Bioorg. & Med. Chem. Letters (2000) 10(11): 1281-1284.
Thomas, J.B. et al.: (±)-4-[(N-Allyl-CIS-3-Methyl-4-Piperidinyl)Phenylamino]-N,N-Diethylbenzamide Displays Selective Binding for the Delta Opioid Receptor; Bioorg. & Med. Chem. Letters (1999) 9(20): 3053-3056.
Thomas, J.B. et al.: Factors Influencing Agonist Potency and Selectivity for the Opioid δ Receptor Are Revealed in Structure -- Activity Relationship Studies of the 4-[(N-Substituted-4-piperidinyl)arylamino]-N,N-diethylbenzamides; J. Med. Chem. (2001) 44(6): 972-987.
Truce, W. E. et al.: The Smiles and Related Rearrangements of Aromatic Systems; Organic Reactions (1970) 18: 99-215.
Van Alstine, M.A. et al.: Synthesis and evaluation of novel N-substituted derivatives of 8-carboxamidocyclazocine; Abstract of Papers 231st ACS National Meeting, Atlanta, GA 2006, MEDI-009.
Walpole, C.S.J. et al.: The Discovery of Capsazepine, the First Competitive Antagonist of the Sensory Neuron Excitants Capsaicin and Resiniferatoxin; J. Med. Chem. (1994) 37: 1942-1954.
Wentland, M.P. et al.: 8-Aminocyclazocine Analogues: Synthesis and Structure--Activity Relationships[†]; Bioorg. & Med. Chem. Letters (2000) 10(2): 183-187.
Wentland, M.P. et al.: Selective Protection and Functionalization of Morphine: Synthesis and Opioid Receptor Binding Properties of 3-Amino-3-desoxymorphine Derivatives[†,1,] ; J. Med. Chem. (2000) 43(19): 3558-3565.
Wentland, M.P. et al.: 3-Carboxamido Analogues of Morphine and Naltrexone: Synthesis and Opioid Receptor Binding Properties; Bioorg. & Med. Chem. Letters (2001) 11: 1717-1721.
Wentland, M.P. et al.: 8-Carboxamidocyclazocine Analogues: Redefining the Structure--Activity Relationships of 2,6-Methano-3-benzazocines; Bioorg. & Med. Chem. Letters (2001) 11: 623-626.
Wentland, M.P. et al.: Syntheses and Opioid Receptor Binding Affinities of 8-Amino-2,6-methano-3-benzazocines; J. Med. Chem. (2003) 46: 838-849.
Wentland, M.P. et al.: Redefining the Structure--Activity Relationships of 2,6-Methano-3-benzazocines. Part 2: 8-Formamidocyclazocine Analogues; Bioorg. & Med. Chem. Letters (2003) 13: 1911-1914.
Wentland, M.P. et al.: Thioformamido and Thiocarboxamido Derivatives of Cyclazocine: Syntheses and Opioid Receptor Binding Properties; Abstract of Papers 226th ACS Natl. Meeting NY 2003.
Wentland, M.P. et al.: Redefining the structure--activity relationships of 2,6-methano-3- benzazocines. Part 3: 8-Thiocarboxamido and 8-thioformamido derivatives of cyclazocine; Bioorg. & Med. Chem. Letters (2005) 15: 2547-2551.
Wentland, M.P. et al.: Synthesis and opioid receptor binding properties of a highly potent 4-hydroxy analogue of naltrexone; Bioorg. & Med. Chem. Letters (2005) 15: 2107- 2110.

West, A.R.: Solid State Chemistry and its Applications, Wiley, New York, 1988, pp. 358 & 365.

Wollemann, M.: Recent Developments in the Research of Opioid Receptor Subtype Molecular Characterization; J. of Neurochemistry (1990) 54(4): 1095-1101.

Zhang, A. et al.: 10-Ketomorphinan and 3-Substituted-3-desoxymorphinan Analogues as Mixed κ and μ Opioid Ligands: Synthesis and Biological Evaluation of Their Binding Affinity at Opioid Receptors; J. Med. Chem. (2004) 47(1):165-174.

Zhang X. et al.: "Probes for Narcotic Receptor Mediated Phenomena. 26[1-3] Synthesis and Biological Evaluation of Diarylmetylpiperazines and Diarylmethylpiperidines as Novel, Nonpeptidic δ Opioid Receptor Ligands", Journal of Medicinal Chemistry, 1999, 42:5455-5463.

PCT International Search Report, PCT/US2005/046693, Jun. 26, 2006, which relates to U.S. Appl. No. 11/313,635.

* cited by examiner

TRICYCLIC δ-OPIOID MODULATORS

CROSS-REFERENCE TO RELATED APPLICATIONS

This application is a divisional of application Ser. No. 11/313,635 filed Dec. 21, 2005, now U.S. Pat. No. 7,439,239, which in turn claims the benefit of U.S. provisional application Serial No. 60/638,315, filed December 22, 2004. The complete disclosures of the aforementioned related U.S. patent applications are hereby incorporated herein by reference for all purposes.

STATEMENT REGARDING FEDERALLY SPONSORED RESEARCH OR DEVELOPMENT

The research and development of the invention described below was not federally sponsored.

BACKGROUND

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

D. Delorme, E. Roberts and Z. Wei, World Patent WO/28275 (1998) discloses diaryl methylidenylpiperidines that are opioid analgesics, but does not disclose or suggest the compounds of the present invention.

C. Kaiser, and others (J. Med. Chem. 1974, Volume 17, pages 57-61) disclose some piperidylidene derivatives of thioxanthenes, xanthenes, dibenoxepins and acridans that are neuroleptic agents. These authors, however, do not disclose or suggest either the structure or the activity of the compounds of the present invention.

British Patent GB 1128734 (1966) discloses derivatives of 6,11-dihydrodibenzo[b,e]oxepine that are anticholinergic, anti-convulsive, muscle-relaxing, sedating, diuretic, and/or vasoactive agents. These, agents, however, differ significantly from the compounds of the present invention both structurally and pharmacologically.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

SUMMARY

The present invention is directed, inter alia, to compounds of Formula (I) and compositions comprising a compound of Formula (I):

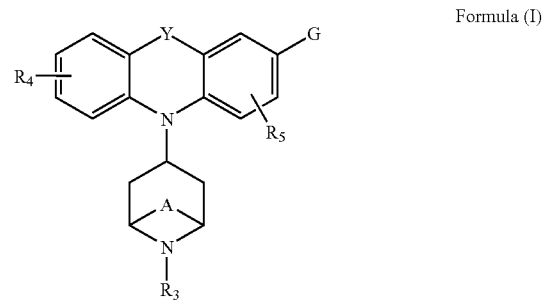

Formula (I)

wherein:

G is —C(Z)N($R_1$)$R_2$, $C_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

$R_1$ is a substituent selected from the group consisting of hydrogen, $C_{1-8}$alkanyl, $C_{2-8}$alkenyl, and $C_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —($CH_2$)$_{3-5}$—, —O($CH_2$)$_{2-4}$—, —($CH_2$)$_{2-4}$O—, and —O($CH_2$)$_{1-3}$O—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein $C_{6-10}$aryl is optionally substituted with one to three substituents independently selected from the group consisting of $C_{1-6}$alkanyl, $C_{1-6}$alkoxy, halogen, and hydroxyl; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl and fluoroalkanyloxy; or optionally, when $R_4$ is two substituents attached to adjacent carbon atoms, the two substituents together form a single fused moiety; wherein the fused moiety is —($CH_2$)$_{3-5}$—, —O($CH_2$)$_{2-4}$—, —($CH_2$)$_{2-4}$O—, —O($CH_2$)$_{1-3}$O—, or —S—C($NH_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —($CH_2$)$_m$—, wherein m is 2 or 3;

Y is O or S;

Z is O, S, NH, N($C_{1-6}$alkanyl), N(OH), N(O$C_{1-6}$alkanyl), or N(phenyl);

and enantiomers, diastereomers, tautomers, solvates, or pharmaceutically acceptable salts thereof.

The present invention is also directed to, inter alia, veterinary and pharmaceutical compositions containing compounds of Formula (I) wherein the compositions are used to treat mild to severe pain in warm-blooded animals.

DETAILED DESCRIPTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1- en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$)alkyl, with ($C_1$-$C_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or ($C_1$-$C_6$)alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_{5-20}$) aryl, with ($C_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. [In preferred embodiments, the arylalkyl group is ($C_{6-26}$) arylalkyl, e.g., the alkanyl, alkenyl or alkynyl moiety of the arylalkyl group is ($C_{1-6}$) and the aryl moiety is ($C_{5-20}$). In particularly preferred embodiments the arylalkyl group is ($C_{6-13}$), e.g., the alkanyl, alkenyl or alkynyl moiety of the arylalkyl group is ($C_{1-3}$) and the aryl moiety is ($C_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy ($CH_3CH_2CH_2O$—), propan-2-yloxy (($CH_3$)$_2$CHO—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are ($C_{1-8}$) alkanyloxy groups, with ($C_{1-3}$) being particularly preferred.

"Parent Heteroaromatic Ring System:" refers to a parent aromatic ring system in which one carbon atom is replaced with a heteroatom. Heteratoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkanyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O⁻, =O, —OR, O—OR, —SR, —S—, =S, —NRR, =NR, —CX₃, —CN, —OCN, —SCN, —NCO, —NCS, —NO, —NO₂, =N₂, —N₃, —NHOH, —S(O)₂O⁻, —S(O)₂OH, —S(O)₂R, —P(O)(O⁻)₂, —P(O)(OH)₂, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, $(C_{1-8}$alkylamino)carbonyl, (arylamino)carbonyl and aryl($C_{1-8}$alkyl)carbonyl.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

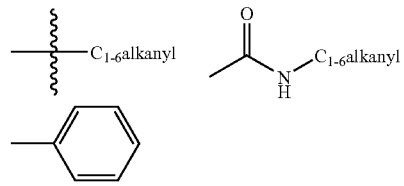

The present invention is directed, inter alia, to compounds of Formula (I) and compositions comprising a compound of Formula (I):

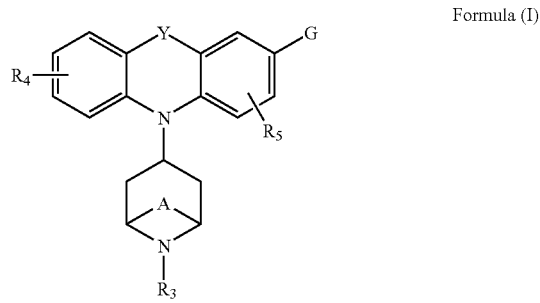

Formula (I)

wherein:

G is —C(Z)N(R₁)R₂, $C_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

R₁ is a substituent selected from the group consisting of hydrogen, $C_{1-8}$alkanyl, $C_{2-8}$alkenyl, and $C_{2-8}$alkynyl;

R₂ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —$(CH_2)_{3-5}$—, —$O(CH_2)_{2-4}$—, —$(CH_2)_{2-4}O$—, and —$O(CH_2)_{1-3}O$—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein $C_{6-10}$aryl is optionally substituted with one to three substitutents independently selected from the group consisting of $C_{1-6}$alkanyl, $C_{1-6}$alkoxy, halogen, and hydroxyl; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl and fluoroalkanyloxy; or optionally, when $R_4$ is two substituents attached to adjacent carbon atoms, the two substituents together form a single fused moiety; wherein the fused moiety is —$(CH_2)_{3-5}$—, —$O(CH_2)_{2-4}$—, —$(CH_2)_{2-4}O$—, —$O(CH_2)_{1-3}O$—, or —S—$C(NH_2)$=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —$(CH_2)_m$—, wherein m is 2 or 3;

Y is O or S;

Z is O, S, NH, N($C_{1-6}$alkanyl), N(OH), N(O$C_{1-6}$alkanyl), or N(phenyl);

and enantiomers, diastereomers, tautomers, solvates, or pharmaceutically acceptable salts thereof.

An embodiment of the present invention is directed to a compound of Formula (I) wherein the structure is numbered as defined herein and the substituents are as defined herein.

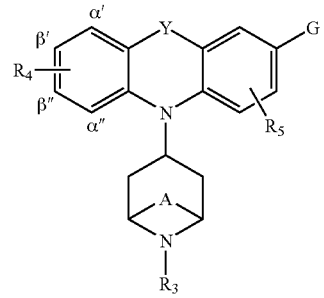

Formula (I)

The present invention is directed, inter alia, to analgesic and anti-pyretic uses of compositions comprising a compound of Formula (I):

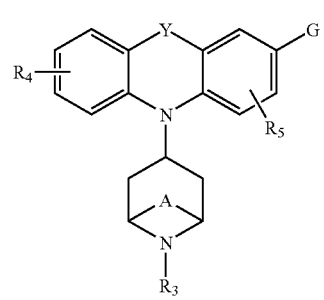

Formula (I)

wherein:

G is —C(Z)N($R_1$)$R_2$, $C_{6-10}$aryl, or a heterocycle selected from the group consisting of: imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy ($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

$R_1$ is a substituent selected from the group consisting of hydrogen, $C_{1-8}$alkanyl, $C_{2-8}$alkenyl, and $C_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanloxy substituents attached to adjacent carbon atoms, the two substituents can together form a fused cyclic alkanyl or cycloheteroalkanyl selected from the group consisting of —$(CH_2)_{3-5}$—, —$O(CH_2)_{2-4}$—, —$(CH_2)_{2-4}O$—, and —$O(CH_2)_{1-3}O$—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein $C_{6-10}$aryl is optionally substituted with one to three substituents independently selected from the group consisting of $C_{1-6}$alkanyl, $C_{1-6}$alkoxy, halogen, and hydroxy; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl and fluoroalkanyloxy; or optionally; when $R_4$ is two substituents attached to adjacent carbon atoms; the two substituents together form a single fused moiety; wherein the fused moiety is —$(CH_2)_{3-5}$—, —$O(CH_2)_{2-4}$—, —$(CH_2)_{2-4}O$—, —$O(CH_2)_{1-3}O$—, or —S—C(NH$_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —$(CH_2)_m$—, wherein m is 2 or 3;

Y is O or S;

Z is O, S, NH, N($C_{1-6}$alkanyl), N(OH), N(OC$_{1-6}$alkanyl), or N(phenyl);

and enantiomers, diastereomers, tautomers, solvates, or pharmaceutically acceptable salts thereof.

Embodiments of the present invention include compounds of Formula (I) wherein, preferably:

a) G is —C(Z)N($R_1$)$R_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

b) G is —C(Z)N($R_1$)$R_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl;

c) G is —C(Z)N($R_1$)$R_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl;

d) $R_1$ is a substituent selected from the group consisting of hydrogen and $C_{1-4}$alkanyl;

e) $R_1$ is selected from the group consisting of hydrogen, methyl, ethyl, and propyl;

f) $R_1$ is selected from the group consisting of hydrogen, methyl, or ethyl;

g) $R_2$ is selected from the group consisting of hydrogen; $C_{1-4}$alkanyl; phenyl; and $C_{1-6}$cycloalkanyl; wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; and wherein any phenyl-containing substituents and $C_{1-6}$cycloalkanyl substituents of $R_2$ are optionally substituted with one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-4}$alkanyl, hydroxy($C_{1-4}$)alkanyl, hydroxy, amino, $C_{1-6}$alkanylamino, di($C_{1-6}$alkanyl)amino, and fluoro;

h) $R_2$ is selected from the group consisting of hydrogen, $C_{1-4}$alkanyl, phenyl, and $C_{1-6}$cycloalkanyl, wherein $C_{1-4}$alkanyl is optionally substituted with one to three substituents independently selected from the group consisting of phenyl, $C_{1-4}$alkanyloxy, hydroxy, fluoro, aminocarbonyl, $C_{1-8}$alkanylaminocarbonyl, di($C_{1-8}$alkanyl)aminocarbonyl, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, hydroxy, and $C_{1-6}$alkanylthio; or $R_1$ and $R_2$ taken together with the nitrogen to which they are attached form a 5-7 membered cycloheteroalkyl optionally substituted with one to three substituents independently selected from the group consisting of $C_{1-4}$alkanyl and hydroxy;

i) $R_2$ is selected from the group consisting of hydrogen, $C_{1-4}$alkanyl and phenyl, wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

j) $R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O($CH_2$)$_{1-3}$O—;

k) $R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group;

l) $R_3$ is hydrogen, methyl, allyl, or heteroarylmethyl wherein heteroaryl is selected from the group consisting of benzo[1,3]dioxolyl, imidazolyl, furanyl, pyridinyl, and thienyl;

m) $R_4$ is one to three substituents independently selected from the group consisting of hydrogen; $C_{1-6}$alkanyl; $C_{1-6}$alkanyloxy; $C_{6-10}$arylamino wherein $C_{6-10}$aryl is optionally substituted with one to three substitutents independently selected from the group consisting of $C_{1-6}$alkanyl; $C_{1-6}$alkoxy, halogen, and hydroxy; formylamino; pyridinylamino; aminocarbonyl; $C_{1-6}$alkanylaminocarbonyl; $C_{1-6}$alkanylcarbonylamino; halogen; hydroxy; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; and thienyl;

n) $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

o) $R_4$ is one to two substituents independently selected from the group consisting of hydrogen, methyl, methoxy, bromo, fluoro, α'- or β'-phenyl, α'- or β'-pyridinyl, α'- or β'-furanyl, and hydroxy;

p) $R_5$ is one to two substituents independently selected from the group consisting of hydrogen and halogen;

q) $R_5$ is hydrogen;

r) A is —($CH_2$)$_{2-3}$—;

s) A is —($CH_2$)$_2$—;

t) Y is O or S;

u) Z is O, NH, N($C_{1-6}$alkanyl), N(OH), N(O$C_{1-6}$alkanyl), or N(phenyl);

v) Z is O, NH, or N(OH);

w) Z is O or NH;

aa) G is —C(Z)N($R_1$)$R_2$, phenyl, or a heterocycle selected from the group consisting of tetrazolyl, oxadizolyl, furyl, quinolinyl, thienyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

bb) G is —C(Z)N($R_1$)$R_2$, phenyl, or a heterocycle selected from the group consisting of tetrazolyl, oxadizolyl, furyl, quinolinyl, thienyl, and pyridinyl; wherein phenyl and the heterocycles of G are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl;

cc) G is —C(Z)N($R_1$)$R_2$; tetrazolyl; pyridinyl; oxadiazolyl optionally substituted with oxo; or phenyl optionally substituted with ($C_{1-8}$)alkanylcarbonylamino;

dd) G is —C(Z)N($R_1$)$R_2$, 1H-tetrazol-4-yl, 4H-[1,2,4]-oxadiazol-5-oxo-3-yl, 2-methylcarbonylaminophenyl, pyridin-3-yl or pyridin-4-yl;

dd) $R_2$ is selected from the group consisting of hydrogen and $C_{1-4}$alkanyl; wherein $C_{1-4}$alkanyl is optionally substituted with phenyl; or $R_1$ and $R_2$ taken together with the nitrogen to which they are attached form a pyrrolidinyl wherein said pyrrolidinyl is optionally substituted with hydroxy;

ee) $R_2$ is selected from the group consisting of hydrogen, methyl, ethyl, and phenethyl; or $R_1$ and $R_2$ taken together with the nitrogen to which they are attached form pyrrolidin-1-yl, 3-hydroxypyrrolidin-1-yl or 3-(S)-hydroxypyrrolidin-1-yl;

ff) $R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, thiazolyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O($CH_2$)$_{1-3}$O—;

gg) $R_3$ is selected from the group consisting of hydrogen, methyl, methylbutenyl, propenyl, benzyl, phenethyl, and heteroaryl($C_{1-8}$)alkanyl wherein the heteroaryl is selected from the group consisting of imidazolyl, furanyl, pyridinyl, thienyl, and thiazolyl;

hh) $R_3$ is selected from the group consisting of hydrogen, methyl, 3-methyl-2-butenyl, 2-propenyl, benzyl, 2-phenethyl, pyridin-2-ylmethyl, fur-3-ylmethyl, thiophene-2-ylmethyl, 1H-imidazol-2-ylmethyl, and thiazol-2-ylmethyl;

ii) $R_4$ is one to two substituents independently selected from the group consisting of hydrogen, methyl, phenyl, bromo, fluoro, aminocarbonyl, chloro and hydroxy;

jj) $R_4$ is one to two substituents independently selected from the group consisting of hydrogen, α'-hydroxy and α'-methoxy;

kk) $R_4$ is unsubstituted or substituted at the α' position;

ll) $R_4$ is hydrogen and Y is O;

mm) $R_4$ is α'-hydroxy and Y is O;

nn) $R_4$ is hydrogen and Y is S;

oo) $R_4$ is α'-hydroxy and Y is S;

and combinations of a) through oo) above.

One embodiment of the present invention is a compound of Formula (I) wherein:

G is —C(Z)N($R_1$)$R_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

$R_1$ is hydrogen or $C_{1-4}$alkanyl;

$R_2$ is selected from the group consisting of hydrogen; $C_{1-4}$alkanyl; phenyl; and $C_{1-6}$cycloalkanyl; wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; and wherein the phenyl and $C_{1-6}$cycloalkanyl substituents of $R_2$ are optionally substituted with one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-4}$alkanyl, hydroxy($C_{1-4}$)alkanyl, hydroxy, amino, $C_{1-6}$alkanylamino, di($C_{1-6}$alkanyl)amino, and fluoro;

$R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

R$_4$ is one to three substituents independently selected from the group consisting of hydrogen; C$_{1-6}$alkanyl; C$_{1-6}$alkanyloxy; C$_{6-10}$arylamino wherein C$_{6-10}$aryl is optionally substituted with one to three substituents independently selected from the group consisting of C$_{1-6}$alkanyl; C$_{1-6}$alkoxy, halogen, and hydroxy; formylamino; pyridinylamino; aminocarbonyl; C$_{1-6}$alkanylaminocarbonyl; C$_{1-6}$alkanylcarbonylamino; halogen; hydroxy; C$_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; and thienyl;

R$_5$ is one to two substituents independently selected from the group consisting of hydrogen and halogen;

A is CH$_2$CH$_2$;

Y is O or S;

Z is O, NH, N(C$_{1-6}$alkanyl), N(OH), N(OC$_{1-6}$alkanyl), or N(phenyl); and enantiomers, diastereomers, tautomers, solvates, and pharmaceutically acceptable salts thereof.

Another embodiment of the present invention is a compound of Formula (I) wherein:

G is —C(Z)N(R$_1$)R$_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G (described herein) are optionally substituted with one to three substituents independently selected from the group consisting of C$_{1-4}$alkanyl, C$_{1-4}$alkanyloxy, hydroxy(C$_{1-4}$)alkanyl, carboxy(C$_{1-4}$)alkanyl, C$_{1-4}$alkanylcarbonylamino, hydroxy, cyano, oxo, thioxo, amino, C$_{1-6}$alkanylamino, di(C$_{1-6}$alkanyl)amino, C$_{1-8}$alkanylthio, aminocarbonyl, aminothiocarbonyl, C$_{1-8}$alkanylaminocarbonyl, and di(C$_{1-8}$alkanyl)aminocarbonyl;

R$_1$ is selected from the group consisting of hydrogen, methyl, ethyl, and propyl;

R$_2$ is selected from the group consisting of hydrogen, C$_{1-4}$alkanyl, phenyl, and C$_{1-6}$cycloalkanyl; wherein C$_{1-4}$alkanyl is optionally substituted with one to three substituents independently selected from the group consisting of phenyl, C$_{1-4}$alkanyloxy, hydroxy, fluoro, aminocarbonyl, C$_{1-8}$alkanylaminocarbonyl, di(C$_{1-8}$alkanyl)aminocarbonyl, and phenoxy; and wherein any phenyl-containing substituent of R$_2$ is optionally substituted with one to three substituents independently selected from the group consisting of C$_{1-6}$alkanyl, C$_{1-6}$alkanyloxy, fluoro, hydroxy, and C$_{1-6}$alkanylthio; or R$_1$ and R$_2$ taken together with the nitrogen to which they are attached form a pyrrolidinyl or piperidinyl ring wherein said pyrrolidinyl or piperidinyl is optionally substituted with a substituent selected from the group consisting of C$_{1-3}$alkanyl and hydroxy;

R$_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl(C$_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl wherein the phenyl in any phenyl-containing substituent is optionally substituted with one hydroxyl group;

R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

R$_5$ is hydrogen;

A is CH$_2$CH$_2$;

Y is O or S;

Z is O, NH, or N(OH); and enantiomers, diastereomers, tautomers, solvates, and pharmaceutically acceptable salts thereof.

Another embodiment of the present invention is directed to compositions comprising a compound of Formula (I) wherein:

G is selected from —C(Z)N(R$_1$)R$_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G are optionally substituted with one to three substituents independently selected from the group consisting of C$_{1-4}$alkanyl, C$_{1-4}$alkanyloxy, hydroxy(C$_{1-4}$)alkanyl, C$_{1-4}$alkanylcarbonylamino, hydroxy, cyano, oxo, thioxo, and aminocarbonyl;

R$_1$ is hydrogen, methyl, or ethyl;

R$_2$ is independently selected from the group consisting of hydrogen, C$_{1-4}$alkanyl and phenyl; wherein C$_{1-4}$alkanyl is optionally substituted with one to three substituents independently selected from the group consisting of phenyl, C$_{1-4}$alkanyloxy, hydroxy, fluoro, and phenoxy; and wherein any phenyl-containing substituent of R$_2$ is optionally substituted with one to three substituents independently selected from the group consisting of C$_{1-6}$alkanyl, C$_{1-6}$alkanyloxy, fluoro, and hydroxy; or R$_1$ and R$_2$ taken together with the nitrogen to which they are attached form a pyrrolidinyl or piperidinyl ring wherein said pyrrolidinyl or piperidinyl are optionally substituted with a substituent selected from the group consisting of C$_{1-3}$alkanyl and hydroxy;

R$_3$ is hydrogen, methyl, allyl, or heteroarylmethyl wherein heteroaryl is selected from the group consisting of benzo[1,3]dioxolyl, imidazolyl, furanyl, pyridinyl, and thienyl;

R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

A is CH$_2$CH$_2$;

Y is O or S;

Z is O or NH; and enantiomers, diasteromers, tautomers, solvates, and pharmaceutically acceptable salts thereof.

Another embodiment of the present invention is directed to compounds of Formula (I) wherein:

G is —C(Z)N(R$_1$)R$_2$, phenyl, or a heterocycle selected from the group consisting of tetrazolyl, oxadiazolyl, furyl, quinolinyl, thienyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

$R_1$ is $C_{1-4}$ alkanyl, or hydrogen;

$R_2$ is hydrogen or $C_{1-4}$ alkanyl optionally substituted with phenyl;

or $R_1$ and $R_2$ taken together with the nitrogen to which they are attached form a pyrrolidinyl ring optionally substituted with hydroxy;

Z is NH or oxygen;

$R_3$ is pyridinyl($C_{1-8}$)alkanyl, furyl($C_{1-8}$)alkanyl, $C_{1-8}$ alkanyl, hydrogen, $C_{2-8}$ alkenyl, thienyl($C_{1-8}$)alkanyl, imidazolyl($C_{1-8}$)alkanyl, phenyl($C_{1-8}$)alkanyl, or thiazolyl ($C_{1-8}$)alkanyl;

$R_4$ is hydrogen, $C_{1-6}$ alkanyl, $C_{1-6}$ alkanyloxy, hydroxy, halogen, aminocarbonyl, or phenyl;

$R_5$ is hydrogen;

A is $CH_2CH_2$;

Y is O or S;

Z is O or NH; and enantiomers, diastereomers, tautomers, solvates, and pharmaceutically acceptable salts thereof.

Another embodiment of the present invention is directed to compounds of Formula (I) wherein:

G is —$C(Z)N(R_1)R_2$; tetrazolyl, oxadiazolyl optionally substituted with oxo; phenyl optionally substituted with ($C_{1-8}$)alkanylcarbonylamino; or pyridinyl;

$R_1$ is $C_{1-4}$ alkanyl, or hydrogen;

$R_2$ is hydrogen or $C_{1-4}$ alkanyl optionally substituted with phenyl;

or $R_1$ and $R_2$ taken together with the nitrogen to which they are attached form a pyrrolidinyl ring optionally substituted with hydroxy;

Z is NH or oxygen;

$R_3$ is pyridinyl($C_{1-8}$)alkanyl, furyl($C_{1-8}$)alkanyl, $C_{1-8}$ alkanyl, hydrogen, $C_{2-8}$ alkenyl, thienyl($C_{1-8}$)alkanyl, imidazolyl($C_{1-8}$)alkanyl, phenyl($C_{1-8}$)alkanyl, or thiazolyl ($C_{1-8}$)alkanyl;

$R_4$ is hydrogen, $\alpha'$-hydroxy, or $\alpha'$-methoxy;

$R_5$ is hydrogen;

A is $CH_2CH_2$;

Y is O or S;

Z is O or NH; and enantiomers, diastereomers, tautomers, solvates, and pharmaceutically acceptable salts thereof.

Another embodiment of the present invention is directed to compounds of Formula (I) wherein:

G is —$C(Z)N(R_1)R_2$, 1H-tetrazol-4-yl, 4H-[1,2,4]-oxadiazol-5-oxo-3-yl, 2-methylcarbonylaminophenyl, 3-furyl, quinolin-3-yl, thiophen-3-yl, pyridin-3-yl or pyridin-4-yl, $R_1$ is hydrogen, ethyl, or methyl, $R_2$ is methyl, ethyl, phenethyl, or hydrogen;

or $R_1$ and $R_2$ taken together with the nitrogen to which they are attached form pyrrolidin-1-yl, 3-hydroxypyrrolidin-1-yl, or 3-(S)-hydroxypyrrolidin-1-yl;

Z is NH or oxygen;

$R_3$ is pyridin-2-ylmethyl, fur-3-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, benzyl, or allyl;

$R_4$ is hydrogen, $\alpha'$-methyl, $\alpha'$-phenyl, $\beta''$-bromo, $\beta''$-fluoro, $\alpha'$-aminocarbonyl, $\alpha'$-chloro, $\alpha'$-methoxy; or $\alpha'$-hydroxy;

$R_5$ is hydrogen;

A is $CH_2CH_2$;

Y is O or S;

Z is O or NH; and enantiomers, diastereomers, tautomers, solvates, and pharmaceutically acceptable salts thereof.

Another embodiment of the present invention is directed to compounds of Formula (I) wherein:

G is —$C(Z)N(R_1)R_2$, 1H-tetrazol-4-yl, 4H-[1,2,4]-oxadiazol-5-oxo-3-yl, 2-methylcarbonylaminophenyl, pyridin-3-yl or pyridin-4-yl;

$R_1$ is hydrogen, ethyl, or methyl;

$R_2$ is methyl, ethyl, phenethyl, or hydrogen;

or $R_1$ and $R_2$ taken together with the nitrogen to which they are attached form pyrrolidin-1-yl, 3-hydroxypyrrolidin-1-yl, or 3-(S)-hydroxypyrrolidin-1-yl;

Z is NH or oxygen;

$R_3$ is pyridin-2-ylmethyl, fur-3-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, or benzyl;

$R_4$ is hydrogen, $\alpha'$-hydroxy, or $\alpha'$-methoxy;

$R_5$ is hydrogen;

A is $CH_2CH_2$;

Y is O or S;

Z is O or NH; and enantiomers, diastereomers, tautomers, solvates, and pharmaceutically acceptable salts thereof.

In certain embodiments of Formula (I) when $R_1$ and $R_2$ are taken together with the nitrogen to which they are attached to form a 5-7 membered cycloheteroalkyl optionally substituted with one to three substituents independently selected from the group consisting of $C_{1-8}$alkanyl, hydroxy ($C_{1-8}$)alkanyl, hydroxy, amino, $C_{1-6}$alkanylamino, di($C_{1-6}$alkanyl)amino, and halogen;

Z is oxygen.

In certain embodiments of Formula (I) when $R_1$ and $R_2$ are taken together with the nitrogen to which they are attached to form a pyrrolidinyl ring optionally substituted with hydroxy, Z is oxygen.

Another embodiment of the present invention is a compound of Formula (I) wherein:

G is selected from —$C(Z)N(R_1)R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;

$R_1$ is hydrogen, methyl, or ethyl;

$R_2$ is selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy;

or $R_1$ and $R_2$ taken together with the nitrogen to which they are attached form a pyrrolidinyl or piperidinyl ring;

$R_3$ is selected from the group consisting of hydrogen, $C_{1-8}$alkanyl, $C_{2-8}$alkenyl, $C_{2-8}$alkynyl, $C_{1-8}$alkanyloxy ($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of hydrogen, methyl, allyl, or heteroarylmethyl; wherein heteroaryl is selected from the group consisting of benzo[1,3]dioxolyl, imidazolyl, furanyl, pyridinyl, and thienyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O($CH_2$)$_{1-3}$O—;

$R_4$ is one to three substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

$R_5$ is hydrogen;

A is $CH_2CH_2$;

Y is O or S;

Z is O or NH; and enantiomers, diastereomers, tautomers, solvates, and pharmaceutically acceptable salts thereof.

Another embodiment of the present invention is directed to compositions comprising a compound of Formula (I) wherein G is independently selected from —C(Z)N($R_1$)$R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, and pyridin-3-yl; $R_1$ is hydrogen, methyl, or ethyl; $R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, and 2,6-dimethyl-phenoxy; and wherein the any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy; $R_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-ylmethyl; $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy; $R_5$ is H; A is $CH_2CH_2$; Y is or S; and Z is O or NH.

Another embodiment of the present invention is directed to compositions comprising a compound of Formula (I) wherein G is selected from —C(Z)N($R_1$)$R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; $R_1$ is hydrogen, methyl, or ethyl; $R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, methoxy, hydroxy, and 2,6-dimethyl-phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl are optionally substituted with a substituent selected from the group consisting of $C_{1-3}$alkanyl and hydroxy; $R_3$ is a substituent selected from the group consisting of benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl; $R_4$ is one to two substituents independently selected from the group consisting of hydrogen, methyl, methoxy, bromo, fluoro, α'- or β'-phenyl, α'- or β'-pyridinyl, α'- or β'-furanyl, and hydroxy; $R_5$ is H; A is $CH_2CH_2$; Y is O or S; and Z is O or NH.

Another embodiment of the present invention is directed to compositions comprising a compound of Formula (I) wherein G is selected from —C(Z)N($R_1$)$R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; $R_1$ is hydrogen, methyl, or ethyl; $R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, methoxy, hydroxy, and 2,6-dimethyl-phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; alternatively $R_1$ and $R_2$ are taken together with the nitrogen to which they are attached to form a pyrrolidinyl or piperidinyl ring wherein said pyrrolidinyl or piperidinyl are optionally substituted with a substituent selected from the group consisting of $C_{1-3}$alkanyl and hydroxy; $R_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl; $R_4$ is a substituent independently selected from the group consisting of hydrogen, methyl, methoxy, bromo, fluoro α'- or β'-phenyl, α'- or β'-pyridinyl, α'- or β'-furanyl, and hydroxy; $R_5$ is H; A is $CH_2CH_2$; Y is O or S; and Z is O or NH.

Another embodiment of the present invention is directed to a compound of Formula (I) wherein $R_4$ is preferably substituted at the α'- or β'-position of Formula (I).

Another embodiment of the present invention is directed to compositions comprising a compound selected from the group consisting of:

a compound of Formula (I) wherein G is N,N-diethylaminocarbonyl; $R^3$ is 1H-imidazol-2-yl-methyl; $R^4$ is α'-hydroxy; $R^5$ is H; Y is O; and A is —$CH_2CH_2$—;

a compound of Formula (I) wherein G is N,N-diethylaminocarbonyl; $R^3$ is furan-3-yl-methyl; $R^4$ is α'-hydroxy; $R^5$ is H; Y is O; and A is —$CH_2CH_2$—;

a compound of Formula (I) wherein G is N,N-diethylaminocarbonyl; $R^3$ is H; $R^4$ is α'-hydroxy; $R^5$ is H; Y is O; and A is —CH$_2$CH$_2$—;
a compound of Formula (I) wherein G is N,N-diethylaminocarbonyl; $R^3$ is H; $R^4$ is α'-methoxy; $R^5$ is H; Y is O; and A is —CH$_2$CH$_2$—;
a compound of Formula (I) wherein G is N,N-diethylaminocarbonyl; $R^3$ is pyridin-2-yl-methyl; $R^4$ is H; $R^5$ is H; Y is O; A is —CH$_2$CH$_2$—;
a compound of Formula (I) wherein G is N,N-diethylaminocarbonyl; $R^3$ is furan-3-yl-methyl; $R^4$ is H; $R^5$ is H; Y is O; and A is —CH$_2$CH$_2$—;
a compound of Formula (I) wherein G is N,N-diethylaminocarbonyl; $R^3$ is thien-2-yl-methyl; $R^4$ is H; $R^5$ is H; Y is O; and A is —CH$_2$CH$_2$—;
a compound of Formula (I) wherein G is N,N-diethylaminocarbonyl; $R^3$ is benzyl; $R^4$ is H; $R^5$ is H; Y is O; and A is —CH$_2$CH$_2$—;
a compound of Formula (I) wherein G is pyridin-3-yl; $R^3$ is furan-3-yl methyl; $R^4$ is H; $R^5$ is H; Y is O; and A is —CH$_2$CH$_2$—;
a compound of Formula (I) wherein G is N,N-diethylaminocarbonyl; $R^3$ is furan-2-yl methyl; $R^4$ is H; $R^5$ is H; Y is O; and A is —CH$_2$CH$_2$—;
a compound of Formula (I) wherein G is N,N-diethylaminocarbonyl; $R^3$ is H; $R^4$ is α'-methyl; $R^5$ is H; Y is O; and A is —CH$_2$CH$_2$—;
a compound of Formula (I) wherein G is N,N-diethylaminocarbonyl; $R^3$ is H; $R^4$ is α'-phenyl; $R^5$ is H; Y is O; and A is —CH$_2$CH$_2$—;
a compound of Formula (I) wherein G is N,N-diethylaminocarbonyl; $R^3$ is H; $R^4$ is H; $R^5$ is H; Y is O; and A is —CH$_2$CH$_2$—;
a compound of Formula (I) wherein G is N,N-diethylaminocarbonyl; $R^3$ is H; $R^4$ is H; $R^5$ is H; Y is O; and A is —CH$_2$CH$_2$—;
a compound of Formula (I) wherein G is N,N-diethylaminocarbonyl; $R^3$ is H; $R^4$ is β"-bromo; $R^5$ is H; Y is O; and A is —CH$_2$CH$_2$—;
a compound of Formula (I) wherein G is N,N-diethylaminocarbonyl; $R^3$ is H; $R^4$ is H; $R^5$ is H; Y is O; and A is —CH$_2$CH$_2$—;
a compound of Formula (I) wherein G is N,N-diethylaminocarbonyl; $R^3$ is H; $R^4$ is α'-chloro; $R^5$ is H; Y is O; and A is —CH$_2$CH$_2$—;
a compound of Formula (I) wherein G is N,N-diethylaminocarbonyl; $R^3$ is H; $R^4$ is β"-fluoro; $R^5$ is H; Y is O; and A is —CH$_2$CH$_2$—;
a compound of Formula (I) wherein G is 2-methylcarbonylamino-phenyl; $R^3$ is H; $R^4$ is H; $R^5$ is H; Y is O; and A is —CH$_2$CH$_2$—;
a compound of Formula (I) wherein G is pyrrolidin-1-yl; $R^3$ is H; $R^4$ is H; $R^5$ is H; Y is O; and A is —CH$_2$CH$_2$—;
a compound of Formula (I) wherein G is N,N-diethylaminocarbonyl; $R^3$ is furan-3-yl-methyl; $R^4$ is H; $R^5$ is H; Y is O; and A is —CH$_2$CH$_2$—;

Another embodiment of the present invention is directed to compounds and compositions comprising a compound selected from the group consisting of:
10-(8-Methyl-8-aza-bicyclo[3.2.1]oct-3-yl)-10H-phenoxazine-3-carboxylic acid diethylamide;
(3-Hydroxy-pyrrolidin-1-yl)-[10-(8-methyl-8-aza-bicyclo[3.2.1]oct-3-yl)-10H-phenoxazin-3-yl]-methanone;
10-(8-Methyl-8-aza-bicyclo[3.2.1]oct-3-yl)-10H-phenoxazine-3-carboxylic acid methyl-phenethyl-amide;
Endo-10-(8-Aza-bicyclo[3.2.1]oct-3-yl)-3-(1H-tetrazol-5-yl)-10H-phenoxazine;
Endo-10-(8-Pyridin-2-ylmethyl-8-aza-bicyclo[3.2.1]oct-3-yl)-3-(1H-tetrazol-5-yl)-10H-phenoxazine;
Endo-10-(8-Phenethyl-8-aza-bicyclo[3.2.1]oct-3-yl)-3-(1H-tetrazol-5-yl)-10H-phenoxazine;
Endo-10-(8-Aza-bicyclo[3.2.1]oct-3-yl)-10H-phenoxazine-3-carbonitrile;
Endo-10-(8-Aza-bicyclo[3.2.1]oct-3-yl)-N,N-diethyl-10H-phenoxazine-3-carboxamidine;
Endo-N,N-Diethyl-10-(8-pyridin-2-ylmethyl-8-aza-bicyclo[3.2.1]oct-3-yl)-10H-phenoxazine-3-carboxamidine;
Endo-N,N-Diethyl-10-(8-phenethyl-8-aza-bicyclo[3.2.1]oct-3-yl)-10H-phenoxazine-3-carboxamidine;
Endo-3-[10-(8-Aza-bicyclo[3.2.1]oct-3-yl)-10H-phenoxazin-3-yl]-4H-[1,2,4]oxadiazol-5-one;
endo-10-(8-Aza-bicyclo[3.2.1]oct-3-yl)-10H-phenoxazine-3-carboxylic acid amide;
Endo-3-[10-(8-Pyridin-2-ylmethyl-8-aza-bicyclo[3.2.1]oct-3-yl)-10H-phenoxazin-3-yl]-4H-[1,2,4]oxadiazol-5-one;
Endo-3-[10-(8-Phenethyl-8-aza-bicyclo[3.2.1]oct-3-yl)-10H-phenoxazin-3-yl]-4H-[1,2,4]oxadiazol-5-one;
10-(8-Methyl-8-aza-bicyclo[3.2.1]oct-3-yl)-10H-phenoxazine-3-carboxylic acid diethylamide;
10-(8-Aza-bicyclo[3.2.1]oct-3-yl)-6-methoxy-10H-phenoxazine-3-carboxylic acid diethylamide;
6-Methoxy-10-(8-phenethyl-8-aza-bicyclo[3.2.1]oct-3-yl)-10H-phenoxazine-3-carboxylic acid diethylamide;
6-Hydroxy-10-(8-phenethyl-8-aza-bicyclo[3.2.1]oct-3-yl)-10H-phenoxazine-3-carboxylic acid diethylamide;
6-Methoxy-10-(8-methyl-8-aza-bicyclo[3.2.1]oct-3-yl)-10H-phenoxazine-3-carboxylic acid diethylamide;
10-(8-Methyl-8-aza-bicyclo[3.2.1]oct-3-yl)-3-(1H-tetrazol-5-yl)-10H-phenoxazine;
N,N-Diethyl-10-(8-methyl-8-aza-bicyclo[3.2.1]oct-3-yl)-10H-phenoxazine-3-carboxamidine;
3-[10-(8-Methyl-8-aza-bicyclo[3.2.1]oct-3-yl)-10H-phenoxazin-3-yl]-4H-[1,2,4]oxadiazol-5-one;
10-(8-Furan-3-ylmethyl-8-aza-bicyclo[3.2.1]oct-3-yl)-3-pyridin-3-yl-10H-phenothiazine;
N-{2-[10-(8-Furan-3-ylmethyl-8-aza-bicyclo[3.2.1]oct-3-yl)-10H-phenothiazin-3-yl]-phenyl}-acetamide;
10-[8-(3-Methyl-but-2-enyl)-8-aza-bicyclo[3.2.1]oct-3-yl]-3-pyridin-3-yl-10H-phenothiazine;
3-Pyridin-3-yl-10-(8-pyridin-2-ylmethyl-8-aza-bicyclo[3.2.1]oct-3-yl)-10H-phenothiazine;
10-[8-(3-Methyl-but-2-enyl)-8-aza-bicyclo[3.2.1]oct-3-yl]-3-pyridin-4-yl-10H-phenothiazine;
3-Pyridin-4-yl-10-(8-pyridin-2-ylmethyl-8-aza-bicyclo[3.2.1]oct-3-yl)-10H-phenothiazine;
3-Pyridin-4-yl-10-(8-thiophen-2-ylmethyl-8-aza-bicyclo[3.2.1]oct-3-yl)-10H-phenothiazine;
N-{2-[10-(8-Allyl-8-aza-bicyclo[3.2.1]oct-3-yl)-10H-phenothiazin-3-yl]-phenyl}-acetamide;
N-{2-[10-(8-Phenethyl-8-aza-bicyclo[3.2.1]oct-3-yl)-10H-phenothiazin-3-yl]-phenyl}-acetamide;
N-(2-{10-[8-(1H-Imidazol-2-ylmethyl)-8-aza-bicyclo[3.2.1]oct-3-yl]-10H-phenothiazin-3-yl}-phenyl)-acetamide;
N-{2-[10-(8-Methyl-8-aza-bicyclo[3.2.1]oct-3-yl)-10H-phenothiazin-3-yl]-phenyl}-acetamide;
10-(8-Aza-bicyclo[3.2.1]oct-3-yl)-3-pyridin-3-yl-10H-phenothiazine;
N-{2-[10-(8-Aza-bicyclo[3.2.1]oct-3-yl)-10H-phenothiazin-3-yl]-phenyl}-acetamide;
10-8-Allyl-8-aza-bicyclo[3.2.1]oct-3-yl)-3-pyridin-3-yl-10H-phenothiazine;
Endo-10-(8-Aza-bicyclo[3.2.1]oct-3-yl)-3-pyridin-3-yl-10H-phenoxazine;

Endo-10-(8-Phenethyl-8-aza-bicyclo[3.2.1]oct-3-yl)-3-pyridin-3-yl-10H-phenoxazine;
Endo-3-Pyridin-3-yl-10-(8-pyridin-2-ylmethyl-8-aza-bicyclo[3.2.1]oct-3-yl)-10H-phenoxazine;
Endo-10-(8-Furan-3-ylmethyl-8-aza-bicyclo[3.2.1]oct-3-yl)-3-pyridin-3-yl-10H-phenoxazine;
Endo-3-Pyridin-3-yl-10-(8-thiophen-2-ylmethyl-8-aza-bicyclo[3.2.1]oct-3-yl)-10H-phenoxazine;
Endo-10-(8-Aza-bicyclo[3.2.1]oct-3-yl)-3-chloro-10H-phenoxazine;
Endo-10-(8-Aza-bicyclo[3.2.1]oct-3-yl)-3-pyridin-4-yl-10H-phenoxazine;
Endo-10-(8-Phenethyl-8-aza-bicyclo[3.2.1]oct-3-yl)-3-pyridin-4-yl-10H-phenoxazine;
Endo-3-Pyridin-4-yl-10-(8-pyridin-2-ylmethyl-8-aza-bicyclo[3.2.1]oct-3-yl)-10H-phenoxazine;
Endo-10-(8-Furan-3-ylmethyl-8-aza-bicyclo[3.2.1]oct-3-yl)-3-pyridin-4-yl-10H-phenoxazine;
Endo-3-Pyridin-4-yl-10-(8-thiophen-2-ylmethyl-8-aza-bicyclo[3.2.1]oct-3-yl)-10H-phenoxazine;
Exo-3-(3-Pyridin-3-yl-phenoxazin-10-yl)-8-aza-bicyclo[3.2.1]octane-8-carboxylic acid tert-butyl ester;
Exo-10-(8-Phenethyl-8-aza-bicyclo[3.2.1]oct-3-yl)-3-pyridin-3-yl-10H-phenoxazine;
Exo-3-Pyridin-3-yl-10-(8-pyridin-2-ylmethyl-8-aza-bicyclo[3.2.1]oct-3-yl)-10H-phenoxazine;
Exo-10-(8-Furan-3-ylmethyl-8-aza-bicyclo[3.2.1]oct-3-yl)-3-pyridin-3-yl-10H-phenoxazine;
Exo-10-(8-Aza-bicyclo[3.2.1]oct-3-yl)-3-chloro-10H-phenoxazine;
Exo-10-(8-Aza-bicyclo[3.2.1]oct-3-yl)-3-pyridin-4-yl-10H-phenoxazine;
Exo-10-(8-Phenethyl-8-aza-bicyclo[3.2.1]oct-3-yl)-3-pyridin-4-yl-10H-phenoxazine;
Exo-3-Pyridin-4-yl-10-(8-pyridin-2-ylmethyl-8-aza-bicyclo[3.2.1]oct-3-yl)-10H-phenoxazine;
Exo-10-(8-Furan-3-ylmethyl-8-aza-bicyclo[3.2.1]oct-3-yl)-3-pyridin-4-yl-10H-phenoxazine;
Exo-10-(8-Aza-bicyclo[3.2.1]oct-3-yl)-3-(1H-tetrazol-5-yl)-10H-phenoxazine;
Exo-10-(8-Aza-bicyclo[3.2.1]oct-3-yl)-10H-phenoxazine-3-carbonitrile;
Exo-3-[10-(8-Aza-bicyclo[3.2.1]oct-3-yl)-10H-phenoxazin-3-yl]-4H-[1,2,4]oxadiazol-5-one;
6-Methoxy-10-(8-methyl-8-aza-bicyclo[3.2.1]oct-3-yl)-10H-phenoxazine-3-carbonitrile;
6-Hydroxy-10-(8-methyl-8-aza-bicyclo[3.2.1]oct-3-yl)-10H-phenoxazine-3-carbonitrile;
[10-(8-Furan-3-ylmethyl-8-aza-bicyclo[3.2.1]oct-3-yl)-10H-phenothiazin-3-yl]-pyrrolidin-1-yl-methanone;
[10-(8-Phenethyl-8-aza-bicyclo[3.2.1]oct-3-yl)-10H-phenothiazin-3-yl]-pyrrolidin-1-yl-methanone;
{10-[8-(3-Methyl-but-2-enyl)-8-aza-bicyclo[3.2.1]oct-3-yl]-10H-phenothiazin-3-yl}-pyrrolidin-1-yl-methanone;
[10-(8-Furan-3-ylmethyl-8-aza-bicyclo[3.2.1]oct-3-yl)-10H-phenothiazin-3-yl]-(3-hydroxy-pyrrolidin-1-yl)-methanone;
(3-Hydroxy-pyrrolidin-1-yl)-[10-(8-phenethyl-8-aza-bicyclo[3.2.1]oct-3-yl)-10H-phenothiazin-3-yl]-methanone;
{10-[8-(3-Methyl-but-2-enyl)-8-aza-bicyclo[3.2.1]oct-3-yl]-10H-phenothiazin-3-yl}-(3-methyl-pyrrolidin-1-yl)-methanone;
[10-(8-Methyl-8-aza-bicyclo[3.2.1]oct-3-yl)-10H-phenothiazin-3-yl]-pyrrolidin-1-yl-methanone;
(3-Hydroxy-pyrrolidin-1-yl)-[10-(8-methyl-8-aza-bicyclo[3.2.1]oct-3-yl)-10H-phenothiazin-3-yl]-methanone;
10-(8-Methyl-8-aza-bicyclo[3.2.1]oct-3-yl)-10H-phenothiazine-3-carboxylic acid ethylamide;
Endo-10-(8-Aza-bicyclo[3.2.1]oct-3-yl)-10H-phenoxazine-3-carboxylic acid diethylamide;
Endo-10-(8-Thiophen-2-ylmethyl-8-aza-bicyclo[3.2.1]oct-3-yl)-10H-phenoxazine-3-carboxylic acid diethylamide;
Endo-10-(8-Pyridin-2-ylmethyl-8-aza-bicyclo[3.2.1]oct-3-yl)-10H-phenoxazine-3-carboxylic acid diethylamide;
Endo-10-(8-Thiazol-2-ylmethyl-8-aza-bicyclo[3.2.1]oct-3-yl)-10H-phenoxazine-3-carboxylic acid diethylamide;
Endo-10-(8-Phenethyl-8-aza-bicyclo[3.2.1]oct-3-yl)-10H-phenoxazine-3-carboxylic acid diethylamide;
Endo-10-(8-Pyridin-3-ylmethyl-8-aza-bicyclo[3.2.1]oct-3-yl)-10H-phenoxazine-3-carboxylic acid diethylamide;
Endo-10-[8-(3-Methyl-but-2-enyl)-8-aza-bicyclo[3.2.1]oct-3-yl]-10H-phenoxazine-3-carboxylic acid diethylamide;
Endo-10-[8-(1H-Imidazol-2-ylmethyl)-8-aza-bicyclo[3.2.1]oct-3-yl]-10H-phenoxazine-3-carboxylic acid diethylamide;
Endo-10-(8-Benzyl-8-aza-bicyclo[3.2.1]oct-3-yl)-10H-phenoxazine-3-carboxylic acid diethylamide;
Exo-10-(8-Aza-bicyclo[3.2.1]oct-3-yl)-10H-phenoxazine-3-carboxylic acid diethylamide;
Exo-10-(8-Phenethyl-8-aza-bicyclo[3.2.1]oct-3-yl)-10H-phenoxazine-3-carboxylic acid diethylamide;
Exo-10-(8-Pyridin-3-ylmethyl-8-aza-bicyclo[3.2.1]oct-3-yl)-10H-phenoxazine-3-carboxylic acid diethylamide;
Exo-10-(8-Thiophen-2-ylmethyl-8-aza-bicyclo[3.2.1]oct-3-yl)-10H-phenoxazine-3-carboxylic acid diethylamide;
Exo-10-[8-(3-Methyl-but-2-enyl)-8-aza-bicyclo[3.2.1]oct-3-yl]-10H-phenoxazine-3-carboxylic acid diethylamide;
Exo-10-(8-Pyridin-2-ylmethyl-8-aza-bicyclo[3.2.1]oct-3-yl)-10H-phenoxazine-3-carboxylic acid diethylamide;
Exo-10-(8-Benzyl-8-aza-bicyclo[3.2.1]oct-3-yl)-10H-phenoxazine-3-carboxylic acid diethylamide;
Exo-10-(8-Thiazol-2-ylmethyl-8-aza-bicyclo[3.2.1]oct-3-yl)-10H-phenoxazine-3-carboxylic acid diethylamide;
Exo-10-(8-Furan-3-ylmethyl-8-aza-bicyclo[3.2.1]oct-3-yl)-10H-phenoxazine-3-carboxylic acid diethylamide;
Exo-10-[8-(1H-Imidazol-2-ylmethyl)-8-aza-bicyclo[3.2.1]oct-3-yl]-10H-phenoxazine-3-carboxylic acid diethylamide;
Endo-10-(8-Aza-bicyclo[3.2.1]oct-3-yl)-7-pyridin-3-yl-10H-phenoxazin-4-ol;
Endo-7-Pyridin-3-yl-10-(8-pyridin-2-ylmethyl-8-aza-bicyclo[3.2.1]oct-3-yl)-10H-phenoxazin-4-ol;
Endo-10-(8-Aza-bicyclo[3.2.1]oct-3-yl)-3-chloro-6-methoxy-10H-phenoxazine;
Endo-10-(8-Aza-bicyclo[3.2.1]oct-3-yl)-6-methoxy-3-pyridin-3-yl-10H-phenoxazine;
Endo-6-Methoxy-3-pyridin-3-yl-10-(8-pyridin-2-ylmethyl-8-aza-bicyclo[3.2.1]oct-3-yl)-10H-phenoxazine;
Endo-10-(8-Aza-bicyclo[3.2.1]oct-3-yl)-7-pyridin-4-yl-10H-phenoxazin-4-ol;
Endo-7-Pyridin-4-yl-10-(8-pyridin-2-ylmethyl-8-aza-bicyclo[3.2.1]oct-3-yl)-10H-phenoxazin-4-ol;
Endo-10-(8-Phenethyl-8-aza-bicyclo[3.2.1]oct-3-yl)-7-pyridin-4-yl-10H-phenoxazin-4-ol;
Endo-10-(8-Aza-bicyclo[3.2.1]oct-3-yl)-6-methoxy-3-pyridin-4-yl-10H-phenoxazine;
Endo-6-Methoxy-3-pyridin-4-yl-10-(8-pyridin-2-ylmethyl-8-aza-bicyclo[3.2.1]oct-3-yl)-10H-phenoxazine;
Endo-6-Methoxy-10-(8-phenethyl-8-aza-bicyclo[3.2.1]oct-3-yl)-3-pyridin-4-yl-10H-phenoxazine;
Endo-N-{2-[10-(8-Aza-bicyclo[3.2.1]oct-3-yl)-10H-phenoxazin-3-yl]-phenyl}-acetamide;

Endo-N-{2-[10-(8-Phenethyl-8-aza-bicyclo[3.2.1]oct-3-yl)-10H-phenoxazin-3-yl]-phenyl}-acetamide;
Endo-N-{2-[10-(8-Thiophen-2-ylmethyl-8-aza-bicyclo[3.2.1]oct-3-yl)-10H-phenoxazin-3-yl]-phenyl}-acetamide;
Endo-N-{2-[10-(8-Pyridin-2-ylmethyl-8-aza-bicyclo[3.2.1]oct-3-yl)-10H-phenoxazin-3-yl]-phenyl}-acetamide;
Exo-N-{2-[10-(8-Aza-bicyclo[3.2.1]oct-3-yl)-10H-phenoxazin-3-yl]-phenyl}-acetamide;
Endo-N-{2-[10-(8-Aza-bicyclo[3.2.1]oct-3-yl)-6-hydroxy-10H-phenoxazin-3-yl]-phenyl}-acetamide;
Endo-N-{2-[10-(8-Aza-bicyclo[3.2.1]oct-3-yl)-6-methoxy-10H-phenoxazin-3-yl]-phenyl}-acetamide;
10-(8-Phenethyl-8-aza-bicyclo[3.2.1]oct-3-yl)-3-(1H-tetrazol-5-yl)-10H-phenothiazine;
10-(8-Pyridin-2-ylmethyl-8-aza-bicyclo[3.2.1]oct-3-yl)-3-(1H-tetrazol-5-yl)-10H-phenothiazine;
10-(8-Aza-bicyclo[3.2.1]oct-3-yl)-3-(1H-tetrazol-5-yl)-10H-phenothiazine;
N,N-Diethyl-10-(8-phenethyl-8-aza-bicyclo[3.2.1]oct-3-yl)-10H-phenothiazine-3-carboxamidine;
N,N-Diethyl-10-(8-pyridin-2-ylmethyl-8-aza-bicyclo[3.2.1]oct-3-yl)-10H-phenothiazine-3-carboxamidine;
10-(8-Methyl-8-aza-bicyclo[3.2.1]oct-3-yl)-3-(1H-tetrazol-5-yl)-10H-phenothiazine;
N,N-Diethyl-10-(8-methyl-8-aza-bicyclo[3.2.1]oct-3-yl)-10H-phenothiazine-3-carboxamidine;
10-(8-Aza-bicyclo[3.2.1]oct-3-yl)-6-methoxy-3-pyridin-3-yl-10H-phenothiazine;
10-(8-Aza-bicyclo[3.2.1]oct-3-yl)-7-pyridin-3-yl-10H-phenothiazin-4-ol;
6-Methoxy-10-(8-methyl-8-aza-bicyclo[3.2.1]oct-3-yl)-10H-phenothiazine-3-carboxylic acid diethylamide;
10-(8-Aza-bicyclo[3.2.1]oct-3-yl)-6-methoxy-10H-phenothiazine-3-carboxylic acid diethylamide;
10-(8-Aza-bicyclo[3.2.1]oct-3-yl)-6-hydroxy-10H-phenothiazine-3-carboxylic acid diethylamide; and enantiomers, diastereomers, tautomers, solvates, or pharmaceutically acceptable salts thereof.

Another embodiment of the present invention is a composition comprising the dextrorotatory enantiomer of a compound of formula (I), wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

In certain embodiments, the present invention provides the endo isomer of a compound of formula (I) wherein said compound is substantially free from the exo isomer of said compound. In certain embodiments, the present invention provides compositions comprising the endo isomer of a compound of formula (I) wherein said composition is substantially free from the exo isomer of said compound. In the present context, substantially free means less than 25%, preferably less than 10%, more preferably less than 5%, even more preferably less than 2% and even more preferably less than 1% of the exo isomer.

In certain embodiments, the present invention provides the exo isomer of a compound of formula (I) wherein said compound is substantially free from the endo isomer of said compound. In certain embodiments, the present invention provides compositions comprising the exo isomer of a compound of formula (I) wherein said composition is substantially free from the endo isomer of said compound. In the present context, substantially free means less than 25%, preferably less than 10%, more preferably less than 5%, even more preferably less than 2% and even more preferably less than 1% of the endo isomer.

In other embodiments, compositions of the present invention comprise a mixture of the exo and endo isomers of a compound of formula (I).

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, 1997 (Jan), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to severe pain in warm-blooded animals such as humans by administration of an analgesically effective dose. The dosage range would be from about 0.1 mg to about 15,000 mg, in particular from about 50 mg to about 3500 mg or, more particularly from about 100 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the diseases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

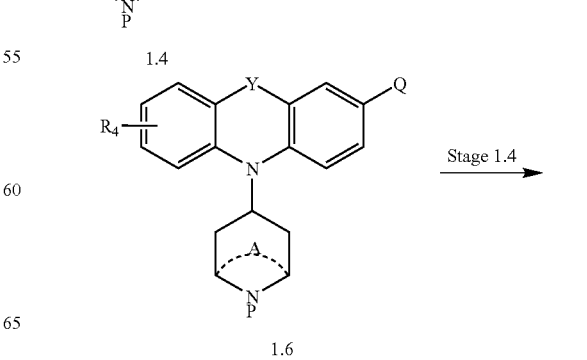

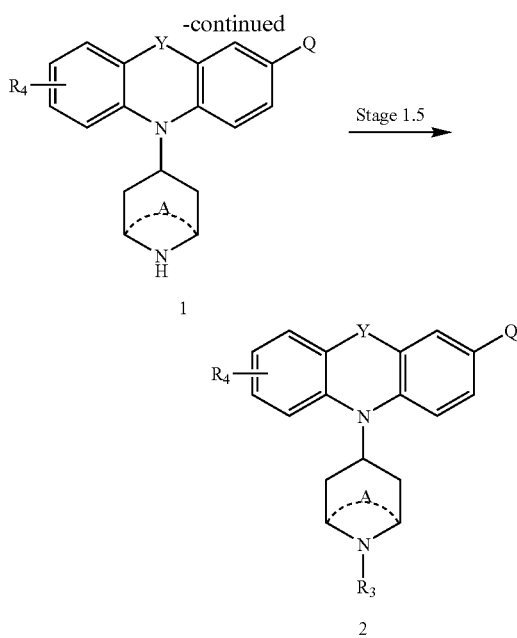

The preparation of compounds of this invention is illustrated in Schemes 1 through 11. The overall strategy in Scheme 1 is based on the synthesis of appropriately substituted compounds of formula 1.4 (Y =O, S) that are condensed with an appropriately substituted compound of formula 1.5. In compounds of formula 1.5, $X_2$ and $X_3$ can each be a halogen atom, trifluoromethanesulfonyloxy or a nitro group. In stage 1.1, a bridged N1-protected 4-aminopiperidine 1.1 is condensed with a properly substituted O-protected phenol (Y=O) or thiophenol (Y=S) 1.2. The protective group on the N1 nitrogen of 1.1 (represented as P) may include an alkanyl, alkenyl or aralkanyl group in which case they are the therapeutically useful products of this invention. The group P may also be trifluoromethylcarbonyl, alkoxycarbonyl or aralkoxycarbonyl. Bridge A may include $(CH_2)_2$ and $(CH_2)_3$. Useful phenol or thiophenol protective groups (R) include lower alkyl groups, benzyl, trialkylsilyl and the like. Appropriate substituents on the protected phenol or thiophenol in the 2-position ($X_1$) may include halogens and trifluoromethanesulfonyloxy. The Q group in the 5-position may be a substituent such as fluoro, chloro, bromo, cyano, iodo, carboxy, dialkylaminosulfonyl or trifluoromethanesulfonyloxy. Stage 1.2 includes deprotection of the phenol or thiophenol protective group. Such transformations may include the dealkylation of lower alkyl ethers to give their corresponding alcohols using reagents such as boron trihalides, or dealkylation of lower alkyl thioethers using reagents such as $Na/NH_3$. A benzyl protective group may be removed under conditions of hydrogenation in the presence of a transition metal such as palladium. Trialkylsilyl protective groups may be removed by treatment with a source of fluoride anion such as tetrabutyl ammonium fluoride, or by exposure to an inorganic acid such as aqueous hydrogen chloride and the like.

In stage 1.3, hydroxyaniline (Y=O) or thioaniline (Y=S) 1.4 may be condensed with an appropriately substituted benzene moiety 1.5. Substituents $X_2$ and $X_3$ may include halogens, trifluoromethanesulfonyloxy, or a nitro group. Useful coupling conditions of the anilino nitrogen with a compound of formula 1.5 include palladium catalyzed condensations in the presence of a phosphine ligand such as $Pd_2(dba)_3$ and a base such as cesium carbonate. Coupling of the hydroxy or thio moiety with the remaining substituted phenyl group may proceed using Ullmann type coupling conditions. In addition, the two steps described in stage 1.3 may be reversed with biaryl ether or biaryl thioether formation preceding the formation of the biaryl amine. Alternatively, the condensation between compounds of formula 1.4 and compounds of formula 1.5 to yield compounds of formula 1.6 in one step may be affected by treatment with an inorganic base such as potassium carbonate in a suitable solvent such as dimethyl formamide.

The regiochemical outcome of the condensation between compounds of formula 1.4 and compounds of formula 1.5 depends on the position of the R4 substituent in compounds of formula 1.5 and on the reaction conditions used for the condensation. An extensive review on this topic is available in the literature (see, for example: 'The Smiles and Related Rearrangements of aromatic Systems' by W. E. Truce, E. M. Kreider, and W. W. Brand in Organic Reactions, 1970, Vol. 18, pp. 99-215).

The protective group P can be removed to obtain secondary amines 1 as illustrated for Stage 1.4. These transformations may be carried out using certain acidic reagents such as hydrogen bromide or trimethylsilyl iodide. Phenoxazines (Y=O) or phenothiazines (Y=S) of type 1.6 bearing readily cleavable groups such as methyl, allyl or benzyl may be transformed into the aforementioned alkoxycarbonyl derivatives by treatment with alkanylchloroformates such as ethyl chloroformate or 1-chloroethyl chloroformate and thus serve as sources of phenoxazines and phenothiazines 1. Phenoxazines or phenothiazines of type 1.6 bearing a trifluormethylcarbonyl group may be treated with potassium carbonate in an alcoholic solvent such as methanol to yield phenoxazines and phenothiazines 1.

Finally the secondary amines 1 may be converted to a compound of formula 2 as shown in Stage 1.5. These transformations may be carried out by reductive alkylation using a carbonyl compound and a reducing agent such as sodium borohydride, sodium cyanoborohydride, sodium triacetoxyborohydride, or tetramethylammonium triacetoxyborohydride. They may also be carried out by alkylation using an alkanyl, alkenyl or aralkyl halide and an organic or inorganic base.

The Q function in compounds 1 or 2 may be converted into group G, which may be —C(Z)$NR_1R_2$, an aryl substituent, or an appropriate heterocycle as defined herein, to give compounds of formula 1. When the Q function is a halogen or trifluoromethanesulfonyloxy, it may be converted to an ester via alkoxycarbonylation using carbon monoxide, an aliphatic alcohol, a trialkanyl amine, and a palladium catalyst such as bis(triphenylphosphine) palladium(II)dichloride. Subsequently, when Q is an ester, the ester may be hydrolyzed to a carboxylic acid. The carboxylic acid may then be coupled with ammonia, a primary amine, or a secondary amine to form a primary, secondary or tertiary amide, respectively. Alternatively, the conversion of a carboxylic acid to an amide may be carried out via an acid chloride using thionyl chloride, oxalyl chloride, or the like, followed by a Schotten-Baumann reaction using ammonia or an amine in the presence of an alkali metal hydroxide. Alternatively, the conversion of a carboxylic acid to an amide may be carried out via the use of peptide coupling agents such as 1,3-dicyclohexylcarbondiimide (DCC), O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), or the like. Alternatively, the ester may be converted directly to the amide by the action of a dimethylaluminum amide.

Alternatively, when the Q function is a halogen or trifluoromethanesulfonyloxy, it may be converted directly to an amide via aminocarbonylation using a carbon monoxide source such as molybdenum hexacarbonyl, an appropriate amine, and a palladium catalyst such as Hermann's catalyst.

Alternatively, one may effect the transformation of the group Q to a substituent G (wherein G is an amidino or heterocycle) by way of a nitrile. Synthesis of the nitrile may be accomplished by treatment of the compounds 1 or 2 (when Q is bromo or trifluoromethanesulfonyloxy) with $Zn(CN)_2$ and a palladium catalyst such as $(Ph_3P)_4Pd$ or by treatment of the compounds 1 or 2 with CuCN at elevated temperatures. For the synthesis of amidino functional groups, the nitrile is treated with hydroxylamine under basic conditions to afford an oxime. Treatment of the oxime with a primary or secondary amine, CuCl, and an alkali metal carbonate under microwave irradiation in an alcoholic solvent provides the amidino compounds of the present invention. Microwave accelerated reactions may be performed using either a CEM Discover or a Personal Chemistry Smith Synthesizer microwave instrument. The oxime described above is instrumental in the preparation of compounds wherein G is a heterocycle. The oxime may be cyclized with a variety of electrophiles known to one versed in the art to give the heterocycles of the present invention. For instance, reaction of an oxime with CDI provides oxadiazolones, and treatment of the oxime with TCDI provides the corresponding oxadiazolethiones. Similarly, the treatment of the oxime with thionyl chloride in the presence of a tertiary amine gives oxathiadiazoles of the present invention.

Alternatively, compounds where Q is a halogen atom or a trifluoromethanesulfonyloxy group may participate in transition metal-mediated coupling reactions such as Suzuki, Stille or Negishi chemistry. Desired end products of the present invention may include chemical modifications at $R_4$. Such transformations may include the dealkylation of lower alkyl ethers to give the corresponding alcohols using reagents such as boron trihalides. Compounds where $R_4$ is a halogen atom may participate in transition metal-mediated coupling reactions such as Suzuki, Stille or Negishi chemistry.

Scheme 2

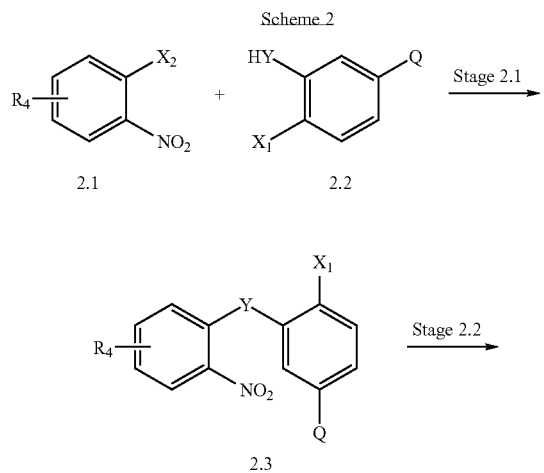

-continued

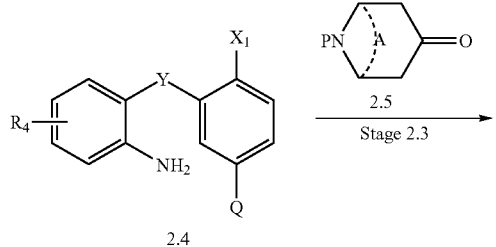

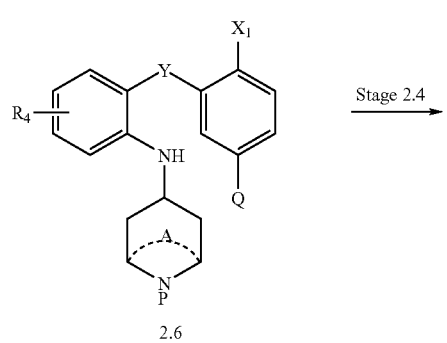

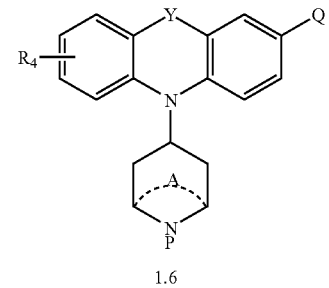

Scheme 2 outlines an alternative approach to the synthesis of phenoxazines (Y=O) or phenothiazines (Y=S) 1.6. In this scheme, an appropriately substituted phenol (Y=O) or thiophenol (Y=S) of type 2.2 is reacted with an appropriately substituted benzene moiety 2.1 in the presence of a base, such as potassium carbonate or sodium hydroxide in an organic solvent, such as dimethyl formamide, dimethyl acetamide, dimethyl sulfoxide or the like as shown in stage 2.1. Appropriate substituents $X_1$ and $X_2$ in this scheme may include halogens and trifluoromethanesulfonyloxy. In stage 2.2, the nitro functionality is reduced to the corresponding amine. This reduction can be accomplished via treatment with tin(II) chloride in an alcoholic solvent such as ethanol. Stage 2.3 depicts the conversion of primary aniline 2.4 to secondary aniline 2.6, which can be accomplished via reductive alkylation using a carbonyl compound 2.5 and a reducing agent such as sodium borohydride, sodium cyanoborohydride, sodium triacetoxyborohydride, or tetramethylammonium triacetoxyborohydride. Stage 2.4 depicts formation of compounds of formula 1.6, which can be accomplished by treatment of secondary aniline 2.6 with an appropriate base such as potassium carbonate.

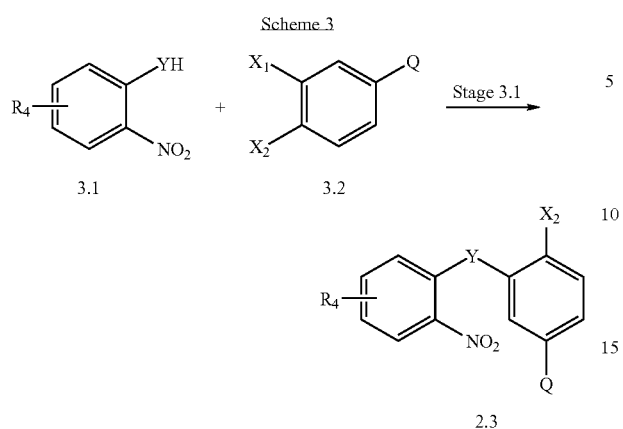

Scheme 3 illustrates an alternative synthesis of compound 2.3. In this approach, an appropriately substituted 2-nitrophenol (Y=O) or 2-nitrothiophenol (Y=S) may be condensed with an appropriately substituted benzene moiety of type 3.2 under Ullmann type coupling conditions. Appropriate substituents $X_1$ and $X_2$ include halogens and trifluoromethanesulfonyloxy.

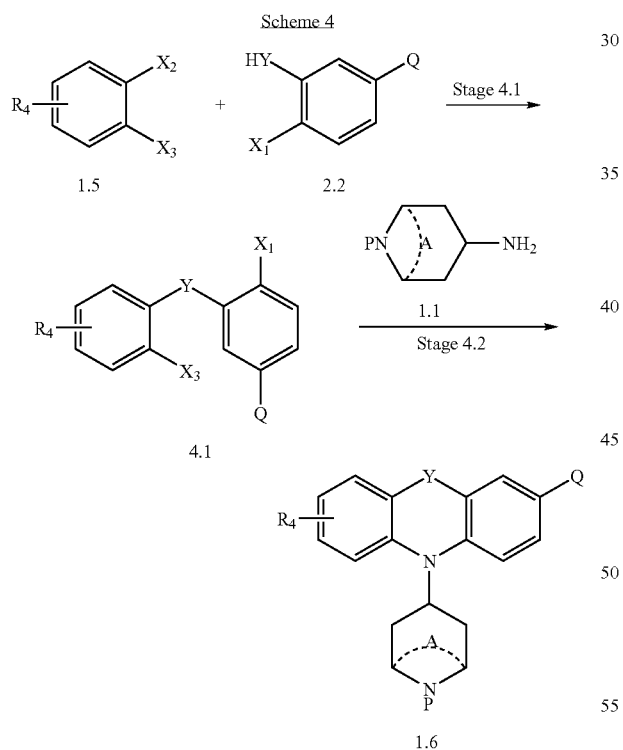

Scheme 4 illustrates an alternative approach to the synthesis of phenoxazines (Y=O) or phenothiazines (Y=S) 1.6. Condensation of appropriately substituted phenols (Y=O) or thiophenols (Y=S) 2.2 with substituted benzene moiety 1.5 under Ullmann type coupling conditions as shown in stage 4.1 may result in the formation of biaryl ethers (Y=O) or biaryl thioethers (Y=S) 4.1. Appropriate $X_1$, $X_2$ and $X_3$ substituents may include halogens and trifluoromethanesulfonyloxy. Palladium catalyzed condensation of biaryl ethers or biaryl thioethers 4.1 with bridged N1-protected 4-aminopiperidines 1.1 in the presence of a phosphine ligand such as $Pd_2(dba)_3$ and a base such as cesium carbonate is shown in stage 4.2 may result in the formation of phenoxazines or phenothiazines 1.6.

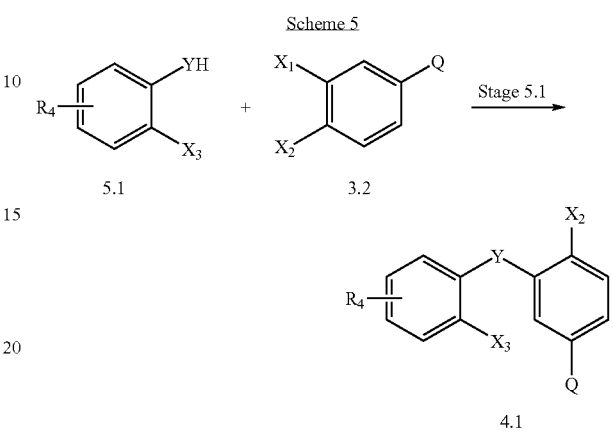

An alternative approach to the synthesis of intermediate 4.1 is depicted in Scheme 5 and is based on the reaction of appropriately substituted phenols (Y=O) or thiophenols (Y=S) 5.1 with an appropriately substituted benzene moiety 3.2 under Ullmann type coupling conditions (stage 5.1). Substituents $X_1$, $X_2$, and $X_3$ may include halogens or trifluoromethanesulfonyloxy.

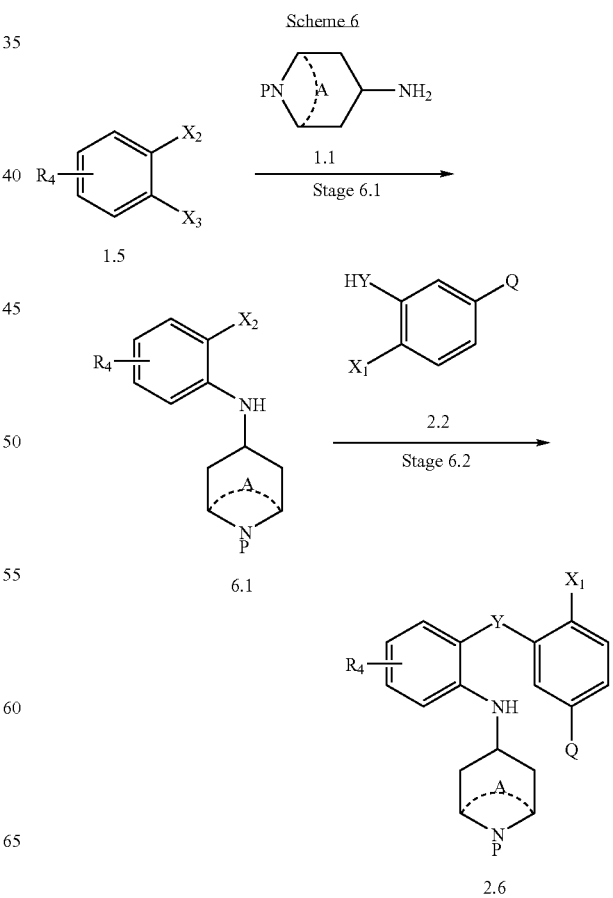

Scheme 6 illustrates an alternative approach to the synthesis of intermediates 2.6. An appropriately substituted compound of formula 1.5 may be reacted with bridged N1-protected 4-aminopiperidines 1.1 in the presence of a palladium catalyst such as $Pd_2(dba)_3$, a phosphine ligand and a base such as cesium carbonate as shown in stage 6.1. Appropriate $X_1$ and $X_2$ substituents may include halogens and trifluoromethanesulfonyloxy. Compounds of formula 6.1 may then be reacted with appropriately substituted phenols (Y=O) or thiophenols (Y=S) 2.2 under Ullmann type coupling conditions to yield anilines 2.6 as shown in stage 6.2.

tions may result in formation of compounds 7.3 as shown in stage 7.2. Finally, ring closure of compounds 7.4 may be accomplished in the presence of a palladium catalyst such as $Pd_2(dba)_3$, a phosphine ligand such as 4,5-bis(diphenylphosphino)-9,9-dimethylxanthene (xant phos) and a base such as potassium tert-butoxide or cesium carbonate as shown in stage 7.3.

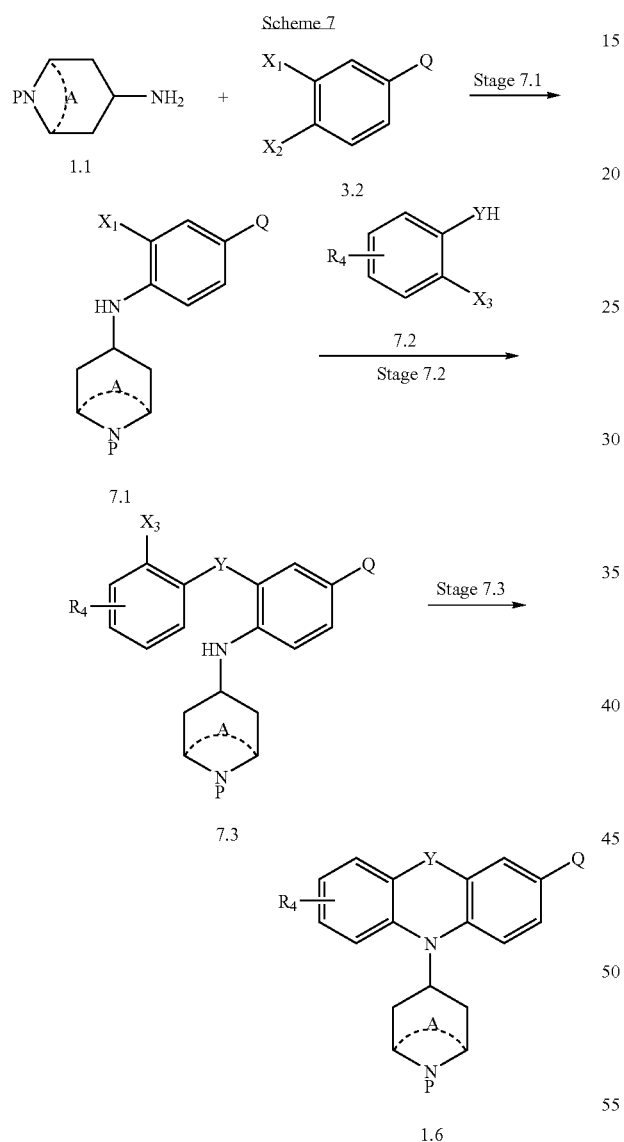

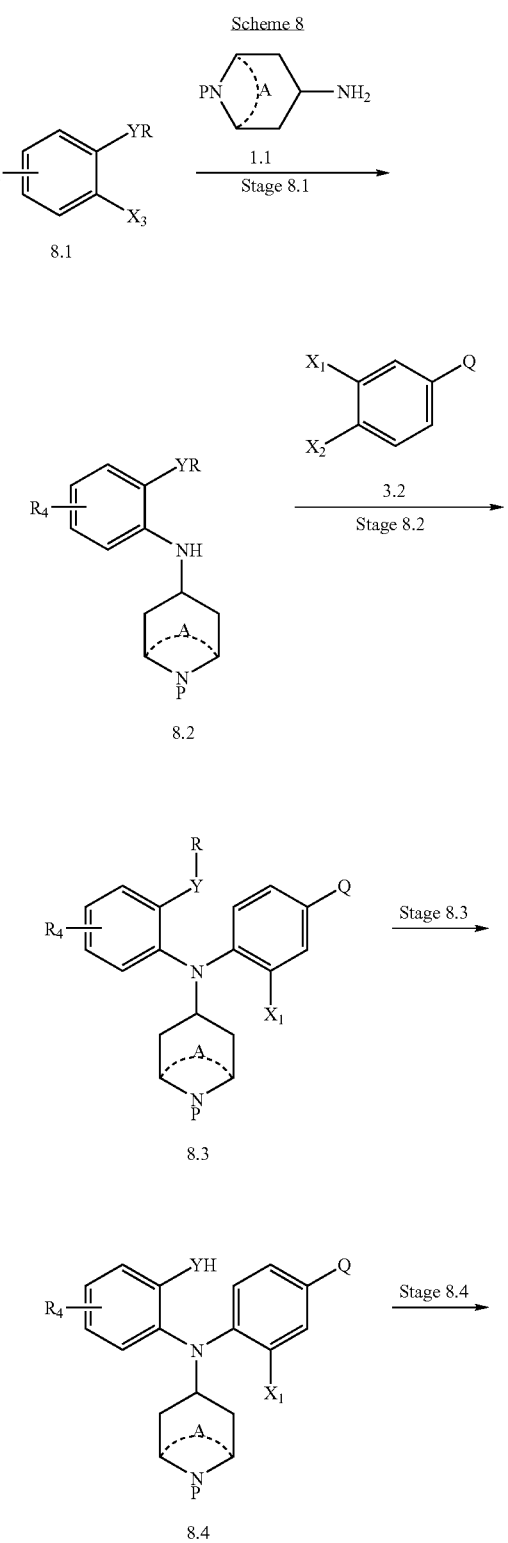

Scheme 7 illustrates an alternative approach to the synthesis of phenoxazines (Y=O) or phenothiazines (Y=S) 1.6. Condensation of appropriately substituted compounds of formula 3.2 with bridged N1-protected 4-aminopiperidines 1.1 may result in formation of intermediate 7.1 as shown in stage 7.1. Appropriate $X_1$, $X_2$, and $X_3$ substituents may include halogens and trifluoromethanesulfonyloxy. Reaction of compounds 7.1 with appropriately substituted phenol (Y=O) or thiophenols (Y=S) 7.2 under Ullmann like coupling condi- -continued

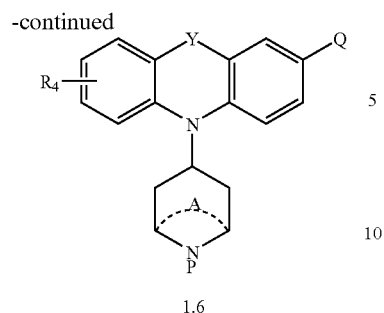

1.6

Scheme 8 illustrates an alternative synthesis of phenoxazines (Y=O) or phenothiazines (Y=S) 1.6 and is based on an Ullmann-like coupling of bridged N1-protected 4-aminopiperidines 1.1 with appropriately substituted and protected phenols (Y=O) or thiophenols (Y=S) 8.1 as shown in stage 8.1. Useful phenol or thiophenol protective groups for compounds 8.1 include lower alkyl groups, benzyl, trialkylsilyl and the like. Appropriate $X_1$, $X_2$, and $X_3$ substituents may include halogens and trifluoromethanesulfonyloxy. The resulting compounds 8.2 may be condensed with appropriately functionalized benzene compounds 3.2 to yield diarylanilines 8.3. Stage 8.3 includes deprotection of the phenol or thiophenol protective group. Such transformations may include the dealkylation of lower alkyl ethers to give their corresponding alcohols using reagents such as boron trihalides or the dealkylation of the alkyl thioethers using Na/$NH_3$. A benzyl protective group may be removed under conditions of hydrogenation in the presence of a transition metal such as palladium. Trialkylsilyl protective groups may be removed by treatment with a source of fluoride anion such as tetrabutyl ammonium fluoride, or by exposure to an inorganic acid such as aqueous hydrogen chloride and the like. Finally, ring closure of compounds 8.3 to phenoxazines or phenothiazines 1.6 may be accomplished via an Ullmann type transformation as shown in stage 8.4.

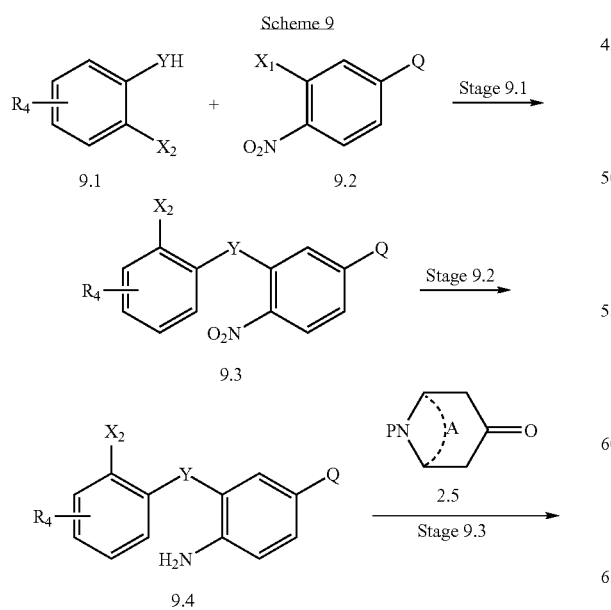

-continued

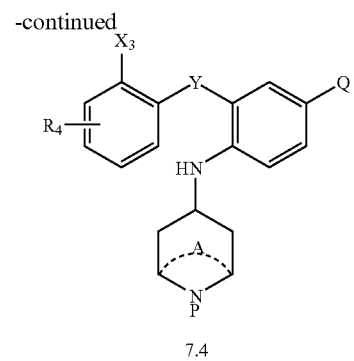

7.4

Scheme 9 illustrates another synthetic approach to compounds 7.4. Displacement of $X_1$ in appropriately substituted compounds of formula 9.2 with appropriately substituted compounds of formula 9.1 as shown in stage 9.1 may lead to biaryl ethers (Y=O) and biarylthioethers (Y=S) 9.3. Appropriate $X_1$ and $X_2$ substituents may include halogens and trifluoromethanesulfonyloxy. Reduction of compounds 9.3 to amines 9.4 as shown in stage 9.2 may be accomplished using tin(II) chloride in an alcoholic solvent such as ethanol. Stage 9.3 depicts the conversion of primary anilines 9.4 to secondary anilines 7.4 and can be accomplished via reductive alkylation using a carbonyl compounds 2.5 and a reducing agent such as sodium borohydride, sodium cyanoborohydride, sodium triacetoxyborohydride, or tetramethylammonium triacetoxyborohydride.

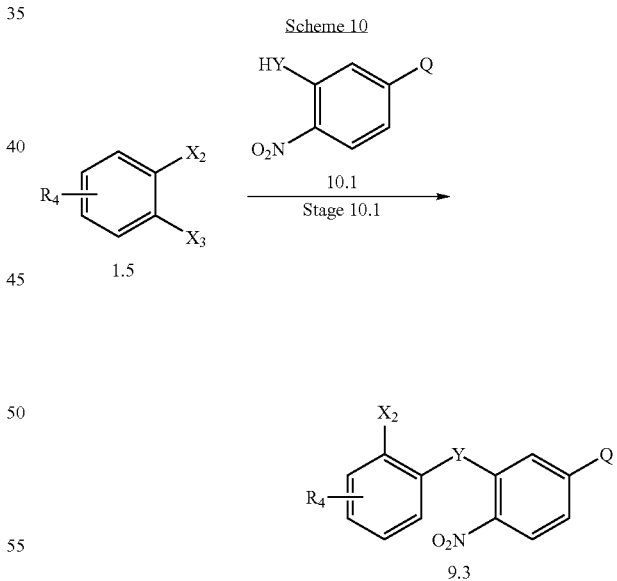

Scheme 10 illustrates another synthetic approach to compounds 9.3. For construction of diaryl ethers (Y=O) and diaryl thioethers (Y=S) 9.3, appropriately substituted 2-hydroxynitrobenzenes or 2-thionitrobenzenes 10.1 may be caused to react with appropriately substituted compounds of formula 1.5 under Ullmann type conditions as shown in stage 10.1. Appropriate $X_2$ and $X_3$ substituents may include halogens and trifluoromethanesulfonyloxy.

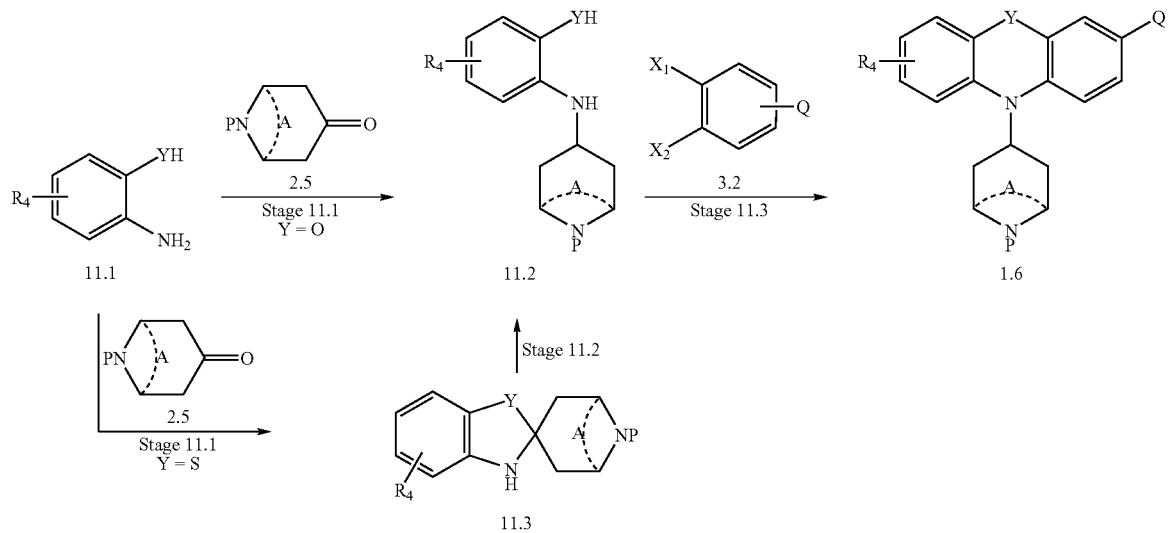

Scheme 11

Scheme 11 illustrates another synthetic approach to compounds 1.6. Stage 11.1 depicts the conversion of appropriately substituted 2-hydroxyanilines (Y═O) 11.1 to compounds 11.2 (Y═O), which can be accomplished via reductive alkylation using a carbonyl compound 2.5 and a reducing agent such as sodium borohydride, sodium cyanoborohydride, sodium triacetoxyborohydride, or tetramethylammonium triacetoxyborohydride. Appropriately substituted 2-hydroxyanilines 11.2 may be caused to react with an appropriately substituted benzene 3.2 under Ullmann type conditions or under basic conditions such as potassium carbonate in DMF (when $X_1$═$NO_2$) as shown in stage 11.3 to yield compounds of formula 1.6. Appropriate $X_1$ and $X_2$ substituents may include halogens, trifluoromethanesulfonyloxy, and a nitro group.

The regiochemical outcome of the condensation of compounds of formula 11.2 with compounds of formula 3.2 depends on the position of the Q substituent in compounds of formula 3.2 and on the reaction conditions used for the condensation. An extensive review on this topic is available in the literature (see, for eample: 'The Smiles and Related Rearrangements of aromatic Systems' by W. E. Truce, E. M. Kreider, and W. W. Brand in Organic Reactions, 1970, Vol. 18, pp. 99-215).

In compounds of formula 11.1 where Y is sulfur, an intermediate spiro compound of formula 11.3 may be formed. Compounds of formula 11.3 may be converted to compounds of formula 11.2 (Y═S) by treatment with a hydride reagent such as lithium aluminum hydride or sodium borohydride.

In the above Schemes 1 through 11, the Q function of compounds 2 may be converted into group G, which may be —C(Z)$NR_1R_2$, an aryl substituent, or an appropriate heterocycle as defined herein, to give compounds of formula 3. When the Q function of compounds 2 is a halogen or trifluoromethanesulfonyloxy, it may be converted to an ester via alkoxycarbonylation using carbon monoxide, an aliphatic alcohol, a trialkanyl amine, and a palladium catalyst such as bis(triphenylphosphine) palladium(II) dichloride. Subsequently, when Q is an ester, the ester may be hydrolyzed to a carboxylic acid. The carboxylic acid may then be coupled with ammonia, a primary amine, or a secondary amine to form a primary, secondary or tertiary amide, respectively. Alternatively, the conversion of a carboxylic acid to an amide may be carried out via an acid chloride using thionyl chloride, oxalyl chloride, or the like, followed by a Schotten-Baumann reaction using ammonia or an amine in the presence of an alkali metal hydroxide. Alternatively, the conversion of a carboxylic acid to an amide may be carried out via the use of peptide coupling agents such as 1,3-dicyclohexylcarbondiimide (DCC), O-(7-azabenzotriazol-1-yl)-N,N,N',N'-tetramethyluronium hexafluorophosphate (HATU), O-benzotriazol-1-yl -N,N,N',N'-tetramethyluronium hexafluorophosphate (HBTU), or the like. Alternatively, the ester may be converted directly to the amide by the action of a dimethylaluminum amide.

Instead of proceeding to compounds 3 via an ester, one may effect the transformation of the group Q to a substituent G (wherein G is an amidino or heterocycle) by way of a nitrile. Synthesis of the nitrile may be accomplished by treatment of the compounds 2 (when Q is bromo or trifluoromethanesulfonyloxy) with $Zn(CN)_2$ and a palladium catalyst such as $(Ph_3P)_4Pd$ or by treatment of the compounds 2 with CuCN at elevated temperatures. For the synthesis of amidino functional groups, the nitrile is treated with hydroxylamine under basic conditions to afford an oxime. Treatment of the oxime with a primary or secondary amine, CuCl, and an alkali metal carbonate under microwave irradiation in an alcoholic solvent provides the amidino compounds of the present invention. Microwave accelerated reactions may be performed using either a CEM Discover or a Personal Chemistry Smith Synthesizer microwave instrument. The oxime described above is instrumental in the preparation of compounds wherein G is a heterocycle. The oxime may be cyclized with a variety of electrophiles known to one versed in the art to give the heterocycles of the present invention. For instance, reaction of an oxime with CDI provides oxadiazolones, and treatment of the oxime with TCDI provides the corresponding oxadiazolethiones. Similarly, the treatment of the oxime with thionyl chloride in the presence of a tertiary amine gives oxathiadiazoles of the present invention.

An aryl substituent may be installed in place of the functional group Q by coupling compounds 2 (when Q is bromo or trifluoromethanesulfonyloxy) with a suitably substituted arylboronic acid in the presence of a palladium catalyst and an alkali metal carbonate.

Desired end products of the present invention may include chemical modifications at $R_4$. Such transformations may include the dealkylation of lower alkyl ethers to give their corresponding alcohols, using reagents such as boron trihalides. Compounds where $R_4$ is a halogen atom may participate in transition metal-mediated coupling reactions such as Suzuki, Stille or Negishi chemistry.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., J. Org. Chem. 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Abbreviations
AcOH=acetic acid
Boc=tert-butoxycarbonyl
DIEA=N,N-diisopropyl-N-ethylamine
DMF=N,N-dimethylformamide
DMSO=dimethyl sulfoxide
Et=ethyl
h=hour(s)
HBTU=O-benzotriazol-1-yl-N,N,N',N'-tetramethyluronium hexafluorophosphate
$K_2CO_3$=potassium carbonate
Me=methyl
min=minute(s)
rt=room temperature
xantphos=4,5-bis(diphenylphosphino)-9,9-dimethylxanthene Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

EXAMPLES

Example A

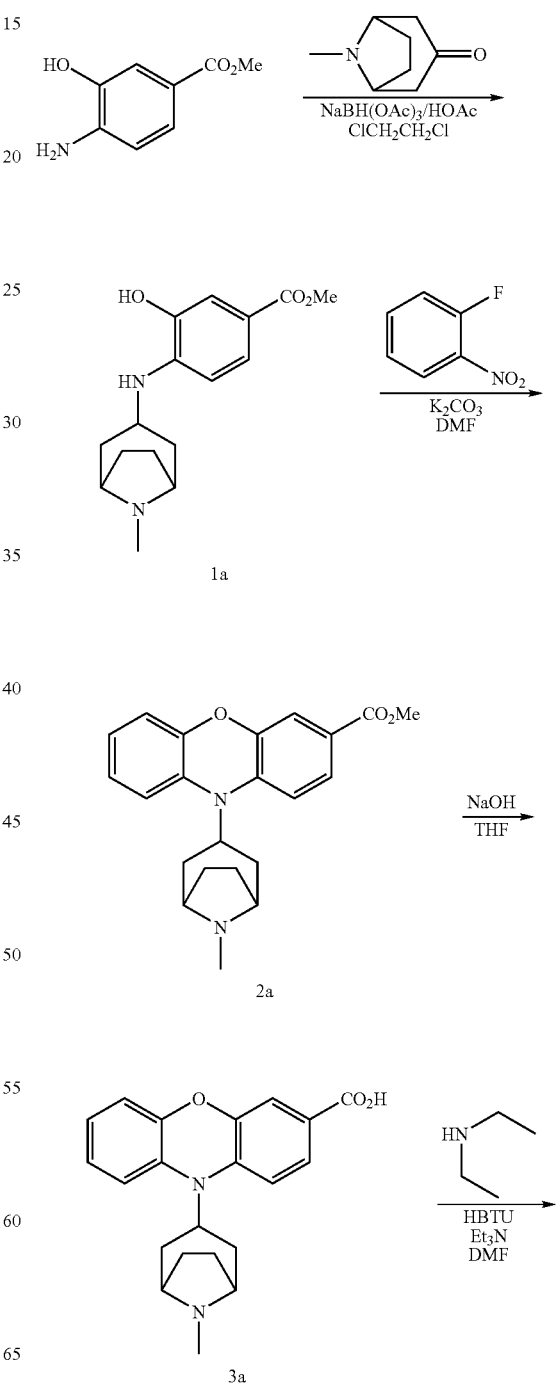

-continued

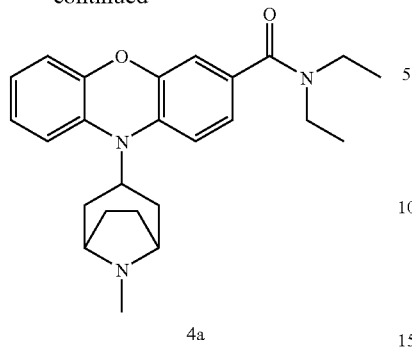

4a

Procedure 1

3-Hydroxy-4-(8-methyl-8-aza-bicyclo[3.2.1]oct-3-ylamino)-benzoic acid methyl ester, 1a To a solution of 4-amino-3-hydroxybenzoic acid methyl ester (2.0 g; 12 mmol) and 8-methyl-8-aza-bicyclo[3.2.1]octan-3-one (1.1 g; 10.8 mmol) in dichloroethane (30 mL) was added sodium triacetoxyborohydride (3.2 g; 15.1 mmol) and acetic acid (0.65 mL; 11.4 mmol). The mixture was stirred at rt for 16 h. The mixture was diluted with 1N NaHCO₃ solution and chloroform was added. The organic layer separated, and the aqueous phase was lyophilized. The lyophilized residue was purified via reverse phase HPLC (eluent gradient: 10 to 50% acetonitrile in water containing 0.1% TFA) to yield 1.61 g (36.9%) of a mixture of endo and exo isomers of 3-hydroxy-4-(8-methyl-8-aza-bicyclo [3.2.1] oct-3-ylamino)-benzoic acid methyl ester, 1a as a TFA salt. MS m/z (MH⁺) 291.

Procedure 2

10-(8-Methyl-8-aza-bicyclo[3.2.1]oct-3-yl)-10H-phenoxazine-3-carboxylic acid methyl ester, 2a A mixture of the TFA salt of 3-hydroxy-4-(8-methyl-8-aza-bicyclo[3.2.1]oct-3-ylamino)-benzoic acid methyl ester, 1a (0.424 g, 0.734 mmol), 2-fluoronitrobenzene (95 μL, 0.9 mmol) and potassium carbonate (564 mg, 4 mmol) in DMF was heated to reflux for 70 min. The mixture was allowed to cool to rt, filtered, and purified via reverse phase HPLC to yield 440 mg (88%) of 10-(8-methyl-8-aza-bicyclo[3.2.1]oct-3-yl)-10H-phenoxazine-3-carboxylic acid methyl ester, 2a, as TFA salt. MS m/z (MH⁺) 365.1.

Procedure 3

10-(8-Methyl-8-aza-bicyclo[3.2.1]oct-3-yl)-10H-phenoxazine-3-carboxylic acid, 3a To a solution of 10-(8-methyl-8-aza-bicyclo[3.2.1]oct-3-yl)-10H-phenoxazine-3-carboxylic acid methyl ester, 2a (440 mg, 0.646 mmol) in THF (5 mL) was added 1N NaOH (5 mL), and the mixture was stirred for 3 hr at rt. The solvent was removed, the residue was dissolved in DMF and acidified with a 2N TFA solution, and purified via reverse phase HPLC to yield 295 mg (63%) of 10-(8-methyl-8-aza-bicyclo[3.2.1]oct-3-yl)-10H-phenoxazine-3-carboxylic acid, 3a, as a TFA salt. MS m/z (MH⁺) 351.1.

Procedure 4

10-(8-Methyl-8-aza-bicyclo[3.2.1]oct-3-yl)-10H-phenoxazine-3-carboxylic acid diethylamide, 4a To a solution of the TFA salt of 10-(8-methyl-8-aza-bicyclo[3.2.1]oct-3-yl)-10H-phenoxazine-3-carboxylic acid 3a (65 mg, 0.14 mmol) and HBTU (64 mg; 0.17 mmol) in DMF (2 mL) was added triethylamine (69 μL, 0.43 mmol). The mixture was stirred for 1 hr at rt, and purified without prior quenching via reverse phase HPLC (eluent gradient: acetonitrile in water containing 0.1% TFA) to yield 44.4 mg (61%) of title compound 10-(8-methyl-8-aza-bicyclo[3.2.1]oct-3-yl)-10H-phenoxazine-3-carboxylic acid diethylamide, 4a as a TFA salt. MS m/z (MH⁺) 406.2.

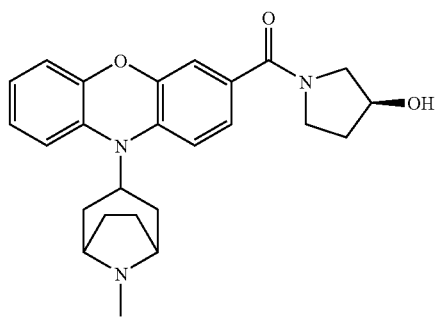

5a

(3-Hydroxy-pyrrolidin-1-yl)-[10-(8-methyl-8-aza-bicyclo[3.2.1]oct-3-yl)-10H-phenoxazin-3-yl]-methanone, 5a Using an adaptation of Procedure 4, and substituting 3-hydroxypyrrolidine for diethylamine, the title compound (3-hydroxy-pyrrolidin-1-yl)-[10-(8-methyl-8-aza-bicyclo[3.2.1]oct-3-yl)-10H-phenoxazin-3-yl]-methanone, 5a was obtained as a TFA salt. MS m/z (MH⁺) 420.1.

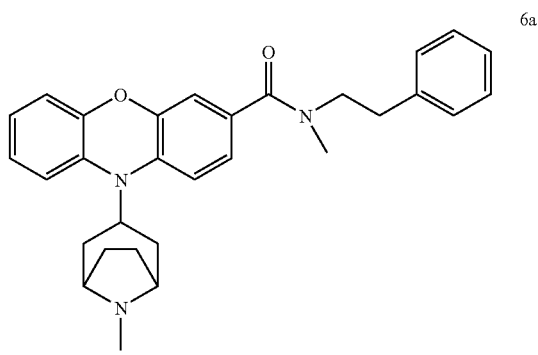

6a

10-(8-Methyl-8-aza-bicyclo[3.2.1]oct-3-yl)-10H-phenoxazine-3-carboxylic acid methyl-phenethyl-amide, Using an adaptation of Procedure 4, and substituting N-methyl-N-phenethylamine for diethylamine, the title compound 10-(8-methyl-8-aza-bicyclo[3.2.1]oct-3-yl)-10H- phenoxazine-3-carboxylic acid methyl-phenethyl-amide, 6a was obtained as a TFA salt. MS m/z (MH+) 468.3.

Example B

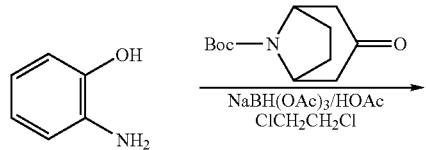

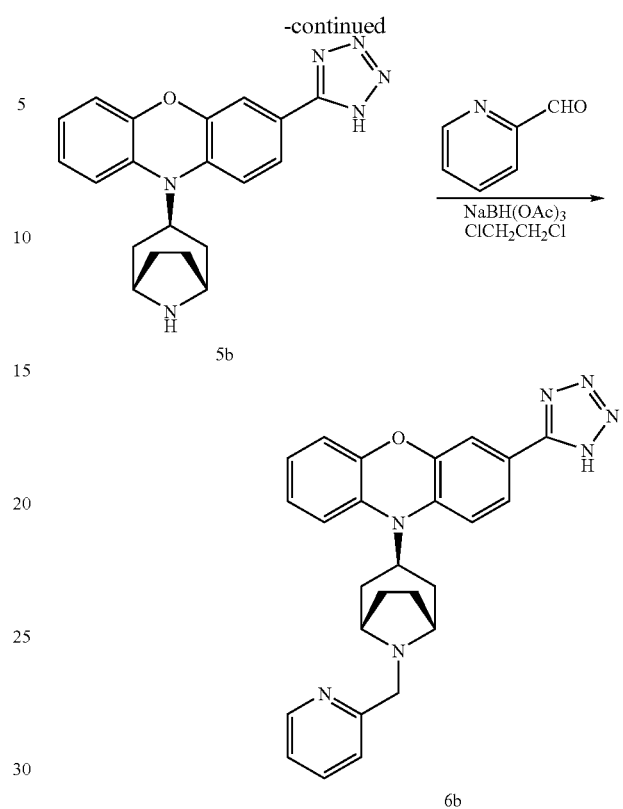

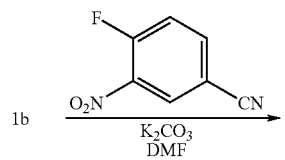

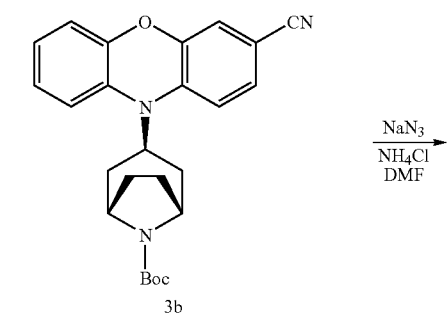

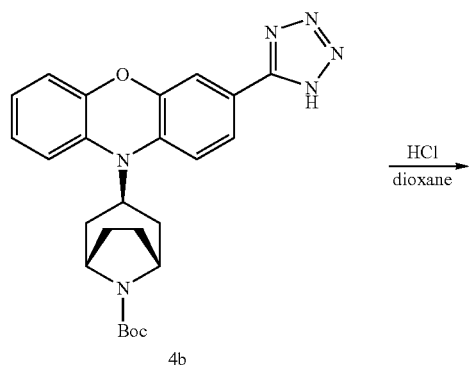

Procedure 5

Endo-3-(2-Hydroxy-phenylamino)-8-aza-bicyclo[3.2.1]octane-8-carboxylic acid tert-butyl ester, 1b and Exo-3-(2-Hydroxy-phenylamino)-8-aza-bicyclo[3.2.1]octane-8-carboxylic acid tert-butyl ester, 2b To a solution of 2-aminophenol (5.0 g; 45.82 mmol) and 3-oxo-8-aza-bicyclo[3.2.1]octane-8-carboxylic acid tert-butyl ester (15.5 g; 68.8 mmol) in dichloroethane (200 mL) was added acetic acid (2.62 mL; 45.77 mmol). The mixture was stirred at rt for 1 h and sodium triacetoxyborohydride (11.6 g; 54.73 mmol) was added in small portions. The mixture was stirred at rt for 16 h and treated with H₂O (200 mL). The organic layer was separated, dried over MgSO₄, filtered, and evaporated. The residue was purified via column chromatography (eluent gradient: 10 to 30% ethyl acetate in heptane) to yield 8 g (55%) of endo-3-(2-hydroxy-phenylamino)-8-aza-bicyclo[3.2.1]octane-8-carboxylic acid tert-butyl ester, 1b and 1.5 g (10%) of exo-3-(2-hydroxy-phenylamino)-8-aza-bicyclo[3.2.1]octane-8-carboxylic acid tert-butyl ester, 1b. MS m/z (MH+) 318.9.

Procedure 6

Endo-3-(3-Cyano-phenoxazin-10-yl)-8-aza-bicyclo[3.2.1]octane-8-carboxylic acid tert-butyl ester, 3b To a solution of 4-fluoro-3-nitrobenzonitrile (0.29 g; 1.74 mmol) and endo-3-(2-hydroxy-phenylamino)-8-aza-bicyclo[3.2.1]octane-8-carboxylic acid tert-butyl ester, 1b (0.55 g; 1.73 mmol) in DMF (6 mL) was added potassium carbonate (0.48 g; 3.47 mmol). The mixture was stirred at 170° C. for 30 min. The mixture was allowed to cool to rt and poured into ice-water 910 mL). The solid was separated via filtration, washed with water, and dried to yield 0.63 g (86%) of endo-3-(3-cyano-phenoxazin-10-yl)-8-aza-bicyclo[3.2.1]octane-8-carboxylic acid tert-butyl ester, 3b. MS m/z (MH$^+$) 417.9. The material was used as such for the next reaction.

Procedure 7

Endo-3-[3-(1H-Tetrazol-5-yl)-phenoxazin-10-yl]-8-aza-bicyclo[3.2.1]octane-8-carboxylic acid tert-butyl ester, 4b To a solution of endo-3-(3-cyano-phenoxazin-10-yl)-8-aza-bicyclo[3.2.1]octane-8-carboxylic acid tert-butyl ester, 3b (1 g; 2.4 mmol) in DMF (20 mL) were added sodium azide (0.47 g, 7.23 mmol) and ammonium chloride (0.39 g; 7.29 mmol), and the mixture was heated at 120° C. for 16 h. The mixture was allowed to cool to rt, and filtered. The filtrate was acidified with 1N hydrochloric acid (10 mL) and extracted with ethyl acetate (3×10 mL). The combined organic layers were dried over MgSO$_4$, filtered, and evaporated. The residue was used as such for the next reaction.

Procedure 8

Endo-10-(8-Aza-bicyclo[3.2.1]oct-3-yl)-3-(1H-tetrazol-5-yl)-10H-phenoxazine, 5b

To a solution of endo-3-[3-(1H-tetrazol-5-yl)-phenoxazin-10-yl]-8-aza-bicyclo[3.2.1]-octane-8-carboxylic acid tert-butyl ester, 4b (2.4 mmol) in dioxane (5 mL) was added a 4N hydrochloric acid solution (5 mL). The mixture was stirred at rt for 16 h. The mixture was filtered, and the filtrate was evaporated. The residue was purified via reverse phase chromatography (eluent gradient: acetonitrile in water containing 0.1% TFA) to yield crudeendo-10-(8-aza-bicyclo[3.2.1]oct-3-yl)-3-(1H-tetrazol-5-yl)-10H-phenoxazine, 5b as a TFA salt. MS m/z (MH$^+$) 360.9. The material was used as such in the next reaction.

Procedure 9

Endo-10-(8-Pyridin-2-ylmethyl-8-aza-bicyclo[3.2.1]oct-3-yl)-3-(1H-tetrazol-5-yl)-10H-phenoxazine, 6b To a suspension of the HCl salt of endo-10-(8-aza-bicyclo[3.2.1]oct-3-yl)-3-(1H-tetrazol-5-yl)-10H-phenoxazine, 5b (0.2 g; 0.5 mmol) and 2-pyridylcarboxaldehyde (0.071 mL; 0.74 mmol) in dichloroethane (4 mL) was added sodium triacetoxyborohydride (0.13 g; 0.61 mmol). The mixture was stirred at rt for 15 h and a saturated NaHCO$_3$ solution (3 mL). The organic layer was separated, and the aqueous phase was extracted with ethyl acetate (5 mL). The combined organic layers were dried over MgSO$_4$, filtered, and evaporated. The residue was purified via reverse phase HPLC (eluent: acetonitrile in water containing 0.1% TFA) to yield 139.8 mg (quant.) of title compound endo-10-(8-pyridin-2-ylmethyl-8-aza-bicyclo[3.2.1]oct-3-yl)-3-(1H-tetrazol-5-yl)-10H-phenoxazine, 6b as a TFA salt. MS m/z (MH$^+$) 452.0.

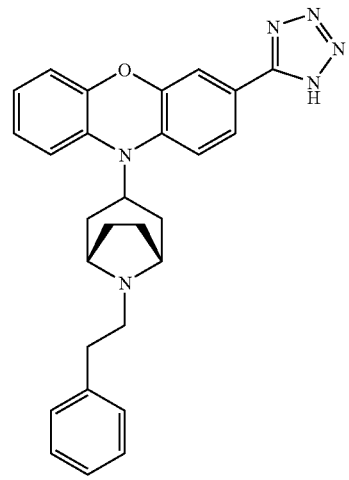

Endo-10-(8-Phenethyl-8-aza-bicyclo[3.2.1]oct-3-yl)-3-(1H-tetrazol-5-yl)-10H-phenoxazine, 7b Using an adaptation of Procedure 9, and substituting phenylacetaldehyde for 2-pyridyl carboxaldehyde, the title compound endo-10-(8-phenethyl-8-aza-bicyclo[3.2.1]oct-3-yl)-3-(1H-tetrazol-5-yl)-10H-phenoxazine, 7b was obtained as a TFA salt. MS m/z (MH$^+$) 464.9.

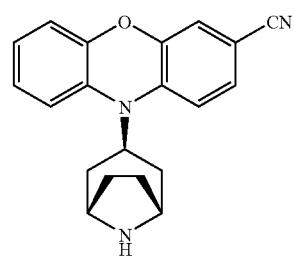

Endo-10-(8-Aza-bicyclo[3.2.1]oct-3-yl)-10H-phenoxazine-3-carbonitrile, 8b

Using an adaptation of Procedure 9, and substituting endo-3-(3-cyano-phenoxazin-10-yl)-8-aza-bicyclo[3.2.1]octane-8-carboxylic acid tert-butyl ester, 3b for endo-3-[3-(1H-tetrazol-5-yl)-phenoxazin-10-yl]-8-aza-bicyclo[3.2.1]-octane-8-carboxylic acid tert-butyl ester, 4b, the title compound endo-10-(8-aza-bicyclo[3.2.1]oct-3-yl)-10H-phenoxazine-3-carbonitrile, 8b was obtained as a TFA salt. MS m/z (MH⁺) 317.9.

Example C

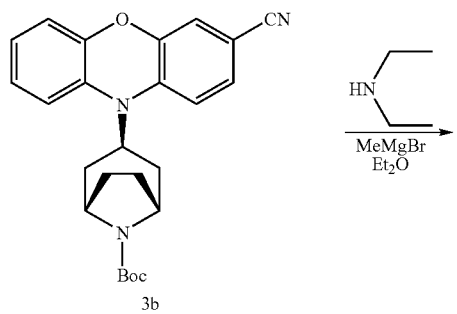

3b

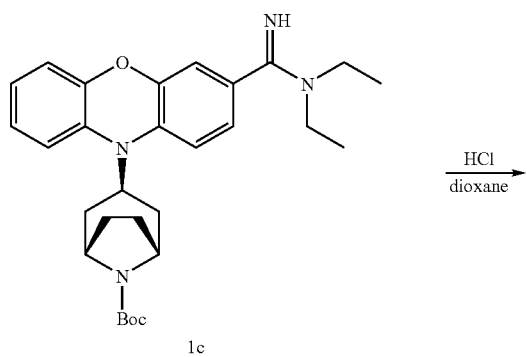

1c

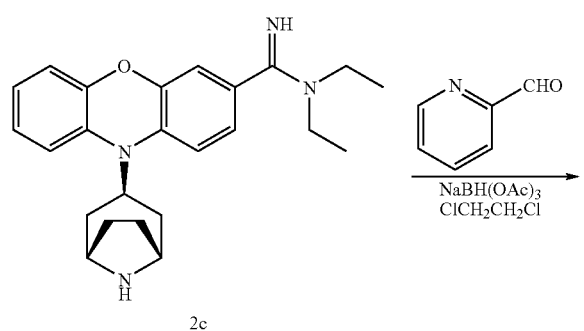

2c

Procedure 10

Endo-3-[3-(N,N-Diethyl-carbamimidoyl)-phenoxazin-10-yl]-8-aza-bicyclo[3.2.1]-octane-8-carboxylic acid tert-butyl ester, 1c To a solution of methylmagnesium bromide in diethyl ether (3.0 M, 2.4 mL, 7.2 mmol) under nitrogen was added dropwise a solution of diethylamine (0.749 mL, 7.19 mmol) in diethyl ether (2 mL). The mixture was heated to reflux for 30 min, cooled to rt, and a suspension of endo-3-(3-cyano-phenoxazin-10-yl)-8-aza-bicyclo[3.2.1]octane-8-carboxylic acid tert-butyl ester, 3b (1.0 g, 2.4 mmol) was added. The mixture was stirred at 40° C. for 2 hr and water (10 mL) was added. The organic layer was separated, and the aqueous layer was further extracted with chloroform (2×10 mL). The combined organic layers were dried over magnesium sulfate, filtered, and evaporated, yielding title compound endo-3-[3-(N,N-diethyl-carbamimidoyl)-phenoxazin-10-yl]-8-aza-bicyclo[3.2.1]-octane-8-carboxylic acid tert-butyl ester 1c. MS m/z (MH⁺) 491.0. The residue was used as such for the next reaction.

Endo-10-(8-Aza-bicyclo[3.2.1]oct-3-yl)-N,N-diethyl-10H-phenoxazine-3-carboxamidine, 2c Using an adaptation of Procedure 8, and substituting endo-3-[3-(N,N-Diethyl -carbamimidoyl)-phenoxazin-10-yl]-8-aza-bicyclo[3.2.1]-octane-8-carboxylic acid tert-butyl ester, 4b for endo-3-[3-(1H-tetrazol-5-yl)-phenoxazin-10-yl]-8-aza-bicyclo[3.2.1]-octane-8-carboxylic acid tert-butyl ester, 4b, the title compound endo-10-(8-aza-bicyclo[3.2.1]oct-3-yl)-N,N-diethyl-10H-phenoxazine-3-carboxamidine, 2c was obtained as a TFA salt. MS m/z (MH⁺) 390.9.

Endo-N,N-Diethyl-10-(8-pyridin-2-ylmethyl-8-aza-bicyclo[3.2.1]oct-3-yl)-10H-phenoxazine-3-carboxamidine, 3c Using an adaptation of Procedure 8, and substituting endo-10-(8-aza-bicyclo[3.2.1]oct-3-yl)-N,N-diethyl-10H-phenoxazine-3-carboxamidine, 2c for endo-10-(8-aza-bicyclo [3.2.1]oct-3-yl)-3-(1H-tetrazol-5-yl)-10H-phenoxazine, 5b, the title compound endo-N,N-diethyl-10-(8-pyridin-2-ylmethyl-8-aza-bicyclo[3.2.1]oct-3-yl)-10H-phenoxazine-3-carboxamidine, 3c was obtained as a TFA salt. MS m/z (MH⁺) 482.0.

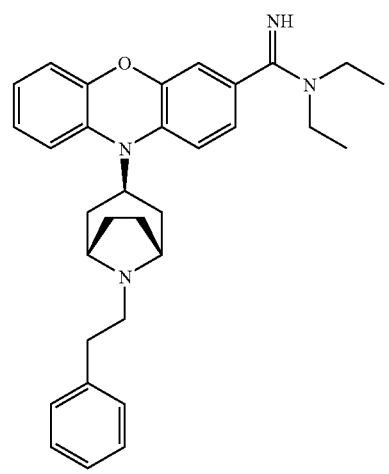

4c

Endo-N,N-Diethyl-10-(8-phenethyl-8-aza-bicyclo[3.2.1]oct-3-yl)-10H-phenoxazine-3-carboxamidine, 4c Using an adaptation of Procedure 9, substituting endo-N,N-diethyl-10-(8-pyridin-2-ylmethyl-8-aza-bicyclo[3.2.1]oct-3-yl)-10H-phenoxazine-3-carboxamidine, 3c for endo-10-(8-aza-bicyclo[3.2.1]oct-3-yl)-3-(1H-tetrazol-5-yl)-10H-phenoxazine, 5b and phenyl acetaldehyde for 2-pyridyl carboxaldehyde, the title compound endo-N,N-diethyl-10-(8-phenethyl-8-aza-bicyclo[3.2.1]oct-3-yl)-10H-phenoxazine-3-carboxamidine, 4c was obtained as a TFA salt. MS m/z (MH$^+$) 495.0.

Example D

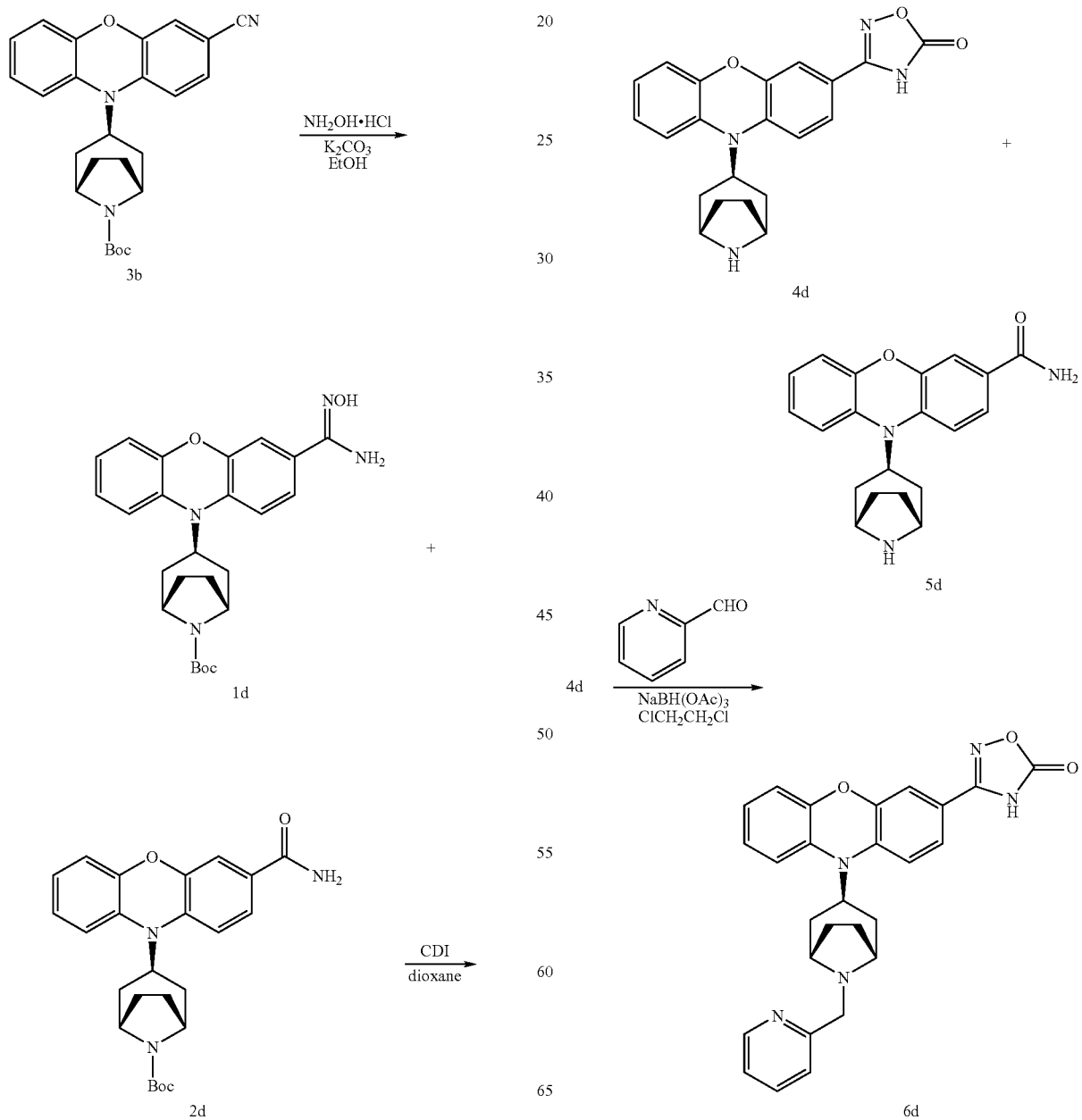

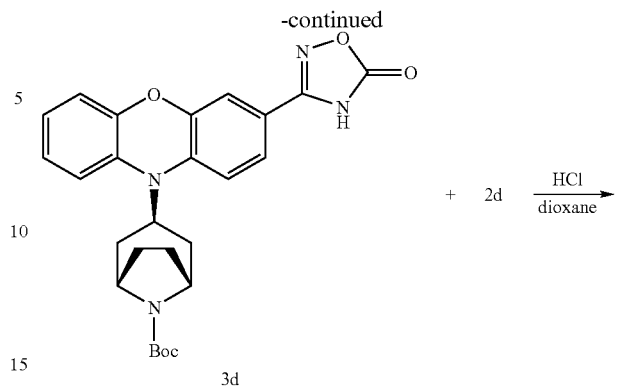

Procedure 11

Endo-3-[3-(N-Hydroxycarbamimidoyl)-phenoxazin-10-yl]-8-aza-bicyclo[3.2.1]octane-8-carboxylic acid tert-butyl ester, 1d and endo-3-(3-Carbamoyl-phenoxazin-10-yl)-8-aza-bicyclo[3.2.1]octane-8-carboxylic acid tert-butyl ester, 2d To a solution of endo-3-(3-cyano-phenoxazin-10-yl)-8-aza-bicyclo[3.2.1]octane-8-carboxylic acid tert-butyl ester, 3b (1 g; 2.40 mmol) in ethanol (20 mL) were added ammonium hydroxide hydrochloride (0.5 g; 7.19 mmol) and potassium carbonate (0.66 g; 4.78 mmol), and the mixture was heated to reflux for 16 h. The mixture was allowed to cool to rt, water (20 mL) was added, and the mixture was extracted with ethyl acetate (2×20 mL). The combined organic layers were dried over MgSO$_4$, filtered, and evaporated, yielding a ~2:1 mixture of title compounds endo-3-[3-(N-hydroxycarbamimidoyl)-phenoxazin-10-yl]-8-aza-bicyclo[3.2.1]octane-8-carboxylic acid tert-butyl ester, 1d and endo-3-(3-carbamoyl-phenoxazin-10-yl)-8-aza-bicyclo[3.2.1]octane-8-carboxylic acid tert-butyl ester, 2d. The crude mixture was used as such in the next reaction. 1d: MS m/z (MH$^+$) 451.2., 2d: MS m/z (MH$^+$) 458.3.

Procedure 12

Endo-3-[3-(5-Oxo-4,5-dihydro-[1,2,4]oxadiazol-3-yl)-phenoxazin-10-yl]-8-aza-bicyclo[3.2.1]octane-8-carboxylic acid tert-butyl ester, 3d To a solution of the 2:1 mixture of endo-3-[3-(N-hydroxycarbamimidoyl)-phenoxazin-10-yl]-8-aza-bicyclo[3.2.1]octane-8-carboxylic acid tert-butyl ester, 1d and endo-3-(3-carbamoyl-phenoxazin-10-yl)-8-aza-bicyclo[3.2.1]octane-8-carboxylic acid tert-butyl ester, 2d (2.33 mmol) in dioxane (20 mL) was added 1,1'-carbonyldiimidazole (0.57 g; 3.52 mmol), and the mixture was stirred at 110° C. for 4 h. The mixture was allowed to cool to rt, and the solution containing a crude mixture of endo-3-[3-(5-oxo-4,5-dihydro-[1,2,4]oxadiazol-3-yl)-phenoxazin-10-yl]-8-aza-bicyclo[3.2.1]-octane-8-carboxylic acid tert-butyl ester, 3d (MS m/z (MH$^+$) 477.1) and endo-3-(3-carbamoyl-phenoxazin-10-yl)-8-aza-bicyclo[3.2.1]octane-8-carboxylic acid tert-butyl ester, 2d was used as such in the next reaction.

Endo-3-[10-(8-Aza-bicyclo[3.2.1]oct-3-yl)-10H-phenoxazin-3-yl]-4H-[1,2,4]oxadiazol-5-one, 4d and endo-10-(8-Aza-bicyclo[3.2.1]oct-3-yl)-10H-phenoxazine-3-carboxylic acid amide, 5d Using an adaptation of Procedure 8, and substituting a mixture of endo-3-[3-(5-oxo-4,5-dihydro-[1,2,4]oxadiazol-3-yl)-phenoxazin-10-yl]-8-aza-bicyclo[3.2.1]-octane-8-carboxylic acid tert-butyl ester, 3d and endo-3-(3-carbamoyl-phenoxazin-10-yl)-8-aza-bicyclo[3.2.1]octane-8-carboxylic acid tert-butyl ester, 2d for endo-3-[3-(1H-tetrazol-5-yl)-phenoxazin-10-yl]-8-aza-bicyclo[3.2.1]-octane-8-carboxylic acid tert-butyl ester, 4b, the title compounds endo-3-[10-(8-aza-bicyclo[3.2.1]oct-3-yl)-10H-phenoxazin-3-yl]-4H-[1,2,4]oxadiazol-5-one, 4d and endo-10-(8-aza-bicyclo[3.2.1]oct-3-yl)-10H-phenoxazine-3-carboxylic acid amide, 5d were obtained as TFA salts. 4d: MS m/z (MH$^+$) 377.0; 5d: MS m/z (MH$^+$) 335.9.

Endo-3-[10-(8-Pyridin-2-ylmethyl-8-aza-bicyclo [3.2.1]oct-3-yl)-10H-phenoxazin-3-yl]-4H-[1,2,4] oxadiazol-5-one, 6d Using an adaptation of Procedure 9, and substituting endo-3-[10-(8-aza-bicyclo[3.2.1]oct-3-yl)-10H-phenoxazin-3-yl]-4H-[1,2,4]oxadiazol-5-one, 4d for endo-10-(8-aza-bicyclo[3.2.1]oct-3-yl)-3-(1H-tetrazol-5-yl)-10H-phenoxazine, 5b, the title compound endo-3-[10-(8-pyridin-2-ylmethyl-8-aza-bicyclo[3.2.1]oct-3-yl)-10H-phenoxazin-3-yl]-4H-[1,2,4]oxadiazol-5-one, 6d was obtained as a TFA salt. MS m/z (MH$^+$) 467.9.

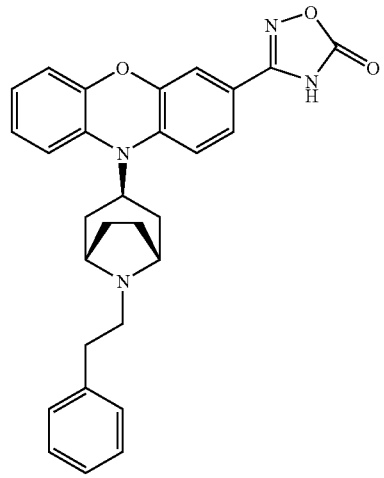

7d

Endo-3-[10-(8-Phenethyl-8-aza-bicyclo[3.2.1]oct-3-yl)-10H-phenoxazin-3-yl]-4H-[1,2,4]oxadiazol-5-one, 7d Using an adaptation of Procedure 9, and substituting endo-3-[10-(8-aza-bicyclo[3.2.1]oct-3-yl)-10H-phenoxazin-3-yl]-4H-[1,2,4]oxadiazol-5-one, 4d for endo-10-(8-aza-bicyclo[3.2.1]oct-3-yl)-3-(1H-tetrazol-5-yl)-10H-phenoxazine, 5b, and phenyl acetaldehyde for 2-pyridyl carboxaldehyde, the title compound endo-3-[10-(8-phenethyl-8-aza-bicyclo [3.2.1]oct-3-yl)-10H-phenoxazin-3-yl]-4H-[1,2,4]oxadiazol-5-one, 7d was obtained as a TFA salt MS m/z (MH$^+$) 480.9.

Example E

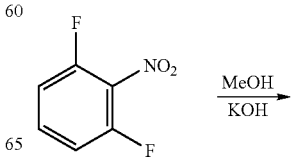

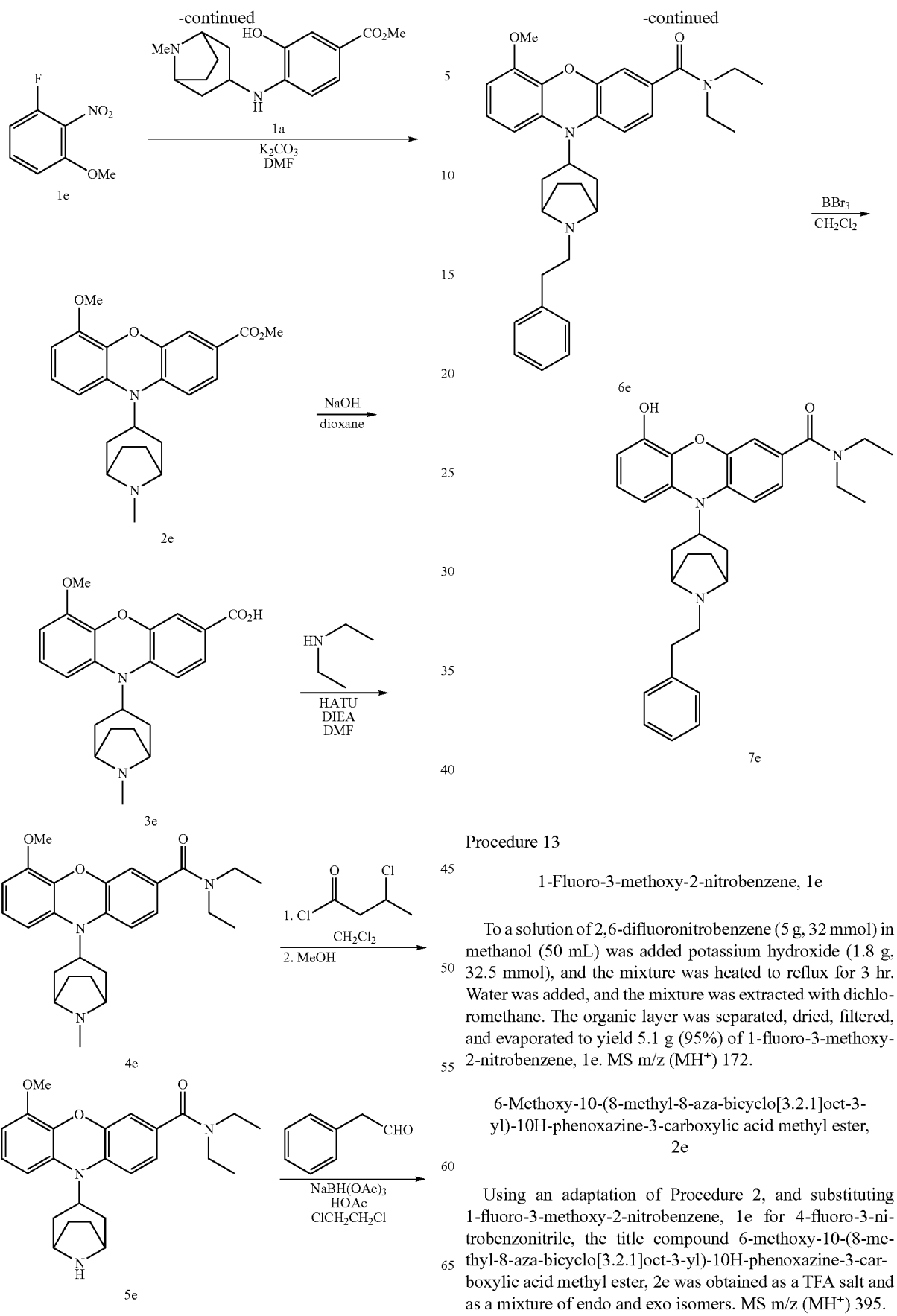

Procedure 13

1-Fluoro-3-methoxy-2-nitrobenzene, 1e

To a solution of 2,6-difluoronitrobenzene (5 g, 32 mmol) in methanol (50 mL) was added potassium hydroxide (1.8 g, 32.5 mmol), and the mixture was heated to reflux for 3 hr. Water was added, and the mixture was extracted with dichloromethane. The organic layer was separated, dried, filtered, and evaporated to yield 5.1 g (95%) of 1-fluoro-3-methoxy-2-nitrobenzene, 1e. MS m/z (MH$^+$) 172.

6-Methoxy-10-(8-methyl-8-aza-bicyclo[3.2.1]oct-3-yl)-10H-phenoxazine-3-carboxylic acid methyl ester, 2e Using an adaptation of Procedure 2, and substituting 1-fluoro-3-methoxy-2-nitrobenzene, 1e for 4-fluoro-3-nitrobenzonitrile, the title compound 6-methoxy-10-(8-methyl-8-aza-bicyclo[3.2.1]oct-3-yl)-10H-phenoxazine-3-carboxylic acid methyl ester, 2e was obtained as a TFA salt and as a mixture of endo and exo isomers. MS m/z (MH$^+$) 395.

Procedure 14

6-Methoxy-10-(8-methyl-8-aza-bicyclo[3.2.1]oct-3-yl)-10H-phenoxazine-3-carboxylic acid, 3e To a solution of the TFA salt of 6-methoxy-10-(8-methyl-8-aza-bicyclo[3.2.1]oct-3-yl)-10H-phenoxazine-3-carboxylic acid methyl ester, 2e (270 mg, 0.7 mmol) in dioxane (15 mL) was added sodium hydroxide (31 mg, 0.77 mmol) for 10-(8-methyl-8-aza-bicyclo[3.2.1]oct-3-yl)-10H-phenoxazine-3-carboxylic acid methyl ester, 2a, the title compound 6-methoxy-10-(8-methyl-8-aza-bicyclo[3.2.1]oct-3-yl)-10H-phenoxazine-3-carboxylic acid, 3e was obtained as a mixture of endo and exo isomers. MS m/z (MH$^+$) 381.

10-(8-Methyl-8-aza-bicyclo[3.2.1]oct-3-yl)-10H-phenoxazine-3-carboxylic acid diethylamide, 4e Using an adaptation of Procedure 4, and substituting 6-methoxy-10-(8-methyl-8-aza-bicyclo[3.2.1]oct-3-yl)-10H-phenoxazine-3-carboxylic acid, 3e for 10-(8-methyl-8-aza-bicyclo[3.2.1]oct-3-yl)-10H-phenoxazine-3-carboxylic acid, 3a, N,N-diisopropyl-N-ethylamine for triethylamine and HATU for HBTU, the title compound 10-(8-methyl-8-aza-bicyclo[3.2.1]oct-3-yl)-10H-phenoxazine-3-carboxylic acid diethylamide, 4e was obtained as a TFA salt and as a mixture of endo and exo isomers. MS m/z (MH$^+$) 436.

Procedure 15

10-(8-Aza-bicyclo[3.2.1]oct-3-yl)-6-methoxy-10H-phenoxazine-3-carboxylic acid diethylamide, 5e To a solution of the TFA salt of 10-(8-methyl-8-aza-bicyclo[3.2.1]oct-3-yl)-10H-phenoxazine-3-carboxylic acid diethylamide, 4e (110 mg, 0.25 mmol) in methylene chloride (10 mL) was added 1-chloroethyl chloroformate (0.58 mL, 0.75 mmol). The mixture was heated to reflux for 2 h. The mixture was evaporated, dissolved in methanol (5 mL), and heated for 2 h at reflux. Water was added, and the solution was extracted with methylene chloride. The organic phase was separated, evaporated, and purified via reverse phase HPLC to yield 69 mg (44.8%) of title compound 10-(8-aza-bicyclo[3.2.1]oct-3-yl)-6-methoxy-10H-phenoxazine-3-carboxylic acid diethylamide, 5e, as a TFA salt. MS m/z=422 (M+1).

6-Methoxy-10-(8-phenethyl-8-aza-bicyclo[3.2.1]oct-3-yl)-10H-phenoxazine-3-carboxylic acid diethylamide, 6e Using an adaptation of Procedure 9, and substituting 10-(8-aza-bicyclo[3.2.1]oct-3-yl)-6-methoxy-10H-phenoxazine-3-carboxylic acid diethylamide, 5e for endo-10-(8-aza-bicyclo[3.2.1]oct-3-yl)-3-(1H-tetrazol-5-yl)-10H-phenoxazine, 5b, and phenyl acetaldehyde for 2-pyridylcarboxaldehyde, the title compound 6-methoxy-10-(8-phenethyl-8-aza-bicyclo[3.2.1]oct-3-yl)-10H-phenoxazine-3-carboxylic acid diethylamide, 6e was obtained as a TFA salt and as a mixture of endo and exo isomers. MS m/z=526 (M+1).

Procedure 16

6-Hydroxy-10-(8-phenethyl-8-aza-bicyclo[3.2.1]oct-3-yl)-10H-phenoxazine-3-carboxylic acid diethylamide, 7e To a solution of the TFA salt of 6-methoxy-10-(8-phenethyl-8-aza-bicyclo[3.2.1]oct-3-yl)-10H-phenoxazine-3-carboxylic acid diethylamide, 6e (55 mg, 0.086 mmol) in 1,2-dichloromethane (5 mL) at 0° C. was added a 1M solution of BBr$_3$ (0.43 mL, 0.43 mmol). The mixture was allowed to stir for 2 h at rt. A saturated NaHCO$_3$ solution was added, and the organic phase was separated. The aqueous phase was extracted with methylene chloride, and the combined organic phases were dried, filtered, and evaporated. The residue was purified via reverse phase HPLC (eluent: CH$_3$CN in water containing 0.1% TFA) to yield 23 mg (42.8%) of title compound 6-hydroxy-10-(8-phenethyl-8-aza-bicyclo[3.2.1]oct-3-yl)-10H-phenoxazine-3-carboxylic acid diethylamide, 7e as a TFA salt and as a mixture of endo and exo isomers. MS m/z=512 (M+1).

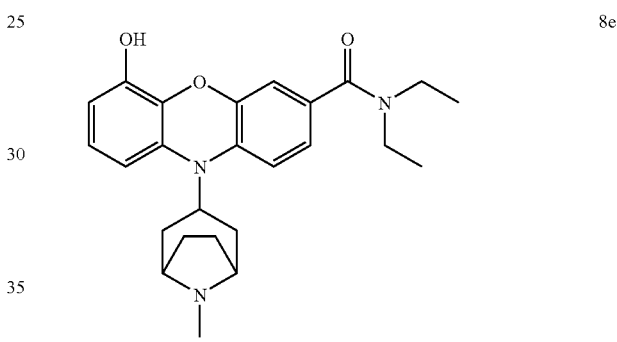

8e

6-Methoxy-10-(8-methyl-8-aza-bicyclo[3.2.1]oct-3-yl)-10H-phenoxazine-3-carboxylic acid diethylamide, 8e Using an adaptation of Procedure 16, and substituting the TFA salt of 10-(8-methyl-8-aza-bicyclo[3.2.1]oct-3-yl)-10H-phenoxazine-3-carboxylic acid diethylamide, 4e for TFA salt of 6-methoxy-10-(8-phenethyl-8-aza-bicyclo[3.2.1]oct-3-yl)-10H-phenoxazine-3-carboxylic acid diethylamide, 6e, the title compound 6-methoxy-10-(8-methyl-8-aza-bicyclo[3.2.1]oct-3-yl)-10H-phenoxazine-3-carboxylic acid diethylamide, 8e was obtained as a TFA salt and as a mixture of endo and exo isomers after reverse phase chromatography (eluent gradient: acetonitrile in water containing 0.1% TFA). MS m/z (MH$^+$) 422.

Example F

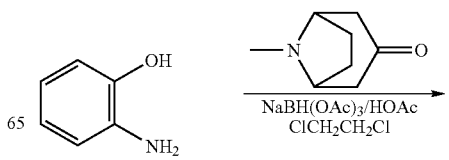

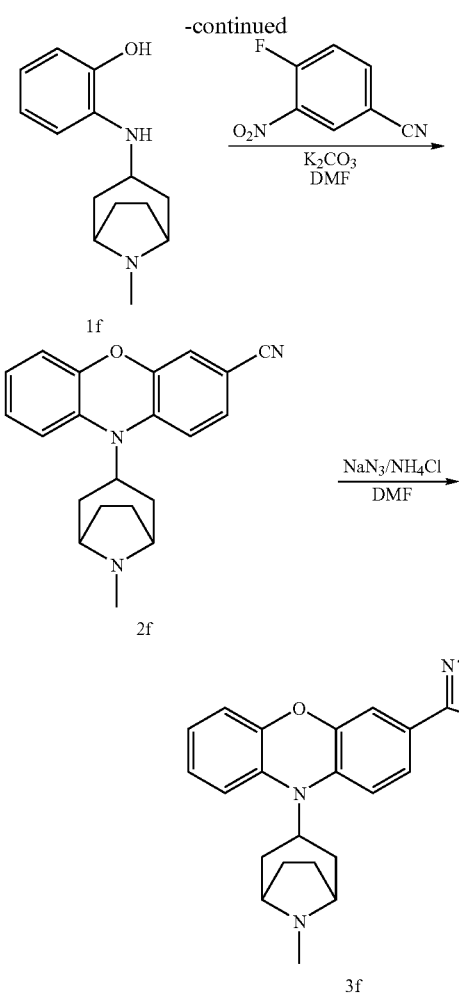

2-(8-Methyl-8-aza-bicyclo[3.2.1]oct-3-ylamino)-phenol, 1f

Using an adaptation of Procedure 5, and substituting 8-methyl-8-aza-bicyclo[3.2.1]-octan-3-one for 3-oxo-8-aza-bicyclo[3.2.1]octane-8-carboxylic acid tert-butyl ester, the title compound 2-(8-methyl-8-aza-bicyclo[3.2.1]oct-3-ylamino)-phenol, 1f was obtained as a TFA salt and as a mixture of endo and exo isomers after reverse phase chromatography (eluent gradient: acetonitrile in water containing 0.1% TFA). MS m/z (MH+) 232.9.

10-(8-Methyl-8-aza-bicyclo[3.2.1]oct-3-yl)-10H-phenoxazine-3-carbonitrile, 2f Using an adaptation of Procedure 6, and substituting the TFA salt of 2-(8-methyl-8-aza-bicyclo[3.2.1]oct-3-ylamino)-phenol, 1f for 3-(2-hydroxy-phenylamino)-8-aza-bicyclo[3.2.1]octane-8-carboxylic acid tert-butyl ester, 1b, the title compound 10-(8-methyl-8-aza-bicyclo[3.2.1]oct-3-yl)-10H-phenoxazine-3-carbonitrile, 2f was obtained as a mixture of endo and exo isomers. MS m/z (MH+) 332.0.

10-(8-Methyl-8-aza-bicyclo[3.2.1]oct-3-yl)-3-(1H-tetrazol-5-yl)-10H-phenoxazine, 3f Using an adaptation of Procedure 7, and substituting 10-(8-methyl-8-aza-bicyclo[3.2.1]oct-3-yl)-10H-phenoxazine-3-carbonitrile, 2f for 3-(3-cyano-phenoxazin-10-yl)-8-aza-bicyclo[3.2.1]octane-8-carboxylic acid tert-butyl ester, 2b, the title compound 10-(8-methyl-8-aza-bicyclo[3.2.1]oct-3-yl)-3-(1H-tetrazol-5-yl)-10H-phenoxazine, 3f was obtained as a TFA salt and as a mixture of endo and exo isomers after reverse phase chromatography (eluent gradient: acetonitrile in water containing 0.1% TFA). MS m/z (MH+) 375.1.

Example G

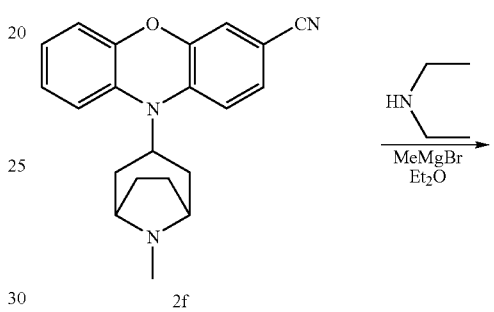

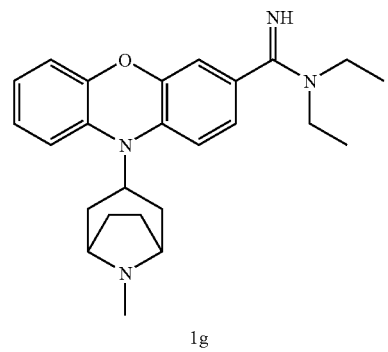

N,N-Diethyl-10-(8-methyl-8-aza-bicyclo[3.2.1]oct-3-yl)-10H-phenoxazine-3-carboxamidine, 1g Using an adaptation of Procedure 10, and substituting 10-(8-methyl-8-aza-bicyclo[3.2.1]oct-3-yl)-10H-phenoxazine-3-carbonitrile, 2f for endo-3-(3-cyano-phenoxazin-10-yl)-8-aza-bicyclo[3.2.1]octane-8-carboxylic acid tert-butyl ester, 3b, the title compound N,N-diethyl-10-(8-methyl-8-aza-bicyclo[3.2.1]oct-3-yl)-10H-phenoxazine-3-carboxamidine, 1g was obtained as a TFA salt and as a mixture of endo and exo isomers after reverse phase chromatography (eluent gradient: acetonitrile in water containing 0.1% TFA). MS m/z (MH+) 405.3.

Example H

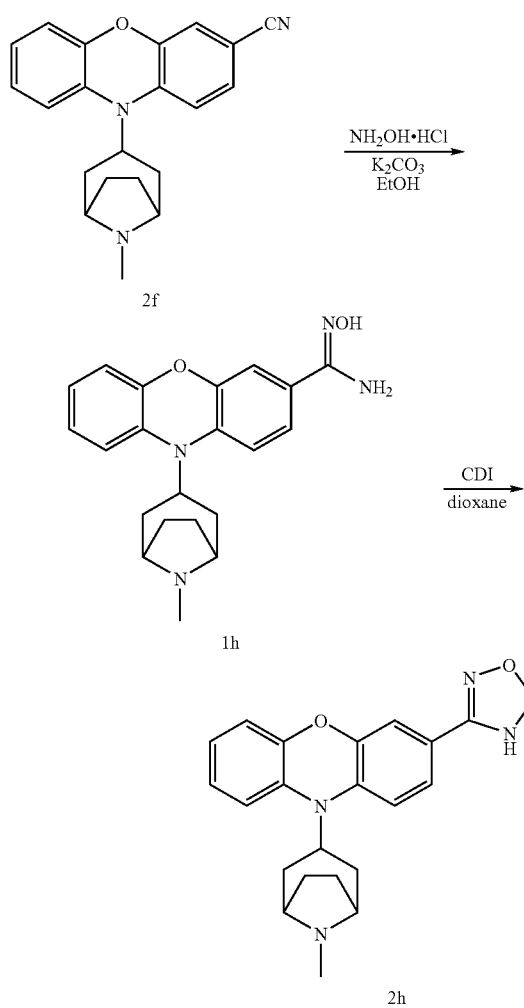

N-Hydroxy-10-(8-methyl-8-aza-bicyclo[3.2.1]oct-3-yl)-10H-phenoxazine-3-carboxamidine, 1h Using an adaptation of Procedure 11, and substituting 10-(8-methyl-8-aza-bicyclo[3.2.1]oct-3-yl)-10H-phenoxazine-3-carbonitrile, 2f for endo-3-(3-cyano-phenoxazin-10-yl)-8-aza-bicyclo[3.2.1]octane-8-carboxylic acid tert-butyl ester, 3b, the title compound N-Hydroxy-10-(8-methyl-8-aza-bicyclo[3.2.1]oct-3-yl)-10H-phenoxazine-3-carboxamidine, 1 h was obtained. MS m/z (MH+) 365.0.

Procedure 17

3-[10-(8-Methyl-8-aza-bicyclo[3.2.1]oct-3-yl)-10H-phenoxazin-3-yl]-4H-[1,2,4]oxadiazol-5-one, 2h To a solution of N-Hydroxy-10-(8-methyl-8-aza-bicyclo[3.2.1]oct-3-yl)-10H-phenoxazine-3-carboxamidine, 1 h (0.66 g; 1.81 mmol) in dioxane (20 mL) was added 1,1'-carbonyldiimidazole (0.44 g; 2.71 mmol), and the mixture was stirred at 110° C. for 4 h. The mixture was allowed to cool to rt, and the solvent was evaporated. The residue was purified via reverse phase HPLC (eluent gradient: 20 to 45% CH3CN in H2O containing 0.1% TFA) to yield 161 mg (17.6%) of title compound 3-[10-(8-methyl-8-aza-bicyclo[3.2.1]oct-3-yl)-10H-phenoxazin-3-yl]-4H-[1,2,4]oxadiazol-5-one, 2h as a TFA salt. MS m/z (MH+) 390.9.

Example I

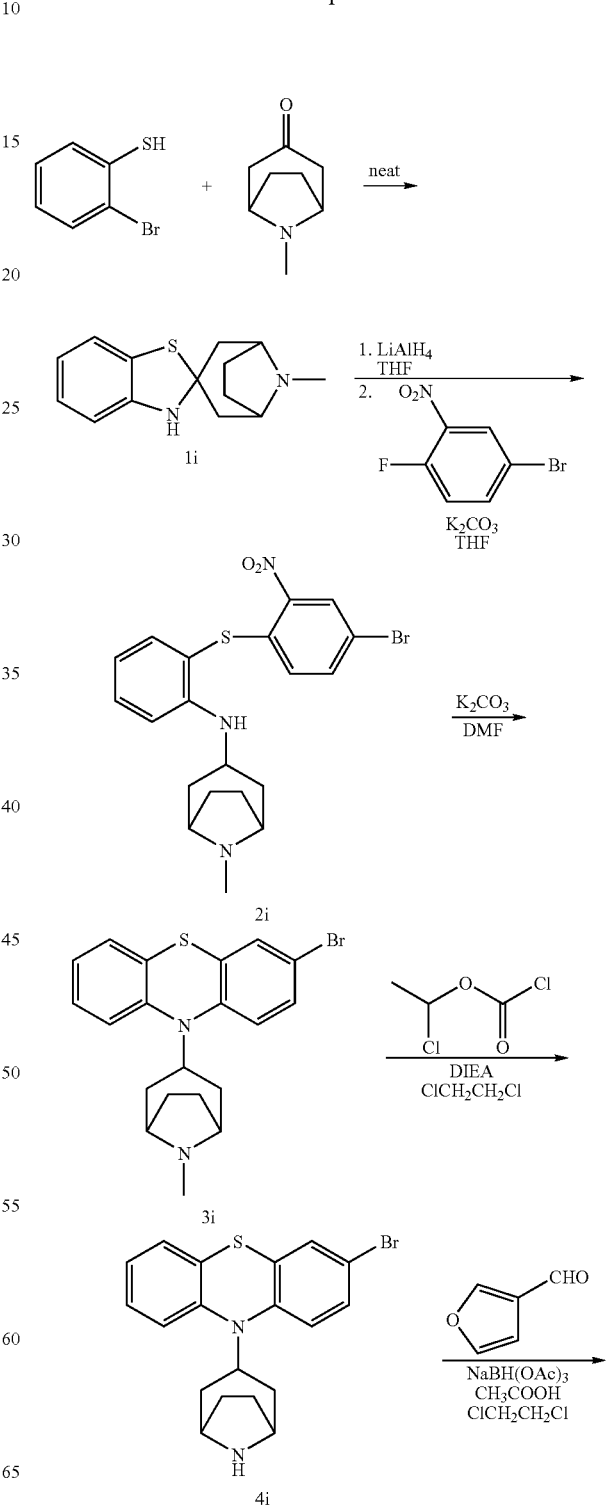

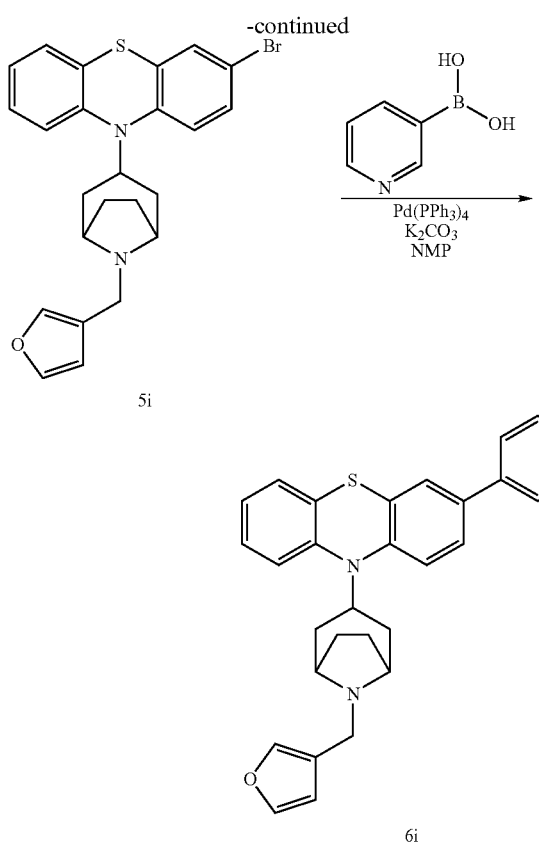

Procedure 18

Spiro Compound, 1i

A mixture of 2-aminothiophenol (4.3 mL, 39.9 mmol) and tropinone (5.6 g, 39.9 mmol) was allowed to stir and sit for 16 h at rt. The mixture was placed under vacuum (<0.3 mm Hg) for 6 h. HPLC-MS analysis revealed ~60% conversion to desired compound, 1i. The material was used as such for the next reaction.

Procedure 19

[2-(4-Bromo-2-nitrophenylsulfanyl)-phenyl]-(8-methyl-8-aza-bicyclo[3.2.1]oct-3-yl)-amine, 2i To the mixture obtained from the previous reaction (Procedure 18) was added THF (20 mL), and the mixture was cooled to −78° C. A 1M solution of lithium aluminum hydride in diethyl ether (60 mL, 60 mmol) was added in portions. The cooling bath was removed. More THF (60 mL) and 10 mL of the 1M solution of lithium aluminum hydride were added. The mixture was stirred at rt for 90 min, cooled to −78° C., and treated with water (2.6 mL). The cooling bath was removed, and the mixture was allowed to warm to rt. A 1N NaOH solution (10.6 mL) was added, and the mixture was allowed to stir for 15 min. MgSO$_4$ (1 g) and THF (40 mL) were added, and the mixture was filtered. To the filtrate was added 2-fluoro-5-bromo-nitrobenzene (5.4 mL, 43.8 mmol), and the mixture was stirred for 15 min. The reaction mixture was filtered, and the solid was washed with THF (3×20 mL) and ethyl acetate (4×20 mL). The combined filtrates were evaporated, and the residue was purified via flash column chromatography (eluent gradient: 20% EtOAc containing 1% Et$_3$N in heptane to 20% MeOH containing 1% Et$_3$N in EtOAc), yielding 10 g (55.9%) of title compound [2-(4-bromo-2-nitrophenylsulfanyl)-phenyl]-(8-methyl-8-aza-bicyclo[3.2.1]oct-3-yl)-amine, 2i as a mixture of endo and exo isomers.

Procedure 20

3-Bromo-10-(8-methyl-8-aza-bicyclo[3.2.1]oct-3-yl)-10H-phenothiazine, 3i

To a solution of [2-(4-bromo-2-nitrophenylsulfanyl)-phenyl]-(8-methyl-8-aza-bicyclo[3.2.1]oct-3-yl)-amine, 2i (9.7 g, 21.6 mmol) in DMSO (220 mL) was added potassium carbonate (3.3 g, 23.8 mmol). The mixture was heated under a N$_2$ atmosphere to 170° C. for 45 min. The mixture was allowed to cool to rt, diluted with H$_2$O (250 mL), and extracted with EtOAc (4×100 mL). The organic phase was dried over Na$_2$SO$_4$, filtered, and evaporated. The residue was purified via flash column chromatography (eluent gradient: 1% Et$_3$N in EtOAc to 30% MeOH in EtOAc containing 1% Et$_3$N), yielding 1.9 g (21.9%) of title compound 3-bromo-10-(8-methyl-8-aza-bicyclo[3.2.1]oct-3-yl)-10H-phenothiazine, 3i as a mixture of endo and exo isomers. MS m/z (MH$^+$) 401.1/403.1.

Procedure 21

10-(8-Aza-bicyclo[3.2.1]oct-3-yl)-3-bromo-10H-phenothiazine, 4i

To a solution of 3-bromo-10-(8-methyl-8-aza-bicyclo[3.2.1]oct-3-yl)-10H-phenothiazine, 3i (1.0 g, 2.49 mmol) in 1,2-dichloroethane (15 mL) were added 1-chloroethyl chloroformate (807 μL, 7.5 mmol) and N,N-diisopropyl-N-ethylamine (1.4 mL, 7.97 mmol). The mixture was heated to reflux for 2.5 h, allowed to cool to rt, and evaporated. The mixture was evaporated and the residue was dissolved in methanol (15 mL) and heated to reflux for 1 h. After work-up, the residue was purified via flash column chromatography (eluent gradient: 0 to 30% MeOH in EtOAc containing 1% triethylamine) to yield 150 mg of recovered starting material 3i and 382 mg (66%) of title compound 3-bromo-10-piperidin-4-yl-10H-phenothiazine, 4i as a mixture of endo and exo isomers. MS m/z (MH$^+$) 387.1/389.1.

Procedure 22

3-Bromo-10-(8-furan-3-ylmethyl-8-aza-bicyclo [3.2.1]oct-3-yl)-10H-phenothiazine, 5i To a solution of 3-bromo-10-piperidin-4-yl-10H-phenothiazine, 4i (11.2 mg; 0.029 mmol) and 3-furyl carboxaldehyde (8.4 mg; 0.087 mmol) in dichloroethane (120 μL) was added acetic acid (5 μL) and a solution of sodium triacetoxyborohydride (12 mg, 0.057 mmol) in DMF (100μ). The mixture was stirred at rt for 18 h, quenched with water (50 μL), and lyophilized. The thus obtained crude 3-bromo-10-(8-furan-3-ylmethyl-8-aza-bicyclo[3.2.1]oct-3-yl)-10H-phenothiazine, 5i as a mixture of endo and exo isomers was used as such for the next reaction.

Procedure 23

10-(8-Furan-3-ylmethyl-8-aza-bicyclo[3.2.1]oct-3-yl)-3-pyridin-3-yl-10H-phenothiazine, 6i A mixture of 3-bromo-10-(8-furan-3-ylmethyl-8-aza-bicyclo[3.2.1]oct-3-yl)-10H-phenothiazine, 5i (13.5 mg, 0.029 mmol), 3-pyridyl boronic acid (10.7 mg, 0.087 mmol), potassium carbonate (12 mg, 0.087 mmol) and Pd(PPh$_3$)$_4$ (3 mg, 2.5 μmol) in NMP (300 μL) and H$_2$O (100 μL) was heated to 160° C. for 10 min in a microwave. The mixture was absorbed onto a 1 g SPE cartridge and eluted (eluent: 10% methanol in ethyl acetate containing 1% triethylamine). The eluent (~15 mL) was collected and evaporated. The residue was purified via reverse phase HPLC (eluent: acetonitrile in water containing 0.1% TFA) to yield title compound 10-(8-furan-3-ylmethyl-8-aza-bicyclo[3.2.1]oct-3-yl)-3-pyridin-3-yl-10H-phenothiazine, 6i as a TFA salt and as a mixture of endo and exo isomers. MS m/z (MH$^+$) 466.2.

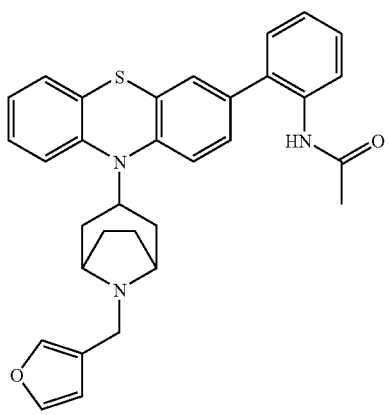

7i

N-{2-[10-(8-Furan-3-ylmethyl-8-aza-bicyclo[3.2.1]oct-3-yl)-10H-phenothiazin-3-yl]-phenyl}-acetamide, 7i Using an adaptation of the method described in Procedure 23, substituting 2-acetylaminophenyl boronic acid for 3-pyridyl boronic acid, the title compound N-{2-[10-(8-furan-3-ylmethyl-8-aza-bicyclo[3.2.1]oct-3-yl)-10H-phenothiazin-3-yl]-phenyl}-acetamide, 7i was obtained as a TFA salt and as a mixture of endo and exo isomers. MS m/z (MH$^+$) 522.2.

10-[8-(3-Methyl-but-2-enyl)-8-aza-bicyclo[3.2.1]oct-3-yl]-3-pyridin-3-yl-10H-phenothiazine, 8i Using an adaptation of the methods described in Procedures 22 and 23, substituting 3-methyl-but-2-enal for 3-furyl carboxaldehyde in Procedure 22, the title compound 10-[8-(3-methyl-but-2-enyl)-8-aza-bicyclo[3.2.1]oct-3-yl]-3-pyridin-3-yl-10H-phenothiazine, 8i was obtained as a TFA salt and as a mixture of endo and exo isomers. MS m/z (MH$^+$) 454.3.

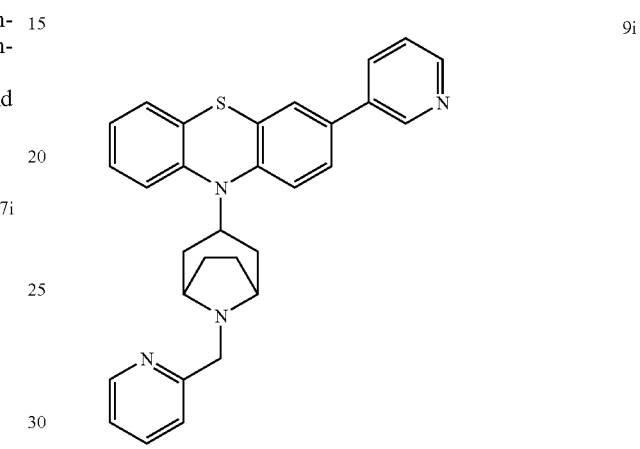

3-Pyridin-3-yl-10-(8-pyridin-2-ylmethyl-8-aza-bicyclo[3.2.1]oct-3-yl)-10H-phenothiazine, 9i Using an adaptation of the methods described in Procedures 22 and 23, substituting 2-pyridyl carboxaldehyde for 3-furyl carboxaldehyde in Procedure 22, the title compound 3-pyridin-3-yl-10-(8-pyridin-2-ylmethyl-8-aza-bicyclo[3.2.1]oct-3-yl)-10H-phenothiazine, 9i was obtained as a TFA salt and as a mixture of endo and exo isomers. MS m/z (MH$^+$) 477.2.

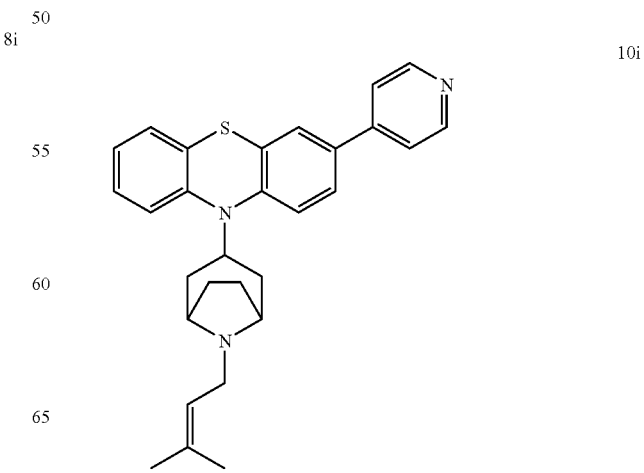

10-[8-(3-Methyl-but-2-enyl)-8-aza-bicyclo[3.2.1]oct-3-yl]-3-pyridin-4-yl-10H-phenothiazine, 10i Using an adaptation of the methods described in Procedures 22 and 23, substituting 3-methyl-but-2-enal for 3-furyl carboxaldehyde in Procedure 22, and 4-pyridyl boronic acid for 3-pyridyl boronic acid in Procedure 23, the title compound 10-[8-(3-methyl-but-2-enyl)-8-aza-bicyclo[3.2.1]oct-3-yl]-3-pyridin-4-yl-10H-phenothiazine, 10i was obtained as a TFA salt and as a mixture of endo and exo isomers. MS m/z (MH$^+$) 454.3.

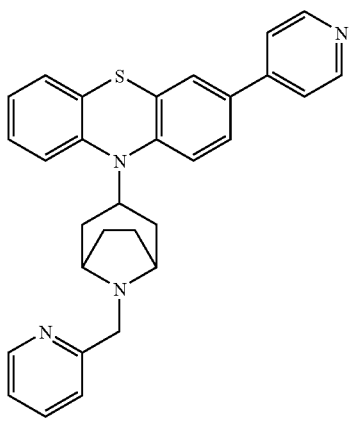

3-Pyridin-4-yl-10-(8-pyridin-2-ylmethyl-8-aza-bicyclo[3.2.1]oct-3-yl)-10H-phenothiazine, 11i Using an adaptation of the methods described in Procedures 22 and 23, substituting 2-pyridyl carboxaldehyde for 3-furyl carboxaldehyde in Procedure 22, and 4-pyridyl boronic acid for 3-pyridyl boronic acid in Procedure 23, the title compound 3-pyridin-4-yl-10-(8-pyridin-2-ylmethyl-8-aza-bicyclo[3.2.1]oct-3-yl)-10H-phenothiazine, 11i was obtained as a TFA salt and as a mixture of endo and exo isomers. MS m/z (MH$^+$) 477.3.

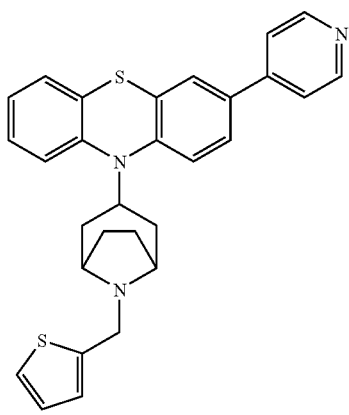

3-Pyridin-4-yl-10-(8-thiophen-2-ylmethyl-8-aza-bicyclo[3.2.1]oct-3-yl)-10H-phenothiazine, 12i Using an adaptation of the methods described in Procedures 22 and 23, substituting 2-thiophene carboxaldehyde for 3-furyl carboxaldehyde in Procedure 22, and 4-pyridyl boronic acid for 3-pyridyl boronic acid in Procedure 23, the title compound 3-pyridin-4-yl-10-(8-thiophen-2-ylmethyl-8-aza-bicyclo[3.2.1]oct-3-yl)-10H-phenothiazine, 12i was obtained as a TFA salt and as a mixture of endo and exo isomers. MS m/z (MH$^+$) 482.2.

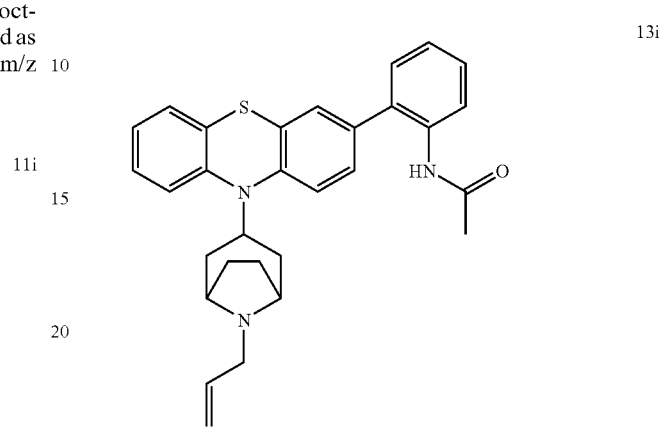

N-{2-[10-(8-Allyl-8-aza-bicyclo[3.2.1]oct-3-yl)-10H-phenothiazin-3-yl]-phenyl}-acetamide, 13i Using an adaptation of the methods described in Procedures 22 and 23, substituting propenal for 3-furyl carboxaldehyde in Procedure 22, and 2-acetylaminophenyl boronic acid for 3-pyridyl boronic acid in Procedure 23, the title compound N-{2-[10-(8-allyl-8-aza-bicyclo[3.2.1]oct-3-yl)-10H-phenothiazin-3-yl]-phenyl}-acetamide, 13i was obtained as a TFA salt and as a mixture of endo and exo isomers.

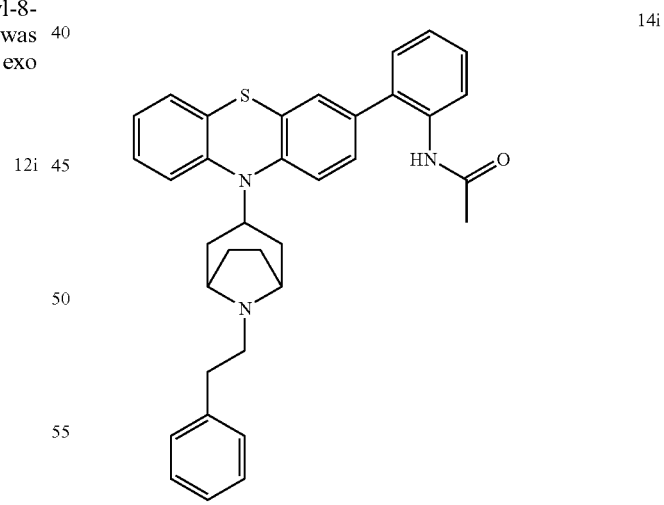

N-{2-[10-(8-Phenethyl-8-aza-bicyclo[3.2.1]oct-3-yl)-10H-phenothiazin-3-yl]-phenyl}-acetamide, 14i Using an adaptation of the methods described in Procedures 22 and 23, substituting phenyl acetaldehyde for 3-furyl carboxaldehyde in Procedure 22, and 2-acetylaminophenyl boronic acid for 3-pyridyl boronic acid in Procedure 23, the title compound N-{2-[10-(8-phenethyl-8-aza-bicyclo[3.2.1]oct-3-yl)-10H-phenothiazin-3-yl]-phenyl}-acetamide, 14i was obtained as a TFA salt and as a mixture of endo and exo isomers. MS m/z (MH⁺) 546.3.

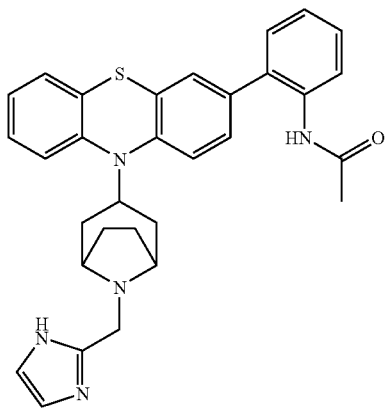

N-(2-{10-[8-(1H-Imidazol-2-ylmethyl)-8-aza-bicyclo[3.2.1]oct-3-yl]-10H-phenothiazin-3-yl}-phenyl)-acetamide, 15i Using an adaptation of the methods described in Procedures 22 and 23, substituting 1H-imidazole-2-carboxaldehyde for 3-furyl carboxaldehyde in Procedure 22, and 2-acetylaminophenyl boronic acid for 3-pyridyl boronic acid in Procedure 23, the title compound N-(2-{10-[8-(1H-Imidazol-2-ylmethyl)-8-aza-bicyclo[3.2.1]oct-3-yl]-10H-phenothiazin-3-yl}-phenyl)-acetamide, 15i was obtained as a TFA salt and as a mixture of endo and exo isomers. MS m/z (MH⁺) 522.3.

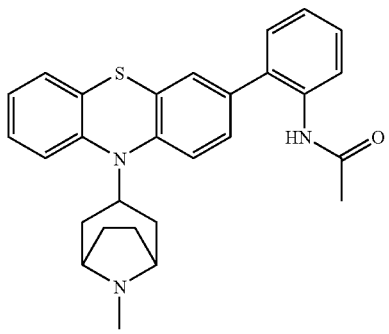

N-{2-[10-(8-Methyl-8-aza-bicyclo[3.2.1]oct-3-yl)-10H-phenothiazin-3-yl]-phenyl}-acetamide, 16i Using an adaptation of the method described in Procedure 23, substituting 3-bromo-10-(8-methyl-8-aza-bicyclo[3.2.1]oct-3-yl)-10H-phenothiazine, 3i for 3-bromo-10-(8-furan-3-ylmethyl-8-aza-bicyclo[3.2.1]oct-3-yl)-10H-phenothiazine, 5i and 2-acetylaminophenyl boronic acid for 3-pyridyl boronic acid, the title compound N-{2-[10-(8-methyl-8-aza-bicyclo[3.2.1]oct-3-yl)-10H-phenothiazin-3-yl]-phenyl}-acetamide, 16i was obtained as a TFA salt and as a mixture of endo and exo isomers. MS m/z (MH⁺) 456.2.

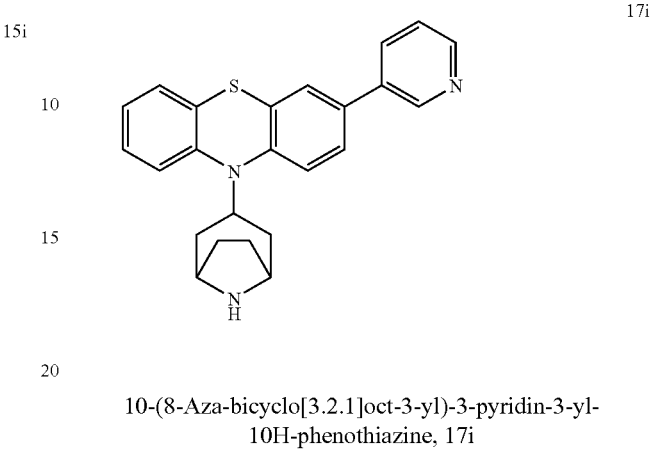

10-(8-Aza-bicyclo[3.2.1]oct-3-yl)-3-pyridin-3-yl-10H-phenothiazine, 17i

Using an adaptation of the method described in Procedure 23, substituting 3-bromo-10-piperidin-4-yl-10H-phenothiazine, 4i for 3-bromo-10-(8-furan-3-ylmethyl-8-aza-bicyclo[3.2.1]oct-3-yl)-10H-phenothiazine, 5l, the title compound 10-(8-aza-bicyclo[3.2.1]oct-3-yl)-3-pyridin-3-yl-10H-phenothiazine, 17i was obtained as a TFA salt and as a mixture of endo and exo isomers. MS m/z (MH⁺) 386.2.

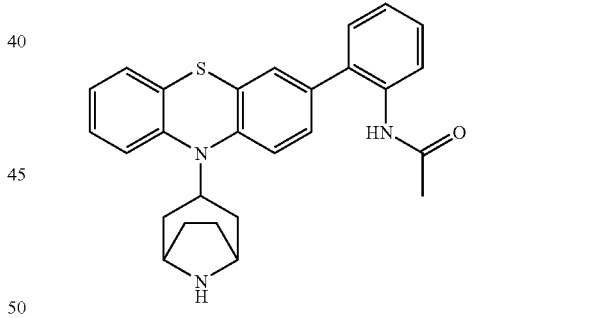

N-{2-[10-(8-Aza-bicyclo[3.2.1]oct-3-yl)-10H-phenothiazin-3-yl]-phenyl}-acetamide, 18i Using an adaptation of the method described in Procedure 23, substituting 10-(8-aza-bicyclo[3.2.1]oct-3-yl)-3-bromo-10H-phenothiazine, 4i for 3-bromo-10-(8-furan-3-ylmethyl-8-aza-bicyclo[3.2.1]oct-3-yl)-10H-phenothiazine, 5i and 2-acetylaminophenyl boronic acid for 3-pyridyl boronic acid, the title compound N-{2-[10-(8-aza-bicyclo[3.2.1]oct-3-yl)-10H-phenothiazin-3-yl]-phenyl}-acetamide, 18i was obtained as a TFA salt and as a mixture of endo and exo isomers. MS m/z (MH⁺) 442.2.

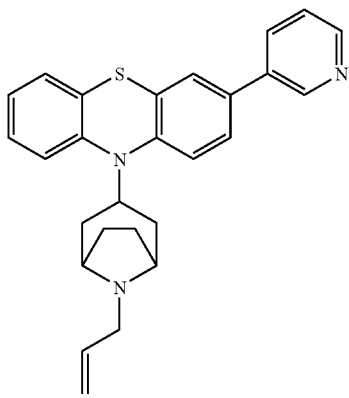

10-(8-Allyl-8-aza-bicyclo[3.2.1]oct-3-yl)-3-pyridin-3-yl-10H-phenothiazine, 19i

Using an adaptation of the methods described in Procedures 22 and 23, substituting 2-propenal for 3-furyl carboxaldehyde in Procedure 22, the title compound 10-(8-allyl-8-aza-bicyclo[3.2.1]oct-3-yl)-3-pyridin-3-yl-10H-phenothiazine, 19i was obtained as a TFA salt and as a mixture of endo and exo isomers. MS m/z (M+18+H) 444.2.

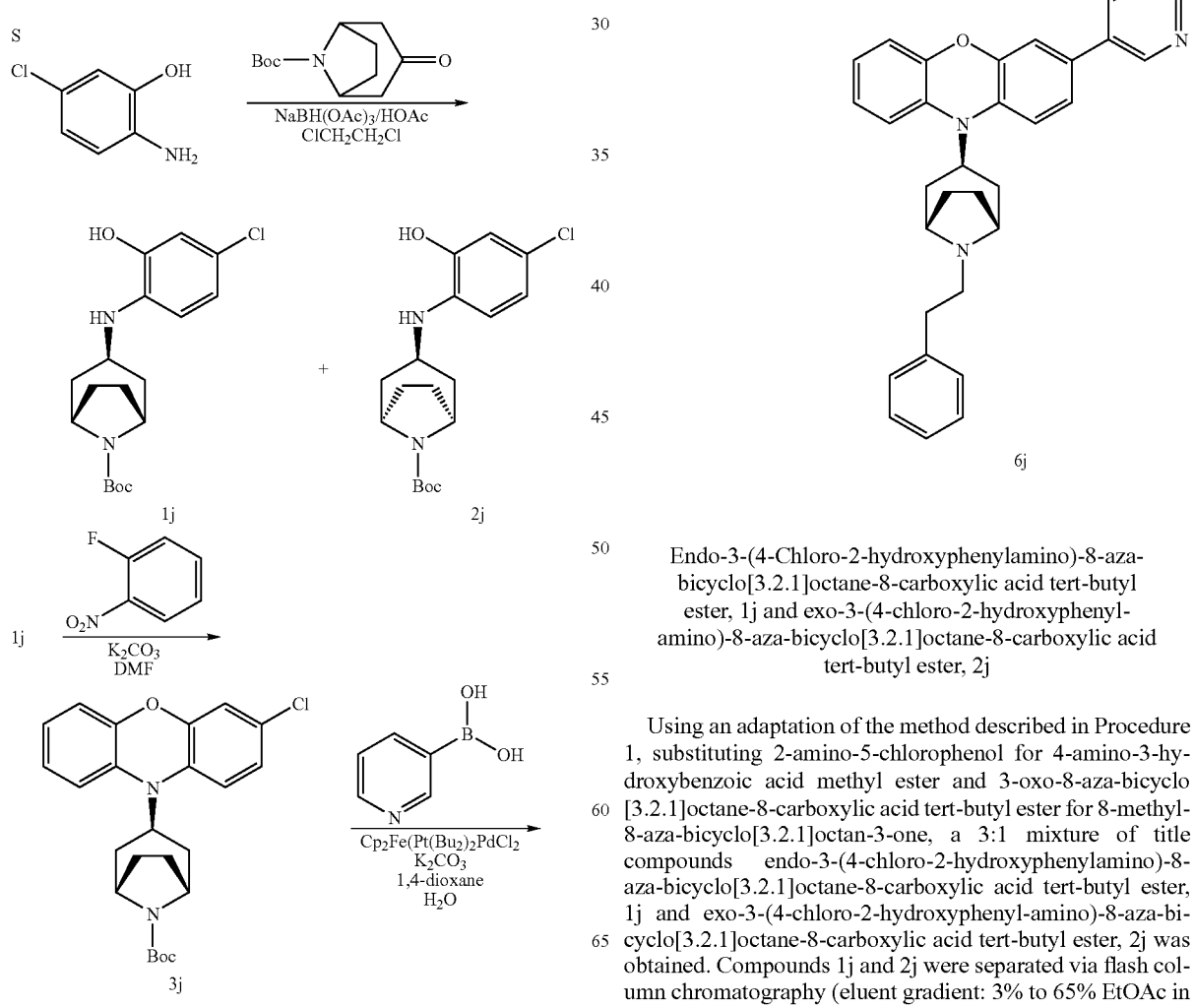

Endo-3-(4-Chloro-2-hydroxyphenylamino)-8-aza-bicyclo[3.2.1]octane-8-carboxylic acid tert-butyl ester, 1j and exo-3-(4-chloro-2-hydroxyphenylamino)-8-aza-bicyclo[3.2.1]octane-8-carboxylic acid tert-butyl ester, 2j Using an adaptation of the method described in Procedure 1, substituting 2-amino-5-chlorophenol for 4-amino-3-hydroxybenzoic acid methyl ester and 3-oxo-8-aza-bicyclo[3.2.1]octane-8-carboxylic acid tert-butyl ester for 8-methyl-8-aza-bicyclo[3.2.1]octan-3-one, a 3:1 mixture of title compounds endo-3-(4-chloro-2-hydroxyphenylamino)-8-aza-bicyclo[3.2.1]octane-8-carboxylic acid tert-butyl ester, 1j and exo-3-(4-chloro-2-hydroxyphenyl-amino)-8-aza-bicyclo[3.2.1]octane-8-carboxylic acid tert-butyl ester, 2j was obtained. Compounds 1j and 2j were separated via flash column chromatography (eluent gradient: 3% to 65% EtOAc in hexane), yielding 70% of endo isomer 1j (first eluting isomer; and 19% of exo isomer 2j (second eluting isomer)

Endo-3-(3-Chlorophenoxazin-10-yl)-8-aza-bicyclo[3.2.1]octane-8-carboxylic acid tert-butyl ester, 3j Using an adaptation of the method described in Procedure 2, substituting endo-3-(4-chloro-2-hydroxyphenylamino)-8-aza-bicyclo[3.2.1]octane-8-carboxylic acid tert-butyl ester, 1j for the TFA salt of 3-hydroxy-4-(8-methyl-8-aza-bicyclo[3.2.1]oct-3-ylamino)-benzoic acid methyl ester, 1a, the title compound endo-3-(3-chlorophenoxazin-10-yl)-8-aza-bicyclo[3.2.1]octane-8-carboxylic acid tert-butyl ester, 3j was obtained.

Procedure 24

Endo-3-(3-Pyridin-3-yl-phenoxazin-10-yl)-8-aza-bicyclo[3.2.1]octane-8-carboxylic acid tert-butyl ester, 4j To a mixture of 3-pyridyl boronic acid (70.1 mg, 0.57 mmol), $Cp_2Fe(P-tBu_2)_2PdCl_2$ (62 mg, 0.095 mmol), potassium carbonate (88 mg, 0.63 mmol) was added a solution of endo-3-(3-chlorophenoxazin-10-yl)-8-aza-bicyclo[3.2.1]octane-8-carboxylic acid tert-butyl ester, 3j (135 mg, 0.317 mmol) in dioxane (3 mL, degassed with argon for 5 min prior to use). The mixture was heated to 120° C. for 30 min in a microwave (300 W). The mixture was allowed to cool to rt, water and ethyl acetate were added. The organic layer was separated, dried over $MgSO_4$, filtered, and evaporated to yield 195 mg of crude title compound endo-3-(3-pyridin-3-yl-phenoxazin-10-yl)-8-aza-bicyclo[3.2.1]octane-8-carboxylic acid tert-butyl ester, 4j. The material was used as such for the next reaction.

Procedure 25

Endo-10-(8-Aza-bicyclo[3.2.1]oct-3-yl)-3-pyridin-3-yl-10H-phenoxazine, 5j

The crude endo-3-(3-pyridin-3-yl-phenoxazin-10-yl)-8-aza-bicyclo[3.2.1]octane-8-carboxylic acid tert-butyl ester, 4j, obtained from the previous reaction, was treated with TFA (3 mL), and the mixture was stirred for 30 min at rt. The TFA was removed under a nitrogen stream, and the residue was purified via reverse phase HPLC (eluent gradient: 10% to 30% $CH_3CN$ in water containing 0.1% TFA). The desired fractions were combined, lyophilized, and dissolved in diethyl ether. The solution was washed with a saturated $NaHCO_3$ solution. The aqueous phase was washed with diethyl ether, and the combined organic phases were dried over $MgSO_4$, filtered, and evaporated to yield 58 mg (43% for 2 steps) of title compound endo-10-(8-aza-bicyclo[3.2.1]oct-3-yl)-3-pyridin-3-yl-10H-phenoxazine, 5j. MS m/z ($MH^+$) 370.2.

Endo-10-(8-Phenethyl-8-aza-bicyclo[3.2.1]oct-3-yl)-3-pyridin-3-yl-10H-phenoxazine, 6j Using an adaptation of the method described in Procedure 9, substituting endo-10-(8-aza-bicyclo[3.2.1]oct-3-yl)-3-pyridin-3-yl-10H-phenoxazine, 5j for the HCl salt of 10-(8-aza-bicyclo[3.2.1]oct-3-yl)-3-(1H-tetrazol-5-yl)-10H-phenoxazine, 4b and phenyl acetaldehyde for 2-pyridylcarboxaldehyde, the title compound endo-10-(8-phenethyl-8-aza-bicyclo[3.2.1]oct-3-yl)-3-pyridin-3-yl-10H-phenoxazine, 6j was obtained as a TFA salt. MS m/z ($MH^+$) 474.2.

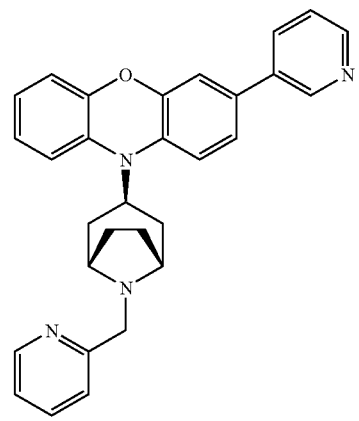

Endo-3-Pyridin-3-yl-10-(8-pyridin-2-ylmethyl-8-aza-bicyclo[3.2.1]oct-3-yl)-10H-phenoxazine, 7j Using an adaptation of the method described in Procedure 9, substituting endo-O-(8-aza-bicyclo[3.2.1]oct-3-yl)-3-pyridin-3-yl-10H-phenoxazine, 5j for the HCl salt of 10-(8-aza-bicyclo[3.2.1]oct-3-yl)-3-(1H-tetrazol-5-yl)-10H-phenoxazine, 4b and 2-pyridyl carboxaldehyde for 2-pyridylcarboxaldehyde, the title compound endo-3-pyridin-3-yl-10-(8-pyridin-2-ylmethyl-8-aza-bicyclo[3.2.1]oct-3-yl)-10H-phenoxazine, 7j was obtained as a TFA salt. MS m/z ($MH^+$) 461.2.

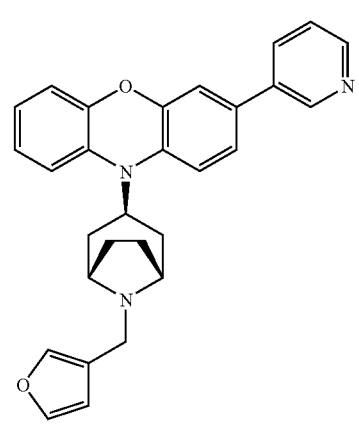

Endo-10-(8-Furan-3-ylmethyl-8-aza-bicyclo[3.2.1]oct-3-yl)-3-pyridin-3-yl-10H-phenoxazine, 8j Using an adaptation of the method described in Procedure 9, substituting endo-1-(8-aza-bicyclo[3.2.1]oct-3-yl)-3-pyridin-3-yl-10H-phenoxazine, 5j for the HCl salt of 10-(8-aza-bicyclo[3.2.1]oct-3-yl)-3-(1H-tetrazol-5-yl)-10H-phenoxazine, 4b and 3-furaldehyde for 2-pyridylcarboxaldehyde, the title compound endo-10-(8-furan-3-ylmethyl-8-aza-bicyclo[3.2.1]oct-3-yl)-3-pyridin-3-yl-10H-phenoxazine, 8j was obtained as a TFA salt. MS m/z (MH+) 450.2.

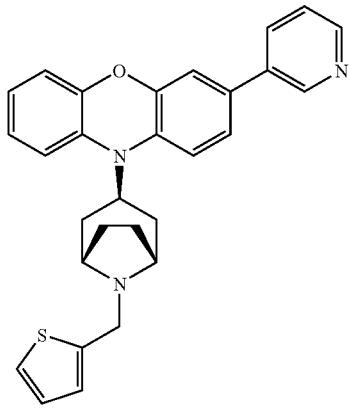

JNJ-38974819

Endo-3-Pyridin-3-yl-10-(8-thiophen-2-ylmethyl-8-aza-bicyclo[3.2.1]oct-3-yl)-10H-phenoxazine, 9j Using an adaptation of the method described in Procedure 9, substituting endo-10-(8-aza-bicyclo[3.2.1]oct-3-yl)-3-pyridin-3-yl-10H-phenoxazine, 5j for the HCl salt of 10-(8-aza-bicyclo[3.2.1]oct-3-yl)-3-(1H-tetrazol-5-yl)-10H-phenoxazine, 4b and 2-thiophene carboxaldehyde for 2-pyridylcarboxaldehyde, the title compound endo-3-pyridin-3-yl-10-(8-thiophen-2-ylmethyl-8-aza-bicyclo[3.2.1]oct-3-yl)-10H-phenoxazine, 9j was obtained as a TFA salt. MS m/z (MH+) 466.2.

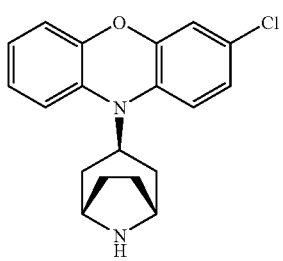

Endo-10-(8-Aza-bicyclo[3.2.1]oct-3-yl)-3-chloro-10H-phenoxazine, 10j

Using an adaptation of the method described in Procedure 25, substituting endo-3-(3-chloro-phenoxazin-10-yl)-8-aza-bicyclo[3.2.1]octane-8-carboxylic acid tert-butyl ester, 3j for endo-3-(3-pyridin-3-yl-phenoxazin-10-yl)-8-aza-bicyclo[3.2.1]octane-8-carboxylic acid tert-butyl ester, 4j, the title compound endo-10-(8-aza-bicyclo[3.2.1]-oct-3-yl)-3-chloro-10H-phenoxazine, 10j was obtained as a TFA salt after reverse phase HPLC purification (eluent: CH3CN in water containing 0.1% TFA). MS m/z (MH+) 327.1.

Example K

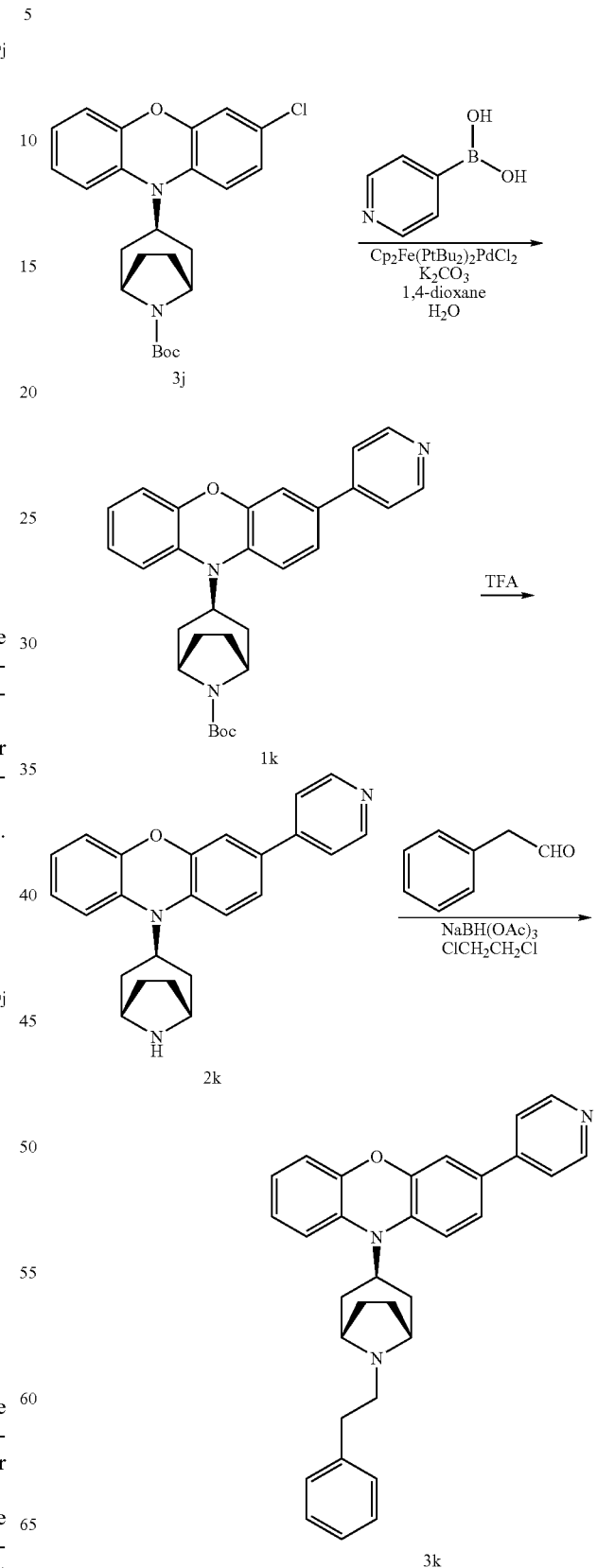

Endo-3-(3-Pyridin-4-yl-phenoxazin-10-yl)-8-aza-bicyclo[3.2.1]octane-8-carboxylic acid tert-butyl ester, 1k Using an adaptation of the method described in Procedure 24, substituting 4-pyridyl boronic acid for 3-pyridyl boronic acid, the title compound endo-3-(3-pyridin-4-yl-phenoxazin-10-yl)-8-aza-bicyclo[3.2.1]octane-8-carboxylic acid tert-butyl ester, 1k was obtained.

Endo-10-(8-Aza-bicyclo[3.2.1]oct-3-yl)-3-pyridin-4-yl-10H-phenoxazine, 2k

Using an adaptation of the method described in Procedure 25, substituting endo-3-(3-pyridin-4-yl-phenoxazin-10-yl)-8-aza-bicyclo[3.2.1]octane-8-carboxylic acid tert-butyl ester, 1k for endo-3-(3-pyridin-3-yl-phenoxazin-10-yl)-8-aza-bicyclo[3.2.1]-octane-8-carboxylic acid tert-butyl ester, 4j, the title compound endo-10-(8-aza-bicyclo[3.2.1]oct-3-yl)-3-pyridin-4-yl-10H-phenoxazine, 2k was obtained as a TFA salt after reverse phase HPLC purification (eluent gradient: 10% to 30% $CH_3CN$ in water containing 0.1% TFA). MS m/z ($MH^+$) 370.2.

Endo-10-(8-Phenethyl-8-aza-bicyclo[3.2.1]oct-3-yl)-3-pyridin-4-yl-10H-phenoxazine, 3k Using an adaptation of the method described in Procedure 9, substituting the TFA salt of endo-10-(8-aza-bicyclo[3.2.1]oct-3-yl)-3-pyridin-4-yl-10H-phenoxazine, 2k for the HCl salt of 10-(8-aza-bicyclo[3.2.1]oct-3-yl)-3-(1H-tetrazol-5-yl)-10H-phenoxazine, 4b and phenyl acetaldehyde for 2-pyridyl carboxaldehyde, the title compound endo-10-(8-phenethyl-8-aza-bicyclo[3.2.1]oct-3-yl)-3-pyridin-4-yl-10H-phenoxazine, 3k was obtained as a TFA salt. MS m/z ($MH^+$) 474.3.

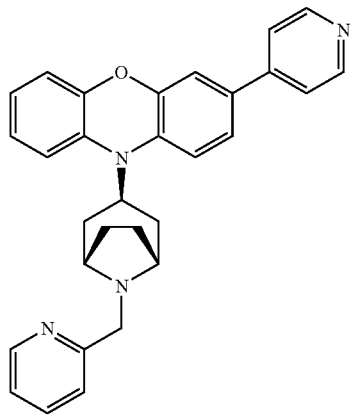

Endo-3-Pyridin-4-yl-10-(8-pyridin-2-ylmethyl-8-aza-bicyclo[3.2.1]oct-3-yl)-10H-phenoxazine, 4k Using an adaptation of the method described in Procedure 9, substituting the TFA salt of endo-10-(8-aza-bicyclo[3.2.1]oct-3-yl)-3-pyridin-4-yl-10H-phenoxazine, 2k for the HCl salt of 10-(8-aza-bicyclo[3.2.1]oct-3-yl)-3-(1H-tetrazol-5-yl)-10H-phenoxazine, 4b, the title compound endo-3-pyridin-4-yl-10-(8-pyridin-2-ylmethyl-8-aza-bicyclo[3.2.1]oct-3-yl)-10H-phenoxazine, 4k was obtained as a TFA salt. MS m/z ($MH^+$) 461.3.

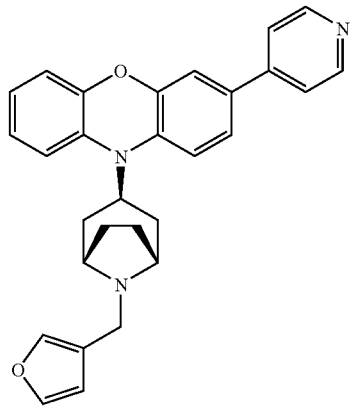

Endo-10-(8-Furan-3-ylmethyl-8-aza-bicyclo[3.2.1]oct-3-yl)-3-pyridin-4-yl-10H-phenoxazine, 5k Using an adaptation of the method described in Procedure 9, substituting the TFA salt of endo-10-(8-aza-bicyclo[3.2.1]oct-3-yl)-3-pyridin-4-yl-10H-phenoxazine, 2k for the HCl salt of 10-(8-aza-bicyclo[3.2.1]oct-3-yl)-3-(1H-tetrazol-5-yl)-10H-phenoxazine, 4b and 3-furaldehyde for 2-pyridylcarboxaldehyde, the title compound endo-10-(8-furan-3-ylmethyl-8-aza-bicyclo[3.2.1]oct-3-yl)-3-pyridin-4-yl-10H-phenoxazine, 5k was obtained as a TFA salt. MS m/z ($MH^+$) 450.3.

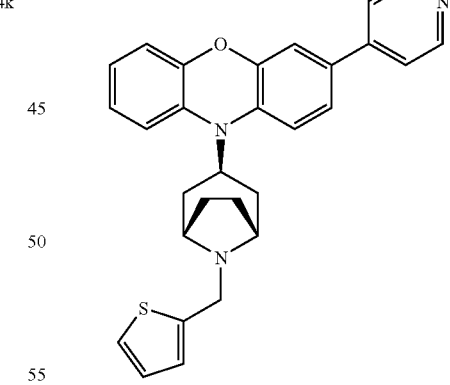

Endo-3-Pyridin-4-yl-10-(8-thiophen-2-ylmethyl-8-aza-bicyclo[3.2.1]oct-3-yl)-10H-phenoxazine, 6k Using an adaptation of the method described in Procedure 9, substituting the TFA salt of endo-10-(8-aza-bicyclo[3.2.1]oct-3-yl)-3-pyridin-4-yl-10H-phenoxazine, 2k for the HCl salt of 10-(8-aza-bicyclo[3.2.1]oct-3-yl)-3-(1H-tetrazol-5-yl)-10H-phenoxazine, 4b and 2-thiophene carboxaldehyde for 2-pyridylcarboxaldehyde, the title compound endo-3-pyridin-4-yl-10-(8-thiophen-2-ylmethyl-8-aza-bicyclo[3.2.1]oct-3-yl)-10H-phenoxazine, 6k was obtained as a TFA salt. MS m/z (MH⁺) 466.2.

Example L

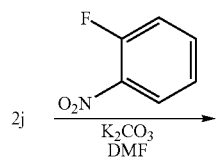

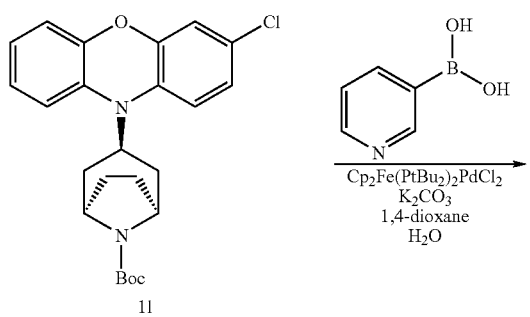

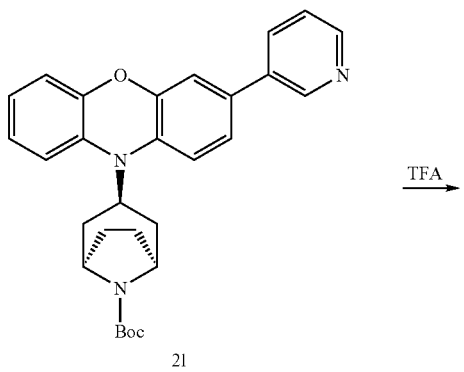

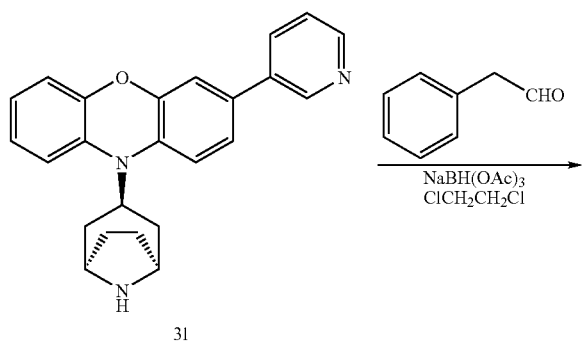

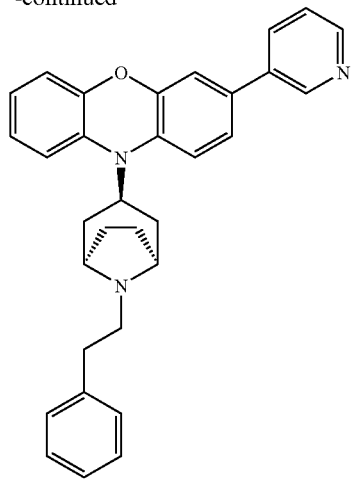

41

Exo-3-(3-Chlorophenoxazin-10-yl)-8-aza-bicyclo[3.2.1]octane-8-carboxylic acid tert-butyl ester, 1l Using an adaptation of the method described in Procedure 2, substituting exo-3-(4-chloro-2-hydroxyphenylamino)-8-aza-bicyclo[3.2.1]octane-8-carboxylic acid tert-butyl ester, 2j for the TFA salt of 3-hydroxy-4-(8-methyl-8-aza-bicyclo[3.2.1]oct-3-ylamino)-benzoic acid methyl ester, 1a, the title compound exo-3-(3-chlorophenoxazin-10-yl)-8-aza-bicyclo[3.2.1]octane-8-carboxylic acid tert-butyl ester, 1l was obtained.

Endo-3-(3-Pyridin-4-yl-phenoxazin-10-yl)-8-aza-bicyclo[3.2.1]octane-8-carboxylic acid tert-butyl ester, 2l Using an adaptation of the method described in Procedure 24, substituting exo-3-(3-chlorophenoxazin-10-yl)-8-aza-bicyclo[3.2.1]octane-8-carboxylic acid tert-butyl ester, 1l for endo-3-(3-chlorophenoxazin-10-yl)-8-aza-bicyclo[3.2.1]octane-8-carboxylic acid tert-butyl ester, 3j, the title compound 3-(3-pyridin-4-yl-phenoxazin-10-yl)-8-aza-bicyclo[3.2.1]octane-8-carboxylic acid tert-butyl ester, 2l was obtained.

Exo-3-(3-Pyridin-3-yl-phenoxazin-10-yl)-8-aza-bicyclo[3.2.1]octane-8-carboxylic acid tert-butyl ester, 3l Using an adaptation of the method described in Procedure 25, substituting exo-3-(3-pyridin-3-yl-phenoxazin-10-yl)-8-aza-bicyclo[3.2.1]octane-8-carboxylic acid tert-butyl ester, 2l for endo-3-(3-pyridin-3-yl-phenoxazin-10-yl)-8-aza-bicyclo[3.2.1]-octane-8-carboxylic acid tert-butyl ester, 4j, the title compound exo-3-(3-pyridin-3-yl-phenoxazin-10-yl)-8-aza-bicyclo[3.2.1]octane-8-carboxylic acid tert-butyl ester, 3l was obtained as a TFA salt after reverse phase HPLC purification (eluent gradient: 10% to 30% CH₃CN in water containing 0.1% TFA). MS m/z (MH⁺) 370.2.

Exo-10-(8-Phenethyl-8-aza-bicyclo[3.2.1]oct-3-yl)-3-pyridin-3-yl-10H-phenoxazine, 4l Using an adaptation of the method described in Procedure 9, substituting the TFA salt of exo-3-(3-pyridin-3-yl-phenoxazin-10-yl)-8-aza-bicyclo[3.2.1]octane-8-carboxylic acid tert-butyl ester, 3l for the HCl salt of 10-(8-aza-bicyclo[3.2.1]oct-3-yl)-3-(1H-tetrazol-5-yl)-10H-phenoxazine, 4b and phenyl acetaldehyde for 2-pyridyl carboxaldehyde, the title compound exo-10-(8-phenethyl-8-aza-bicyclo[3.2.1]oct-3-yl)-3-pyridin-3-yl-10H-phenoxazine, 4l was obtained as a TFA salt. MS m/z (MH+) 474.3.

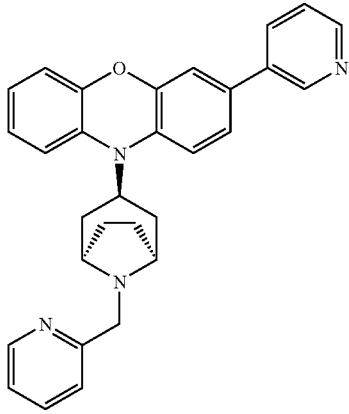

Exo-3-Pyridin-3-yl-10-(8-pyridin-2-ylmethyl-8-aza-bicyclo[3.2.1]oct-3-yl)-10H-phenoxazine, 5l Using an adaptation of the method described in Procedure 9, substituting the TFA salt of exo-3-(3-pyridin-3-yl-phenoxazin-10-yl)-8-aza-bicyclo[3.2.1]octane-8-carboxylic acid tert-butyl ester, 3l for the HCl salt of 10-(8-aza-bicyclo[3.2.1]oct-3-yl)-3-(1H-tetrazol-5-yl)-10H-phenoxazine, 4b, the title compound exo-3-pyridin-3-yl-10-(8-pyridin-2-ylmethyl-8-aza-bicyclo[3.2.1]oct-3-yl)-10H-phenoxazine, 5l was obtained as a TFA salt. MS m/z (MH+) 461.3.

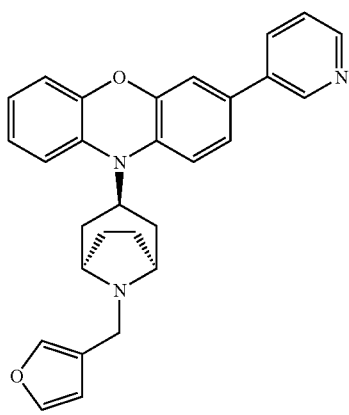

Exo-10-(8-Furan-3-ylmethyl-8-aza-bicyclo[3.2.1]oct-3-yl)-3-pyridin-3-yl-10H-phenoxazine, 6l Using an adaptation of the method described in Procedure 9, substituting the TFA salt of exo-3-(3-pyridin-3-yl-phenoxazin-10-yl)-8-aza-bicyclo[3.2.1]octane-8-carboxylic acid tert-butyl ester, 3l for the HCl salt of 10-(8-aza-bicyclo[3.2.1]oct-3-yl)-3-(1H-tetrazol-5-yl)-10H-phenoxazine, 4b and 3-furaldehyde for 2-pyridyl carboxaldehyde, the title compound exo-10-(8-furan-3-ylmethyl-8-aza-bicyclo[3.2.1]oct-3-yl)-3-pyridin-3-yl-10H-phenoxazine, 6l was obtained as a TFA salt. MS m/z (MH+) 450.2.

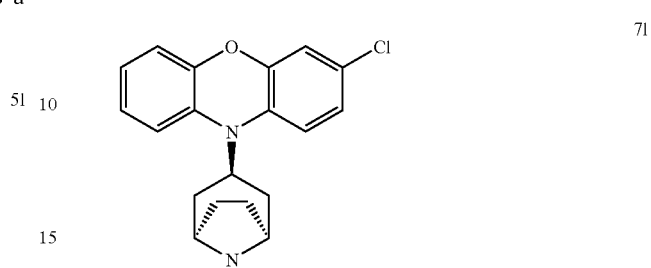

Exo-10-(8-Aza-bicyclo[3.2.1]oct-3-yl)-3-chloro-10H-phenoxazine, 7l

Using an adaptation of the method described in Procedure 25, substituting exo-3-(3-chloro-phenoxazin-10-yl)-8-aza-bicyclo[3.2.1]octane-8-carboxylic acid tert-butyl ester, 1l for endo-3-(3-pyridin-3-yl-phenoxazin-10-yl)-8-aza-bicyclo[3.2.1]octane-8-carboxylic acid tert-butyl ester, 4j, the title compound exo-10-(8-aza-bicyclo[3.2.1]-oct-3-yl)-3-chloro-10H-phenoxazine, 7l was obtained as a TFA salt after reverse phase HPLC purification (eluent: CH₃CN in water containing 0.1% TFA). MS m/z (MH+) 327.1.

Example M

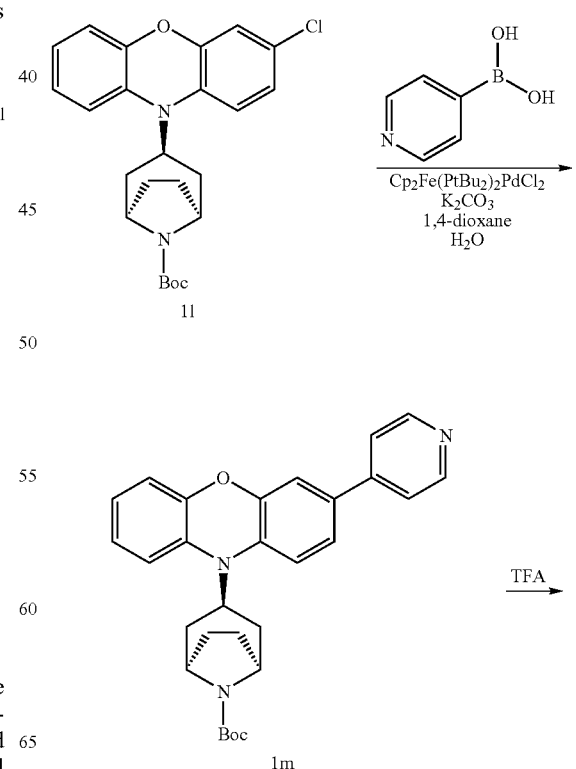

-continued

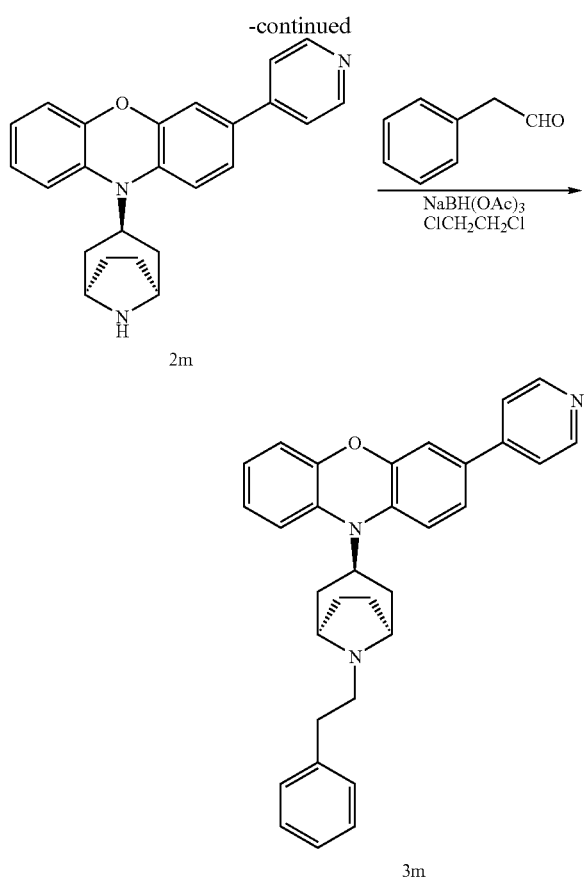

Exo-3-(3-Pyridin-4-yl-phenoxazin-10-yl)-8-aza-bicyclo[3.2.1]octane-8-carboxylic acid tert-butyl ester, 1m Using an adaptation of the method described in Procedure 24, substituting 4-pyridyl boronic acid for 3-pyridyl boronic acid, the title compound exo-3-(3-pyridin-4-yl-phenoxazin-10-yl)-8-aza-bicyclo[3.2.1]octane-8-carboxylic acid tert-butyl ester, 1m was obtained.

Exo-10-(8-Aza-bicyclo[3.2.1]oct-3-yl)-3-pyridin-4-yl-10H-phenoxazine, 2m

Using an adaptation of the method described in Procedure 25, substituting exo-3-(3-pyridin-4-yl-phenoxazin-10-yl)-8-aza-bicyclo[3.2.1]octane-8-carboxylic acid tert-butyl ester, 1l for endo-3-(3-pyridin-3-yl-phenoxazin-10-yl)-8-aza-bicyclo[3.2.1]-octane-8-carboxylic acid tert-butyl ester, 4j, the title compound exo-10-(8-aza-bicyclo[3.2.1]oct-3-yl)-3-pyridin-4-yl-10H-phenoxazine, 2m was obtained as a TFA salt after reverse phase HPLC purification (eluent gradient: 10% to 30% $CH_3CN$ in water containing 0.1% TFA). MS m/z ($MH^+$) 370.2.

Exo-10-(8-Phenethyl-8-aza-bicyclo[3.2.1]oct-3-yl)-3-pyridin-4-yl-10H-phenoxazine, 3m Using an adaptation of the method described in Procedure 9, substituting the TFA salt of exo-10-(8-aza-bicyclo[3.2.1]oct-3-yl)-3-pyridin-4-yl-10H-phenoxazine, 2m for the HCl salt of 10-(8-aza-bicyclo[3.2.1]oct-3-yl)-3-(1H-tetrazol-5-yl)-10H-phenoxazine, 4b and phenyl acetaldehyde for 2-pyridyl carboxaldehyde, the title compound exo-10-(8-phenethyl-8-aza-bicyclo[3.2.1]oct-3-yl)-3-pyridin-4-yl-10H-phenoxazine, 3m was obtained as a TFA salt. MS m/z ($MH^+$) 474.3.

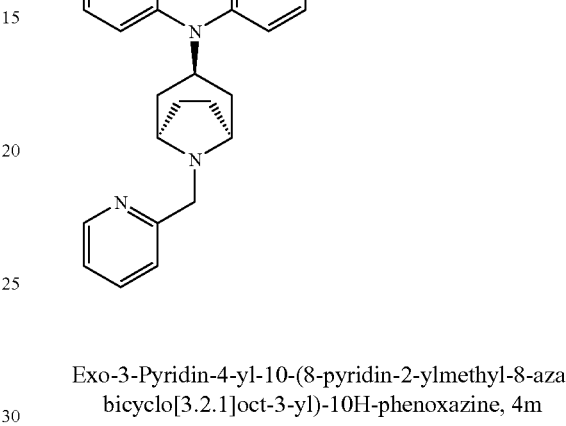

Exo-3-Pyridin-4-yl-10-(8-pyridin-2-ylmethyl-8-aza-bicyclo[3.2.1]oct-3-yl)-10H-phenoxazine, 4m Using an adaptation of the method described in Procedure 9, substituting the TFA salt of exo-10-(8-aza-bicyclo[3.2.1]oct-3-yl)-3-pyridin-4-yl-10H-phenoxazine, 2m for the HCl salt of 10-(8-aza-bicyclo[3.2.1]oct-3-yl)-3-(1H-tetrazol-5-yl)-10H-phenoxazine, 4b, the title compound exo-3-pyridin-4-yl-10-(8-pyridin-2-ylmethyl-8-aza-bicyclo[3.2.1]oct-3-yl)-10H-phenoxazine, 4m was obtained as a TFA salt. MS m/z ($MH^+$) 461.2.

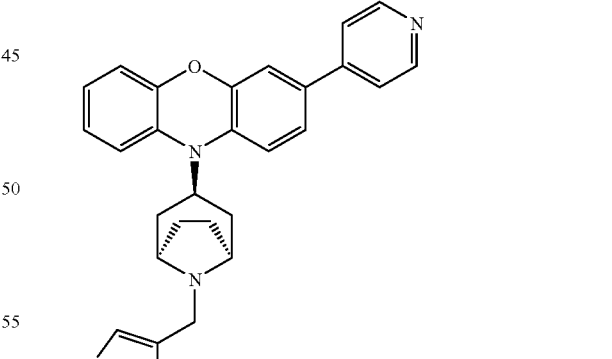

Exo-10-(8-Furan-3-ylmethyl-8-aza-bicyclo[3.2.1]oct-3-yl)-3-pyridin-4-yl-10H-phenoxazine, 5m Using an adaptation of the method described in Procedure 9, substituting the TFA salt of exo-10-(8-aza-bicyclo[3.2.1]oct-3-yl)-3-pyridin-4-yl-10H-phenoxazine, 2m for the HCl salt of 10-(8-aza-bicyclo[3.2.1]oct-3-yl)-3-(1H-tetrazol-5-yl)-10H-phenoxazine, 4b and 3-furaldehyde for 2-pyridyl carboxaldehyde, the title compound exo-10-(8-furan-3-ylmethyl-8-aza-bicyclo[3.2.1]oct-3-yl)-3-pyridin-4-yl-10H-phenoxazine, 5m was obtained as a TFA salt. MS m/z (MH$^+$) 450.2.

Example N

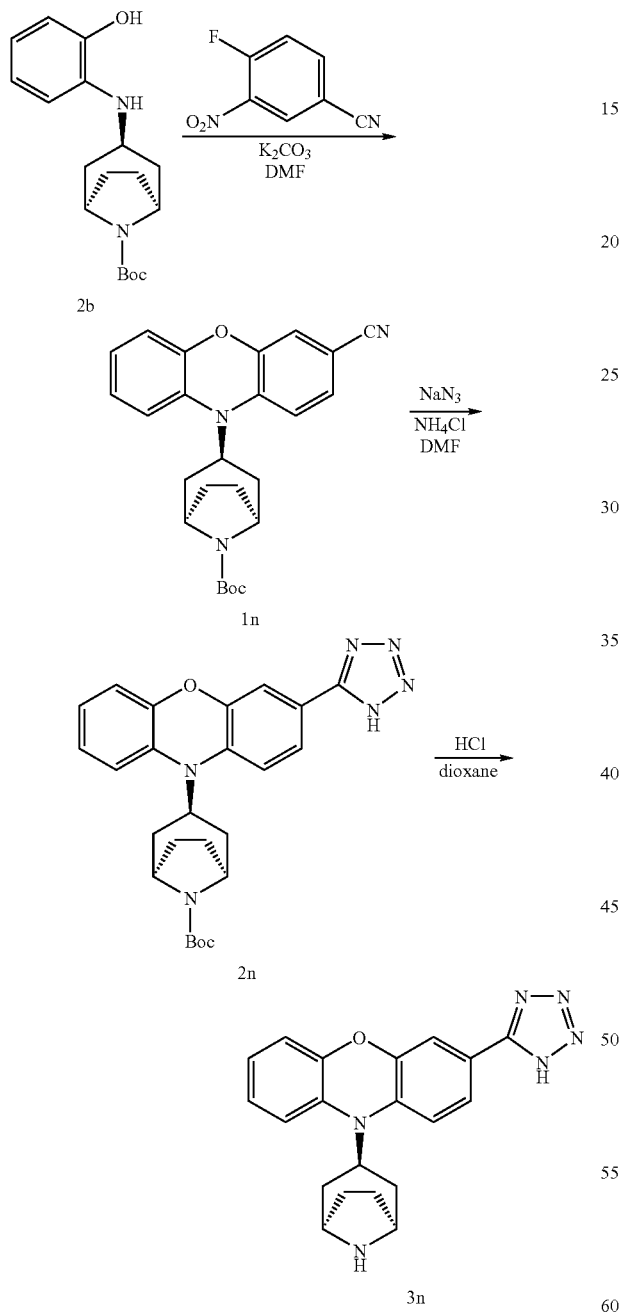

Exo-3-(3-Cyano-phenoxazin-10-yl)-8-aza-bicyclo[3.2.1]octane-8-carboxylic acid tert-butyl ester, 1n Using an adaptation of the method described in Procedure 6, substituting exo-3-(2-hydroxy-phenylamino)-8-aza-bicyclo[3.2.1]octane-8-carboxylic acid tert-butyl ester, 2b for endo-3-(2-hydroxy-phenylamino)-8-aza-bicyclo[3.2.1]octane-8-carboxylic acid tert-butyl ester, 1b, the title compound exo-3-(3-cyano-phenoxazin-10-yl)-8-aza-bicyclo[3.2.1]octane-8-carboxylic acid tert-butyl ester, 1n was obtained. MS m/z (MH$^+$) 439.9.

Exo-3-[3-(1H-Tetrazol-5-yl)-phenoxazin-10-yl]-8-aza-bicyclo[3.2.1]octane-8-carboxylic acid tert-butyl ester, 2n Using an adaptation of the method described in Procedure 7, substituting exo-3-(3-cyano-phenoxazin-10-yl)-8-aza-bicyclo[3.2.1]octane-8-carboxylic acid tert-butyl ester, 1n for endo-3-(3-cyano-phenoxazin-10-yl)-8-aza-bicyclo[3.2.1]octane-8-carboxylic acid tert-butyl ester, 3b, the title compound exo-3-[3-(1H-tetrazol-5-yl)-phenoxazin-10-yl]-8-aza-bicyclo[3.2.1]octane-8-carboxylic acid tert-butyl ester, 2n was obtained. MS m/z (MH$^+$) 460.9.

Exo-10-(8-Aza-bicyclo[3.2.1]oct-3-yl)-3-(1H-tetrazol-5-yl)-10H-phenoxazine, 3n

Using an adaptation of the method described in Procedure 8, substituting exo-3-[3-(1H-tetrazol-5-yl)-phenoxazin-10-yl]-8-aza-bicyclo[3.2.1]-octane-8-carboxylic acid tert-butyl ester, 2n for endo-3-[3-(1H-tetrazol-5-yl)-phenoxazin-10-yl]-8-aza-bicyclo[3.2.1]-octane-8-carboxylic acid tert-butyl ester, 4b, the title compound exo-10-(8-aza-bicyclo[3.2.1]oct-3-yl)-3-(1H-tetrazol-5-yl)-10H-phenoxazine, 3n was obtained as a TFA salt after purification via reverse phase HPLC (eluent: CH$_3$CN in water containing 0.1% TFA). MS m/z (MH$^+$) 360.9.

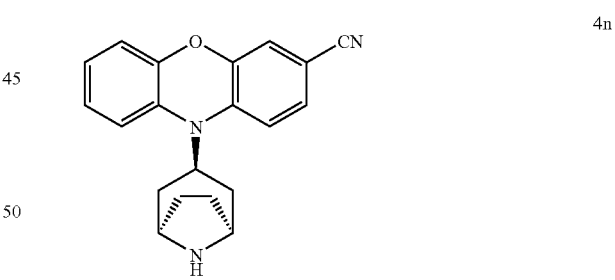

Exo-10-(8-Aza-bicyclo[3.2.1]oct-3-yl)-10H-phenoxazine-3-carbonitrile, 4n

Using an adaptation of the method described in Procedure 25, substituting exo-3-(3-cyano-phenoxazin-10-yl)-8-aza-bicyclo[3.2.1]octane-8-carboxylic acid tert-butyl ester, 1n for endo-3-(3-pyridin-3-yl-phenoxazin-10-yl)-8-aza-bicyclo[3.2.1]octane-8-carboxylic acid tert-butyl ester, 4j, and using a 1:1 solution of TFA;CH$_2$Cl$_2$ instead of neat TFA, the title compound exo-10-(8-aza-bicyclo[3.2.1]oct-3-yl)-10H-phenoxazine-3-carbonitrile, 4n was obtained as a TFA salt after reverse phase HPLC purification (eluent gradient: 20% to 45% CH₃CN in water containing 0.1% TFA). MS m/z (MH⁺) 317.9.

Example O

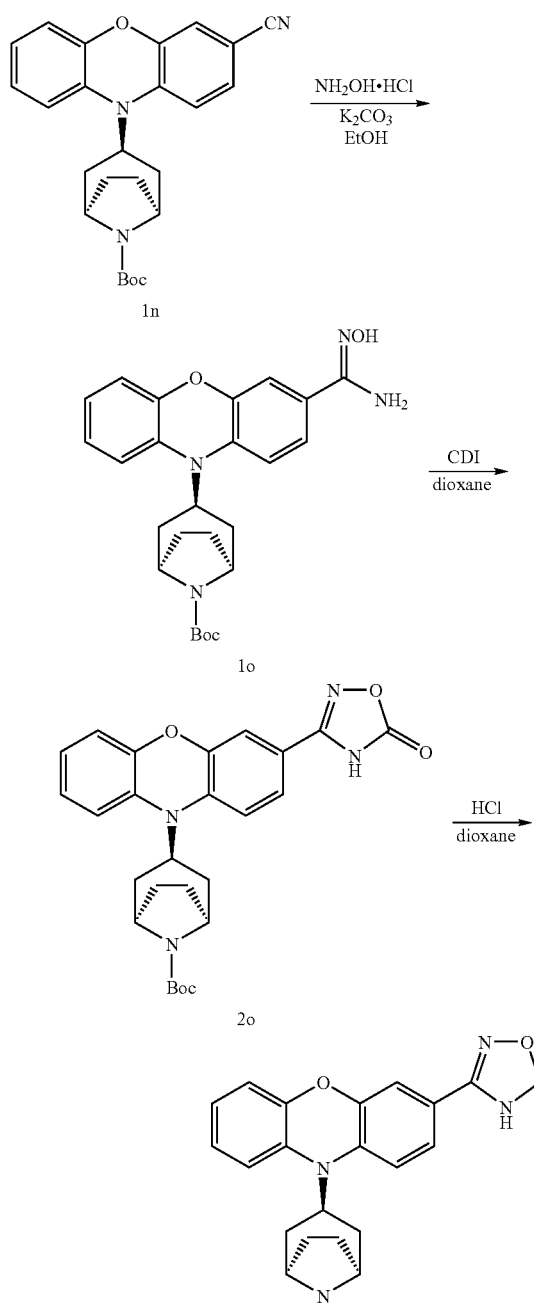

Exo-3-[3-(N-Hydroxycarbamimidoyl)-phenoxazin-10-yl]-8-aza-bicyclo[3.2.1]octane-8-carboxylic acid tert-butyl ester, 1o Using an adaptation of the method described in Procedure 11, substituting exo-3-(3-cyano-phenoxazin-10-yl)-8-aza-bicyclo[3.2.1]octane-8-carboxylic acid tert-butyl ester, 1n for endo-3-(3-cyano-phenoxazin-10-yl)-8-aza-bicyclo[3.2.1]octane-8-carboxylic acid tert-butyl ester, 3b, the title compound exo-3-[3-(N-hydroxycarbamimidoyl)-phenoxazin-10-yl]-8-aza-bicyclo[3.2.1]octane-8-carboxylic acid tert-butyl ester, 1o was obtained. MS m/z (MH⁺) 450.9.

Exo-3-[3-(5-Oxo-4,5-dihydro-[1,2,4]oxadiazol-3-yl)-phenoxazin-10-yl]-8-aza-bicyclo[3.2.1]octane-8-carboxylic acid tert-butyl ester, 2o Using an adaptation of the method described in Procedure 12, substituting exo-3-[3-(N-hydroxycarbamimidoyl)-phenoxazin-10-yl]-8-aza-bicyclo[3.2.1]octane-8-carboxylic acid tert-butyl ester, 1o for the mixture of endo-3-[3-(N-hydroxycarbamimidoyl)-phenoxazin-10-yl]-8-aza-bicyclo[3.2.1]octane-8-carboxylic acid tert-butyl ester, 1d and endo-3-(3-carbamoyl-phenoxazin-10-yl)-8-aza-bicyclo[3.2.1]octane-8-carboxylic acid tert-butyl ester, 2d, the title compound exo-3-[3-(5-oxo-4,5-dihydro-[1,2,4]oxadiazol-3-yl)-phenoxazin-10-yl]-8-aza-bicyclo[3.2.1]octane-8-carboxylic acid tert-butyl ester, 2o was obtained.

Exo-3-[10-(8-Aza-bicyclo[3.2.1]oct-3-yl)-10H-phenoxazin-3-yl]-4H-[1,2,4]oxadiazol-5-one, 3o Using an adaptation of Procedure 8, and substituting exo-3-[3-(5-oxo-4,5-dihydro-[1,2,4]oxadiazol-3-yl)-phenoxazin-10-yl]-8-aza-bicyclo[3.2.1]octane-8-carboxylic acid tert-butyl ester, 2o for endo-3-[3-(1H-tetrazol-5-yl)-phenoxazin-10-yl]-8-aza-bicyclo[3.2.1]-octane-8-carboxylic acid tert-butyl ester, 4b, the title compound exo-3-[10-(8-aza-bicyclo[3.2.1]oct-3-yl)-10H-phenoxazin-3-yl]-4H-[1,2,4]oxadiazol-5-one, 3o was obtained as TFA salt after purification via reverse phase HPLC (eluent gradient: 20% to 45% CH₃CN in water containing 0.1% TFA). MS m/z (MH⁺) 376.8.

Example P

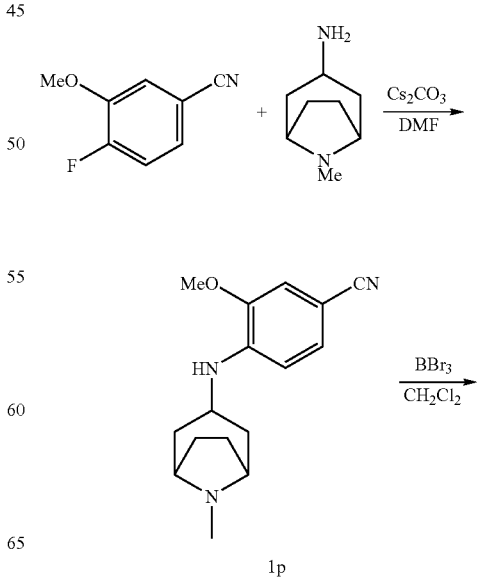

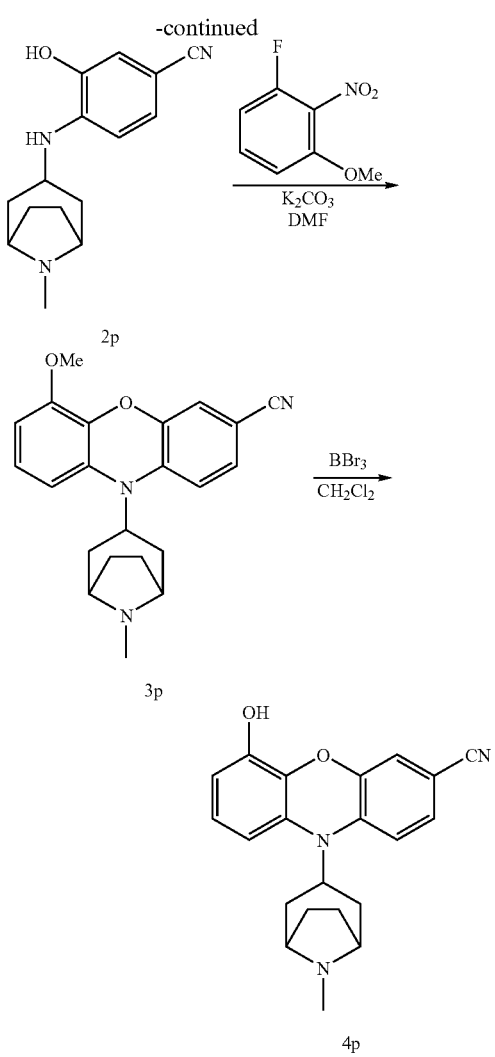

3-Methoxy-4-(8-methyl-8-aza-bicyclo[3.2.1]oct-3-ylamino)-benzonitrile, 1p

Using an adaptation of Procedure 2, substituting 8-methyl-8-aza-bicyclo[3.2.1]oct-3-ylamine for the TFA salt of 3-hydroxy-4-(8-methyl-8-aza-bicyclo[3.2.1]oct-3-ylamino)-benzoic acid methyl ester, 1a, 1-fluoro-3-methoxy-2-nitrobenzene, 1e for 2-fluoronitrobenzene, and cesium carbonate for potassium carbonate, the title compound 3-methoxy-4-(8-methyl-8-aza-bicyclo[3.2.1]oct-3-ylamino)-benzonitrile, 1p was obtained as TFA salt and as a mixture of endo and exo isomers after purification via reverse phase HPLC (eluent gradient: 20% to 45% CH$_3$CN in water containing 0.1% TFA). MS m/z=272 (M+1).

3-Hydroxy-4-(8-methyl-8-aza-bicyclo[3.2.1]oct-3-ylamino)-benzonitrile, 2p

Using an adaptation of Procedure 13, substituting the TFA salt of 3-methoxy-4-(8-methyl-8-aza-bicyclo[3.2.1]oct-3-ylamino)-benzonitrile, 1p for the TFA salt of 6-methoxy-10-(8-phenethyl-8-aza-bicyclo[3.2.1]oct-3-yl)-10H-phenoxazine-3-carboxylic acid diethylamide, 6e, the title compound 3-hydroxy-4-(8-methyl-8-aza-bicyclo[3.2.1]oct-3-ylamino)-benzonitrile, 2p was obtained as TFA salt and as a mixture of endo and exo isomers after purification via reverse phase HPLC (eluent gradient: 20% to 45% CH$_3$CN in water containing 0.1% TFA). MS m/z=258 (M+1).

6-Methoxy-10-(8-methyl-8-aza-bicyclo[3.2.1]oct-3-yl)-10H-phenoxazine-3-carbonitrile, 3p Using an adaptation of Procedure 2, substituting the TFA salt of 3-hydroxy-4-(8-methyl-8-aza-bicyclo[3.2.1]oct-3-ylamino)-benzonitrile, 2p for the TFA salt of 3-hydroxy-4-(8-methyl-8-aza-bicyclo[3.2.1]oct-3-ylamino)-benzoic acid methyl ester, 1a, and 1-fluoro-3-methoxy-2-nitrobenzene, 1e for 2-fluoronitrobenzene, the title compound 6-methoxy-10-(8-methyl-8-aza-bicyclo[3.2.1]oct-3-yl)-10H-phenoxazine-3-carbonitrile, 3p was obtained as TFA salt and as a mixture of endo and exo isomers after purification via reverse phase HPLC (eluent gradient: 20% to 45% CH$_3$CN in water containing 0.1% TFA). MS m/z=362 (M+1).

6-Hydroxy-10-(8-methyl-8-aza-bicyclo[3.2.1]oct-3-yl)-10H-phenoxazine-3-carbonitrile, 4p Using an adaptation of Procedure 13, substituting the TFA salt of 6-methoxy-10-(8-methyl-8-aza-bicyclo[3.2.1]oct-3-yl)-10H-phenoxazine-3-carbonitrile, 3p for the TFA salt of 6-methoxy-10-(8-phenethyl-8-aza-bicyclo[3.2.1]oct-3-yl)-10H-phenoxazine-3-carboxylic acid diethylamide, 6e, the title compound 6-hydroxy-10-(8-methyl-8-aza-bicyclo[3.2.1]oct-3-yl)-10H-phenoxazine-3-carbonitrile, 4p was obtained as TFA salt and as a mixture of endo and exo isomers after purification via reverse phase HPLC (eluent gradient: 20% to 45% CH$_3$CN in water containing 0.1% TFA). MS m/z=348 (M+1).

Example Q

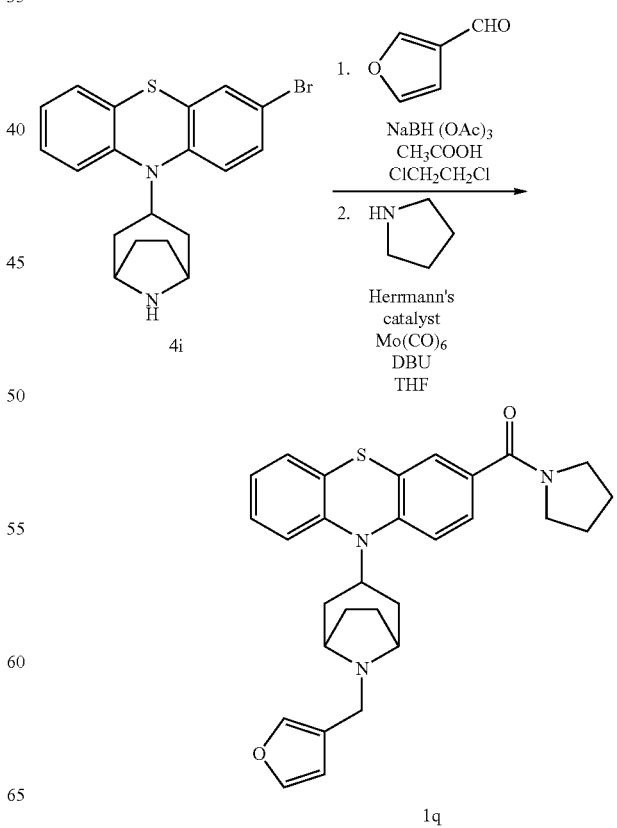

Procedure 26

[10-(8-Furan-3-ylmethyl-8-aza-bicyclo[3.2.1]oct-3-yl)-10H-phenothiazin-3-yl]-pyrrolidin-1-yl-methanone, 1q To a solution of a mixture of endo and exo isomers of 3-bromo-10-piperidin-4-yl-10H-phenothiazine, 4i (15 mg, 0.04 mmol) in dichloroethane (0.4 mL) were added 3-furaldehyde (10 µL, 0.12 mmol), acetic acid (5 µL) and sodium triacetoxy-borohydride (17 mg, 0.08 mmol). The mixture was allowed to stir at rt for 16 h, and quenched with a 2N NaOH solution (200 µL). The mixture was absorbed onto a 1 g SPE cartridge and eluted (eluent: 10% methanol in ethyl acetate containing 1% triethylamine). The eluent (~15 mL) was collected and evaporated. The residue was dissolved in THF (0.4 mL), and pyrrolidine (19 µL, 0.15 mmol), Mo(CO)$_6$ (16 mg, 0.06 mmol), Herrmann's catalyst (6 mg, 0.006 mmol), and DBU (27 µL, 0.18 mmol) were added. The mixture was irradiated in a microwave oven at 150° C. for 15 min. The mixture was evaporated, and the residue was purified via reverse phase HPLC (eluent gradient: CH$_3$CN in water containing 0.1% TFA) to yield [10-(8-furan-3-ylmethyl-8-aza-bicyclo[3.2.1]oct-3-yl)-10H-phenothiazin-3-yl]-pyrrolidin-1-yl-methanone, 1q as a TFA salt and as a mixture of endo and exo isomers. MS m/z (MH$^+$) 486.2.

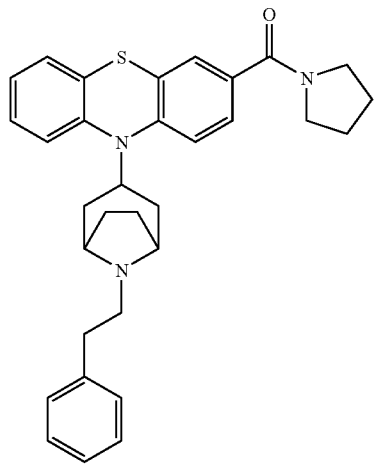

[10-(8-Phenethyl-8-aza-bicyclo[3.2.1]oct-3-yl)-10H-phenothiazin-3-yl]-pyrrolidin-1-yl-methanone, 2q Using an adaptation of Procedure 26, substituting phenyl acetaldehyde for 3-furaldehyde, the title compound [10-(8-phenethyl-8-aza-bicyclo[3.2.1]oct-3-yl)-10H-phenothiazin-3-yl]-pyrrolidin-1-yl-methanone, 2q was obtained as TFA salt and as a mixture of endo and exo isomers after purification via reverse phase HPLC (eluent gradient: 20% to 45% CH$_3$CN in water containing 0.1% TFA). MS m/z=510.3 (M+1).

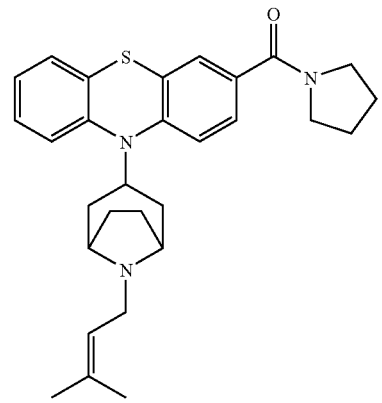

{10-[8-(3-Methyl-but-2-enyl)-8-aza-bicyclo[3.2.1]oct-3-yl]-10H-phenothiazin-3-yl}-pyrrolidin-1-yl-methanone, 3q Using an adaptation of Procedure 26, substituting 3-methyl-but-2-enal for 3-furaldehyde, the title compound {10-[8-(3-methyl-but-2-enyl)-8-aza-bicyclo[3.2.1]oct-3-yl]-10H-phenothiazin-3-yl}-pyrrolidin-1-yl-methanone, 3q was obtained as TFA salt and as a mixture of endo and exo isomers after purification via reverse phase HPLC (eluent gradient: 20% to 45% CH$_3$CN in water containing 0.1% TFA). MS m/z=474.2 (M+1).

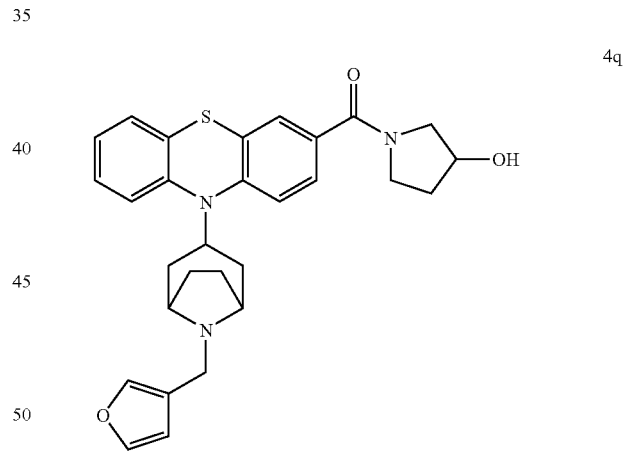

[10-(8-Furan-3-ylmethyl-8-aza-bicyclo[3.2.1]oct-3-yl)-10H-phenothiazin-3-yl]-(3-hydroxy-pyrrolidin-1-yl)-methanone, 4q Using an adaptation of Procedure 26, substituting 3-hydroxypyrrolidine for pyrrolidine, the title compound [10-(8-furan-3-ylmethyl-8-aza-bicyclo[3.2.1]oct-3-yl)-10H-phenothiazin-3-yl]-(3-hydroxy-pyrrolidin-1-yl)-methanone, 4q was obtained as TFA salt and as a mixture of endo and exo isomers after purification via reverse phase HPLC (eluent gradient: 20% to 45% CH$_3$CN in water containing 0.1% TFA). MS m/z=502.2 (M+1).

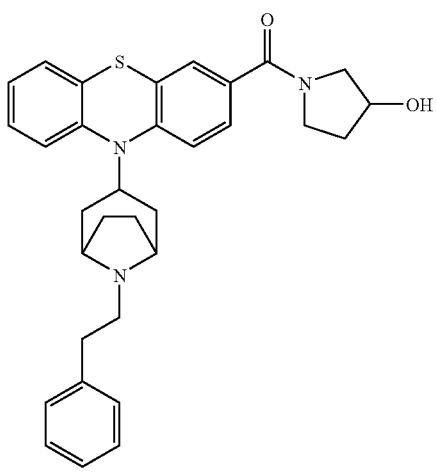

(3-Hydroxy-pyrrolidin-1-yl)-[10-(8-phenethyl-8-aza-bicyclo[3.2.1]oct-3-yl)-10H-phenothiazin-3-yl]-methanone, 5q Using an adaptation of Procedure 26, substituting phenyl acetaldehyde for 3-furaldehyde and 3-hydroxypyrrolidine for pyrrolidine, the title compound (3-hydroxy-pyrrolidin-1-yl)-[10-(8-phenethyl-8-aza-bicyclo[3.2.1]oct-3-yl)-10H-phenothiazin-3-yl]-methanone, 5q was obtained as TFA salt and as a mixture of endo and exo isomers after purification via reverse phase HPLC (eluent gradient: 20% to 45% CH₃CN in water containing 0.1% TFA). MS m/z=526.2 (M+1).

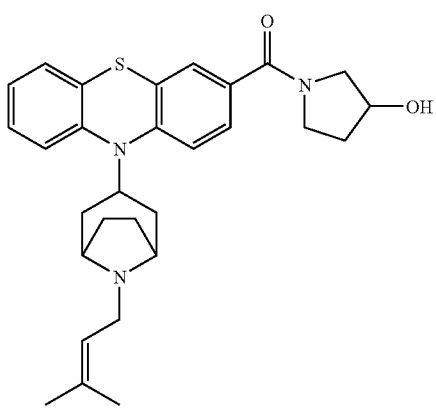

{10-[8-(3-Methyl-but-2-enyl)-8-aza-bicyclo[3.2.1]oct-3-yl]-10H-phenothiazin-3-yl}-(3-methyl-pyrrolidin-1-yl)-methanone, 6q Using an adaptation of Procedure 26, substituting 3-methyl-but-2-enal for 3-furaldehyde and 3-hydroxypyrrolidine for pyrrolidine, the title compound {10-[8-(3-methyl-but-2-enyl)-8-aza-bicyclo[3.2.1]oct-3-yl]-10H-phenothiazin-3-yl}-(3-methyl-pyrrolidin-1-yl)-methanone, 6q was obtained as TFA salt and as a mixture of endo and exo isomers after purification via reverse phase HPLC (eluent gradient: 20% to 45% CH₃CN in water containing 0.1% TFA). MS m/z=490.2 (M+1).

Example R

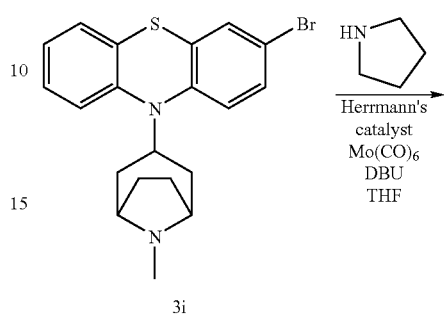

Procedure 27

[10-(8-Methyl-8-aza-bicyclo[3.2.1]oct-3-yl)-10H-phenothiazin-3-yl]-pyrrolidin-1-yl-methanone, 1r To a solution of 3-bromo-10-(8-methyl-8-aza-bicyclo[3.2.1]oct-3-yl)-10H-phenothiazine, 3i (15 mg, 0.04 mmol) in THF (0.3 mL) was added pyrrolidine (12 µL, 0.15 mmol), Mo(CO)₆ (16 mg, 0.06 mmol), Herrmann's catalyst (6 mg, 0.006 mmol), and DBU (27 µL, 0.18 mmol), and the mixture was irradiated in a microwave oven at 150° C. for 15 min. The mixture was evaporated, and the residue was purified via reverse phase HPLC (eluent gradient: CH₃CN in water containing 0.1% TFA) to yield [10-(8-methyl-8-aza-bicyclo[3.2.1]oct-3-yl)-10H-phenothiazin-3-yl]-pyrrolidin-1-yl-methanone, 1r as a TFA salt and a mixture of endo and exo isomers. MS m/z (MH⁺) 420.2.

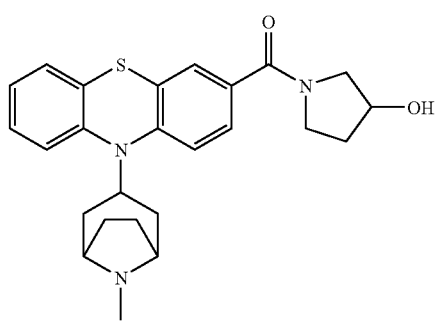

(3-Hydroxy-pyrrolidin-1-yl)-[10-(8-methyl-8-aza-bicyclo[3.2.1]oct-3-yl)-10H-phenothiazin-3-yl]-methanone, 2r Using an adaptation of Procedure 27, substituting 3-hydroxypyrrolidine for pyrrolidine, the title compound (3-hydroxy-pyrrolidin-1-yl)-[10-(8-methyl-8-aza-bicyclo[3.2.1]oct-3-yl)-10H-phenothiazin-3-yl]-methanone, 2r was obtained as TFA salt and as a mixture of endo and exo isomers after purification via reverse phase HPLC (eluent gradient: 20% to 45% CH$_3$CN in water containing 0.1% TFA). MS m/z=436.2 (M+1).

10-(8-Methyl-8-aza-bicyclo[3.2.1]oct-3-yl)-10H-phenothiazine-3-carboxylic acid ethylamide, 3r Using an adaptation of Procedure 27, substituting ethylamine for pyrrolidine, the title compound 10-(8-methyl-8-aza-bicyclo[3.2.1]oct-3-yl)-10H-phenothiazine-3-carboxylic acid ethylamide, 3r was obtained as TFA salt and as a mixture of endo and exo isomers after purification via reverse phase HPLC (eluent gradient: 20% to 45% CH$_3$CN in water containing 0.1% TFA). MS m/z=394.2 (M+1).

Example T

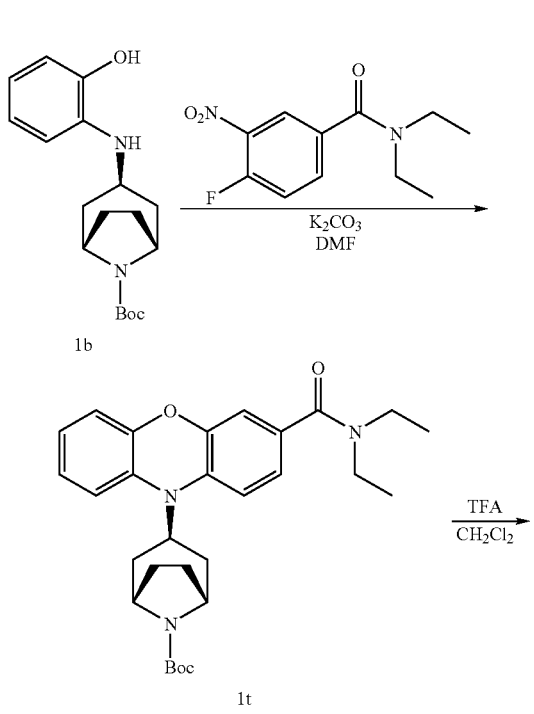

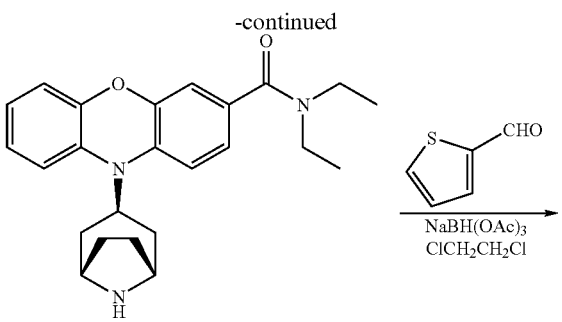

Endo-3-(3-Diethylcarbamoyl-phenoxazin-10-yl)-8-aza-bicyclo[3.2.1]octane-8-carboxylic acid tert-butyl ester, 1t Using an adaptation of Procedure 6, and substituting endo-3-(2-hydroxy-phenylamino)-8-aza-bicyclo[3.2.1]octane-8-carboxylic acid tert-butyl ester, 1b for 3-(2-hydroxy-phenylamino)-8-aza-bicyclo[3.2.1]octane-8-carboxylic acid tert-butyl ester, 1b, the title compound endo-3-(3-diethylcarbamoyl-phenoxazin-10-yl)-8-aza-bicyclo[3.2.1]octane-8-carboxylic acid tert-butyl ester, 1t was obtained. The crude material was used as such in the next reaction.

Endo-10-(8-Aza-bicyclo[3.2.1]oct-3-yl)-10H-phenoxazine-3-carboxylic acid diethylamide, 2t Using an adaptation of Procedure 25, substituting endo-3-(3-diethylcarbamoyl-phenoxazin-10-yl)-8-aza-bicyclo[3.2.1]octane-8-carboxylic acid tert-butyl ester, 1t for endo-3-(3-pyridin-3-yl-phenoxazin-10-yl)-8-aza-bicyclo[3.2.1]octane-8-carboxylic acid tert-butyl ester, 4j, and using a 25% solution of TFA in methylene chloride instead of neat TFA, the title compound endo-10-(8-aza-bicyclo[3.2.1]oct-3-yl)-10H-phenoxazine-3-carboxylic acid diethylamide, 2t was obtained as a TFA salt after purification via reverse phase HPLC (eluent: CH$_3$CN in water containing 0.1% TFA). MS m/z (MH$^+$) 392.1.

Endo-10-(8-Thiophen-2-ylmethyl-8-aza-bicyclo[3.2.1]oct-3-yl)-10H-phenoxazine-3-carboxylic acid diethylamide, 3t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, thiophene-2-carboxaldehyde for 2-pyridyl carboxaldehyde, tetrabutylammonium triacetoxyborohydride for sodium triacetoxyborohydride, and tetrahydrofuran for dichloroethane, the title compound endo-10-(8-thiophen-2-ylmethyl-8-aza-bicyclo[3.2.1]oct-3-yl)-10H-phenoxazine-3-carboxylic acid diethylamide, 3t was obtained as a TFA salt after purification via reverse phase HPLC (eluent: CH$_3$CN in water containing 0.1% TFA). MS m/z (MH$^+$) 488.1.

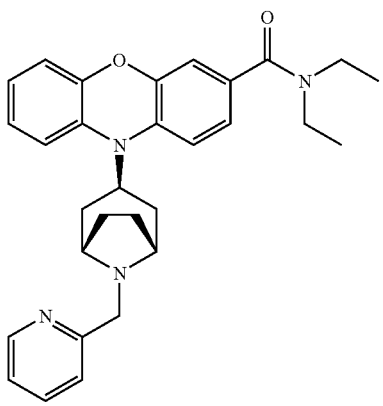

Endo-10-(8-Pyridin-2-ylmethyl-8-aza-bicyclo[3.2.1]oct-3-yl)-10H-phenoxazine-3-carboxylic acid diethylamide, 4t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, tetrabutylammonium triacetoxyborohydride for sodium triacetoxyborohydride, and tetrahydrofuran for dichloroethane, the title compound endo-10-(8-pyridin-2-ylmethyl-8-aza-bicyclo[3.2.1]oct-3-yl)-10H-phenoxazine-3-carboxylic acid diethylamide, 4t was obtained as a TFA salt after purification via reverse phase HPLC (eluent: CH$_3$CN in water containing 0.1% TFA). MS m/z (MH$^+$) 483.1.

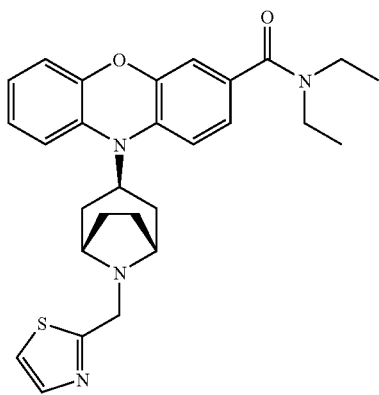

Endo-10-(8-Thiazol-2-ylmethyl-8-aza-bicyclo[3.2.1]oct-3-yl)-10H-phenoxazine-3-carboxylic acid diethylamide, 5t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, thiazol-2-ylmethyl carboxaldehyde for 2-pyridyl carboxaldehyde, tetrabutylammonium triacetoxyborohydride for sodium triacetoxyborohydride, and tetrahydrofuran for dichloroethane, the title compound endo-10-(8-thiazol-2-ylmethyl-8-aza-bicyclo[3.2.1]oct-3-yl)-10H-phenoxazine-3-carboxylic acid diethylamide, 5t was obtained as a TFA salt after purification via reverse phase HPLC (eluent: CH$_3$CN in water containing 0.1% TFA). MS m/z (MH$^+$) 489.1.

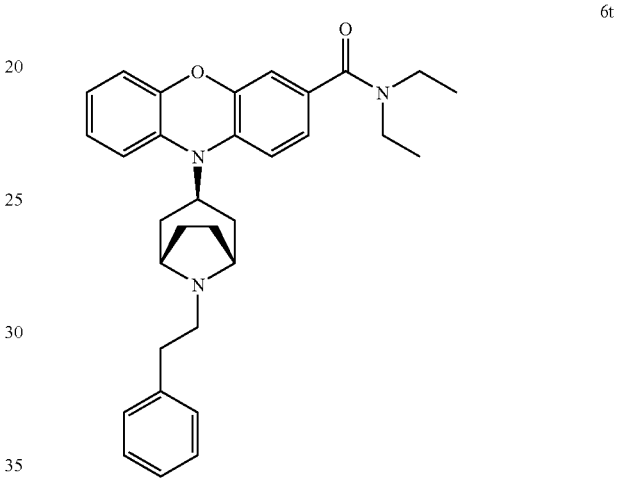

Endo-10-(8-Phenethyl-8-aza-bicyclo[3.2.1]oct-3-yl)-10H-phenoxazine-3-carboxylic acid diethylamide, 6t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, phenyl acetaldehyde for 2-pyridyl carboxaldehyde, tetrabutylammonium triacetoxy-borohydride for sodium triacetoxyborohydride, and tetrahydrofuran for dichloro-ethane, the title compound endo-10-(8-phenethyl-8-aza-bicyclo[3.2.1]oct-3-yl)-10H-phenoxazine-3-carboxylic acid diethylamide, 6t was obtained as a TFA salt after purification via reverse phase HPLC (eluent: CH$_3$CN in water containing 0.1% TFA).

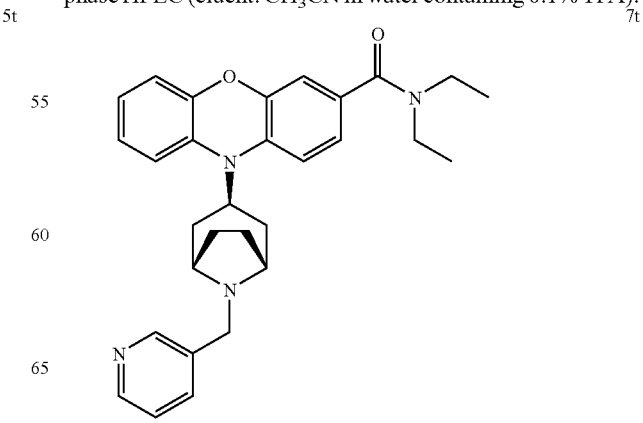

Endo-10-(8-Pyridin-3-ylmethyl-8-aza-bicyclo[3.2.1]oct-3-yl)-10H-phenoxazine-3-carboxylic acid diethylamide, 7t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, 3-pyridyl carboxaldehyde for 2-pyridyl carboxaldehyde, tetrabutylammonium triacetoxy-borohydride for sodium triacetoxyborohydride, and tetrahydrofuran for dichloro-ethane, the title compound endo-10-(8-pyridin-3-ylmethyl-8-aza-bicyclo[3.2.1]oct-3-yl)-10H-phenoxazine-3-carboxylic acid diethylamide, 7t was obtained as a TFA salt after purification via reverse phase HPLC (eluent: CH$_3$CN in water containing 0.1% TFA). MS m/z (MH$^+$) 483.1.

8t

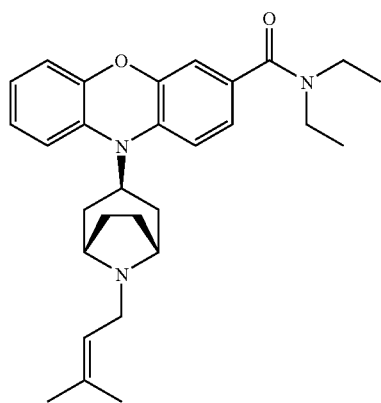

Endo-10-[8-(3-Methyl-but-2-enyl)-8-aza-bicyclo[3.2.1]oct-3-yl]-10H-phenoxazine-3-carboxylic acid diethylamide Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, 3-methyl-but-2-enyl carboxaldehyde for 2-pyridyl carboxaldehyde, tetrabutylammonium triacetoxyborohydride for sodium triacetoxyborohydride, and tetrahydrofuran for dichloroethane, the title compound endo-10-[8-(3-methyl-but-2-enyl)-8-aza-bicyclo[3.2.1]oct-3-yl]-10H-phenoxazine-3-carboxylic acid diethylamide, 8t was obtained as a TFA salt after purification via reverse phase HPLC (eluent: CH$_3$CN in water containing 0.1% TFA). MS m/z (MH$^+$) 460.1.

9t

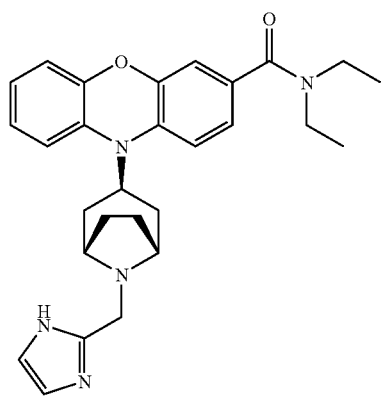

Endo-10-[8-(1H-Imidazol-2-ylmethyl)-8-aza-bicyclo[3.2.1]oct-3-yl]-10H-phenoxazine-3-carboxylic acid diethylamide, 9t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, 1H-imidazol-2-ylmethyl carboxaldehyde for 2-pyridyl carboxaldehyde, tetrabutylammonium triacetoxyborohydride for sodium triacetoxyborohydride, and tetrahydrofuran for dichloroethane, the title compound endo-10-[8-(1H-imidazol-2-ylmethyl)-8-aza-bicyclo[3.2.1]oct-3-yl]-10H-phenoxazine-3-carboxylic acid diethylamide, 9t was obtained as a TFA salt after purification via reverse phase HPLC (eluent: CH$_3$CN in water containing 0.1% TFA). MS m/z (MH$^+$) 472.1.

10t

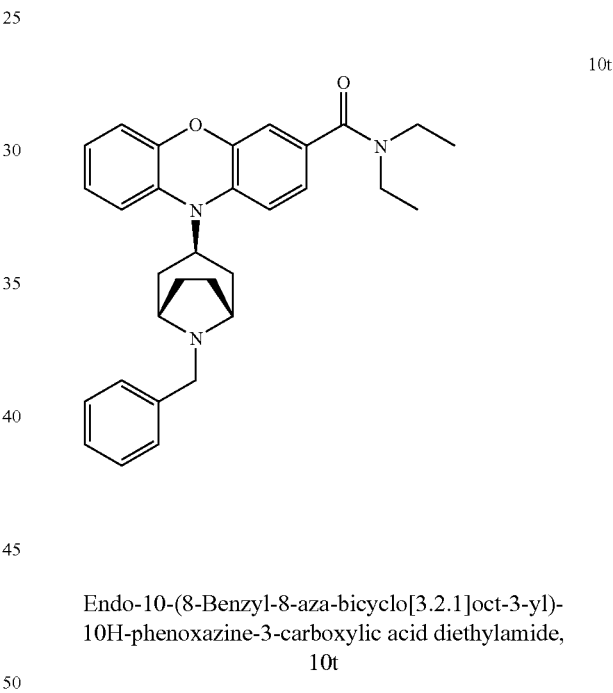

Endo-10-(8-Benzyl-8-aza-bicyclo[3.2.1]oct-3-yl)-10H-phenoxazine-3-carboxylic acid diethylamide, 10t Using an adaptation of Procedure 9, and substituting endo-10-(8-aza-bicyclo-[3.2.1]oct-3-yl)-10H-phenoxazine-3-carboxylic acid diethylamide, 2t for endo-10-(8-aza-bicyclo[3.2.1]oct-3-yl)-3-(1H-tetrazol-5-yl)-10H-phenoxazine, 5b, benzaldehyde for 2-pyridyl carboxaldehyde, tetrabutylammonium triacetoxyborohydride for sodium triacetoxyborohydride, and tetrahydrofuran for dichloroethane, the title compound endo-10-(8-benzyl-8-aza-bicyclo[3.2.1]oct-3-yl)-10H-phenoxazine-3-carboxylic acid diethylamide, 10t was obtained as a TFA salt after purification via reverse phase HPLC (eluent: CH$_3$CN in water containing 0.1% TFA). MS m/z (MH$^+$) 482.1.

Example U

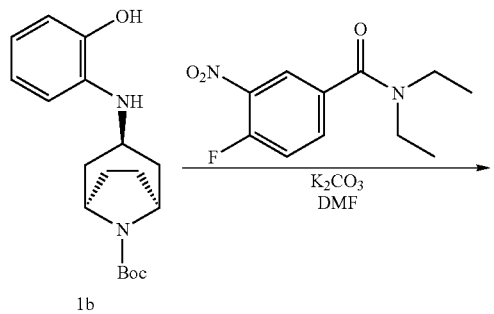

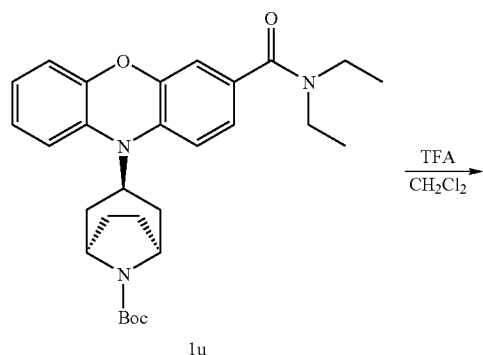

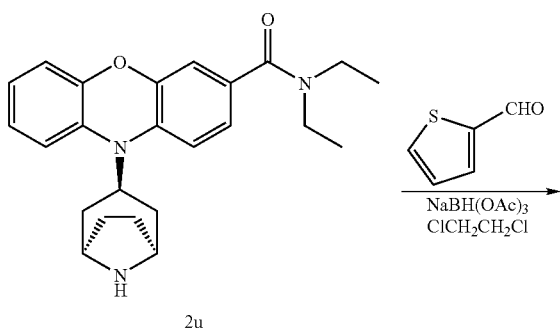

Exo-3-(3-Diethylcarbamoyl-phenoxazin-10-yl)-8-aza-bicyclo[3.2.1]octane-8-carboxylic acid tert-butyl ester, 1u Using an adaptation of Procedure 6, and substituting exo-3-(2-hydroxy-phenylamino)-8-aza-bicyclo[3.2.1]octane-8-carboxylic acid tert-butyl ester, 2b for 3-(2-hydroxy-phenylamino)-8-aza-bicyclo[3.2.1]octane-8-carboxylic acid tert-butyl ester, 1b, the title compound exo-3-(3-diethylcarbamoyl-phenoxazin-10-yl)-8-aza-bicyclo[3.2.1]octane-8-carboxylic acid tert-butyl ester, 1u was obtained. The crude material was used as such in the next reaction.

Exo-10-(8-Aza-bicyclo[3.2.1]oct-3-yl)-10H-phenoxazine-3-carboxylic acid diethylamide, 2u Using an adaptation of Procedure 25, substituting exo-3-(3-diethylcarbamoyl-phenoxazin-10-yl)-8-aza-bicyclo[3.2.1]octane-8-carboxylic acid tert-butyl ester, 1u for endo-3-(3-pyridin-3-yl-phenoxazin-10-yl)-8-aza-bicyclo[3.2.1]octane-8-carboxylic acid tert-butyl ester, 4j, and using a 25% solution of TFA in methylene chloride instead of neat TFA, the title compound exo-10-(8-aza-bicyclo[3.2.1]oct-3-yl)-10H-phenoxazine-3-carboxylic acid diethylamide, 2u was obtained as a TFA salt after purification via reverse phase HPLC (eluent: $CH_3CN$ in water containing 0.1% TFA). MS m/z ($MH^+$) 392.1.

Exo-10-(8-Phenethyl-8-aza-bicyclo[3.2.1]oct-3-yl)-10H-phenoxazine-3-carboxylic acid diethylamide, 3u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, phenyl acetaldehyde for 2-pyridyl carboxaldehyde, tetrabutylammonium triacetoxy-borohydride for sodium triacetoxy-borohydride, and tetrahydrofuran for dichloro-ethane, the title compound exo-10-(8-phenethyl-8-aza-bicyclo[3.2.1]oct-3-yl)-10H-phenoxazine-3-carboxylic acid diethylamide, 3u was obtained as a TFA salt after purification via reverse phase HPLC (eluent: $CH_3CN$ in water containing 0.1% TFA). MS m/z ($MH^+$)

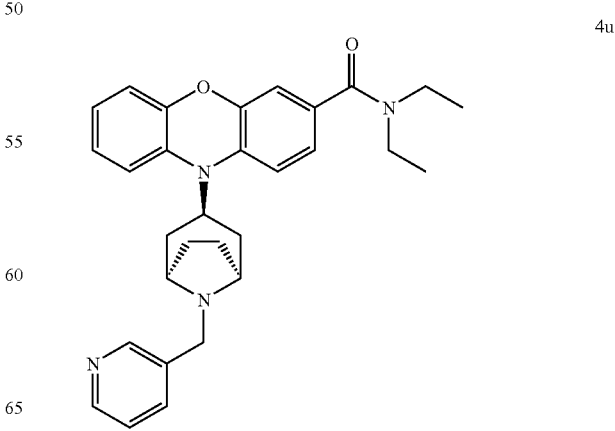

Exo-10-(8-Pyridin-3-ylmethyl-8-aza-bicyclo[3.2.1]oct-3-yl)-10H-phenoxazine-3-carboxylic acid diethylamide, 4u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, 3-pyridyl carboxaldehyde for 2-pyridyl carboxaldehyde, tetrabutylammonium triacetoxy-borohydride for sodium triacetoxyborohydride, and tetrahydrofuran for dichloro-ethane, the title compound exo-10-(8-pyridin-3-ylmethyl-8-aza-bicyclo[3.2.1]oct-3-yl)-10H-phenoxazine-3-carboxylic acid diethylamide, 4u was obtained as a TFA salt after purification via reverse phase HPLC (eluent: $CH_3CN$ in water containing 0.1% TFA). MS m/z ($MH^+$) 483.1.

Exo-10-[8-(3-Methyl-but-2-enyl)-8-aza-bicyclo[3.2.1]oct-3-yl]-10H-phenoxazine-3-carboxylic acid diethylamide, 6u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, 3-methyl-but-2-enyl carboxaldehyde for 2-pyridyl carboxaldehyde, tetrabutylammonium triacetoxyborohydride for sodium triacetoxyborohydride, and tetrahydrofuran for dichloroethane, the title compound exo-10-[8-(3-methyl-but-2-enyl)-8-aza-bicyclo[3.2.1]oct-3-yl]-10H-phenoxazine-3-carboxylic acid diethylamide, 6u was obtained as a TFA salt after purification via reverse phase HPLC (eluent: $CH_3CN$ in water containing 0.1% TFA). MS m/z ($MH^+$) 460.1.

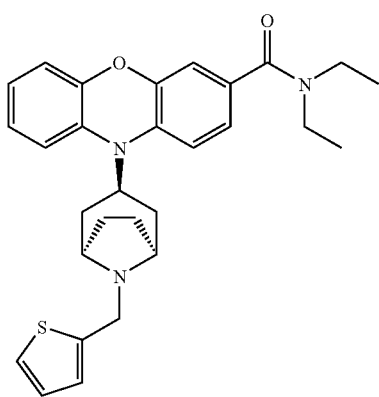

5u

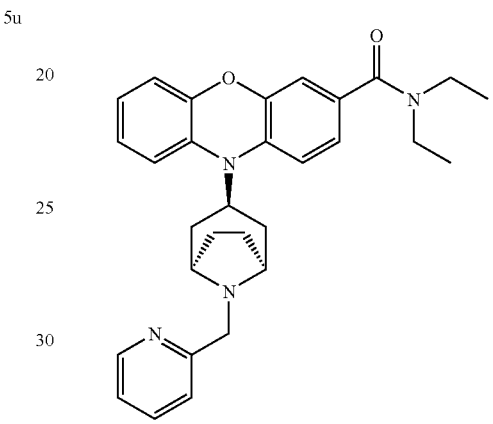

7u

Exo-10-(8-Thiophen-2-ylmethyl-8-aza-bicyclo[3.2.1]oct-3-yl)-10H-phenoxazine-3-carboxylic acid diethylamide, 5u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, thiophene-2-carboxaldehyde for 2-pyridyl carboxaldehyde, tetrabutylammonium triacetoxyborohydride for sodium triacetoxyborohydride, and tetrahydrofuran for dichloroethane, the title compound exo-10-(8-thiophen-2-ylmethyl-8-aza-bicyclo[3.2.1]oct-3-yl)-10H-phenoxazine-3-carboxylic acid diethylamide, 5u was obtained as a TFA salt after purification via reverse phase HPLC (eluent: $CH_3CN$ in water containing 0.1% TFA). MS m/z ($MH^+$) 488.1.

Exo-10-(8-Pyridin-2-ylmethyl-8-aza-bicyclo[3.2.1]oct-3-yl)-10H-phenoxazine-3-carboxylic acid diethylamide, 7u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, tetrabutylammonium triacetoxyborohydride for sodium triacetoxyborohydride, and tetrahydrofuran for dichloroethane, the title compound exo-10-(8-pyridin-2-ylmethyl-8-aza-bicyclo[3.2.1]oct-3-yl)-10H-phenoxazine-3-carboxylic acid diethylamide, 7u was obtained as a TFA salt after purification via reverse phase HPLC (eluent: $CH_3CN$ in water containing 0.1% TFA). MS m/z ($MH^+$) 483.1.

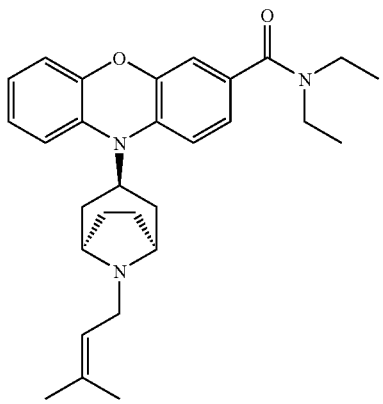

6u

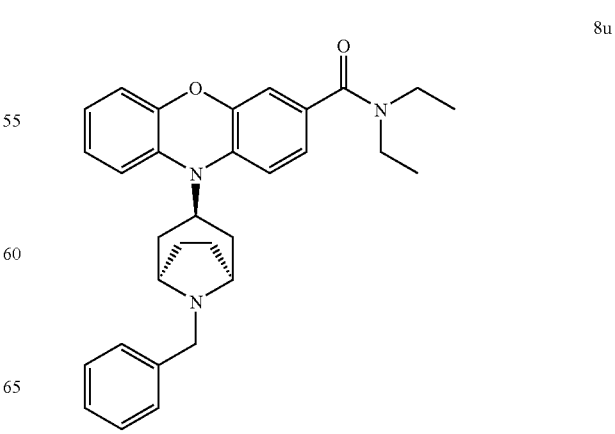

8u

Exo-10-(8-Benzyl-8-aza-bicyclo[3.2.1]oct-3-yl)-10H-phenoxazine-3-carboxylic acid diethylamide, 8u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, benzaldehyde for 2-pyridyl carboxaldehyde, tetrabutylammonium triacetoxyborohydride for sodium triacetoxyborohydride, and tetrahydrofuran for dichloroethane, the title compound exo-10-(8-benzyl-8-aza-bicyclo[3.2.1]oct-3-yl)-10H-phenoxazine-3-carboxylic acid diethylamide, 8u was obtained as a TFA salt after purification via reverse phase HPLC (eluent: CH$_3$CN in water containing 0.1% TFA). MS m/z (MH$^+$) 482.1.

9u

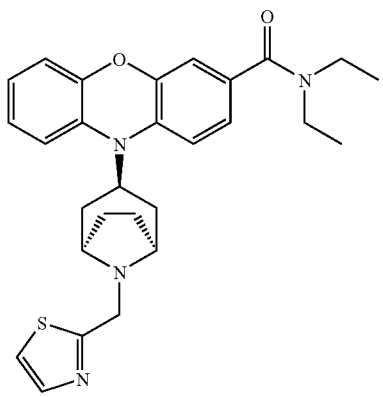

Exo-10-(8-Thiazol-2-ylmethyl-8-aza-bicyclo[3.2.1]oct-3-yl)-10H-phenoxazine-3-carboxylic acid diethylamide, 9u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, thiazol-2-ylmethyl carboxaldehyde for 2-pyridyl carboxaldehyde, tetrabutylammonium triacetoxyborohydride for sodium triacetoxyborohydride, and tetrahydrofuran for dichloroethane, the title compound exo-10-(8-thiazol-2-ylmethyl-8-aza-bicyclo[3.2.1]oct-3-yl)-10H-phenoxazine-3-carboxylic acid diethylamide, 9u was obtained as a TFA salt after purification via reverse phase HPLC (eluent: CH$_3$CN in water containing 0.1% TFA). MS m/z (MH$^+$) 489.1.

10u

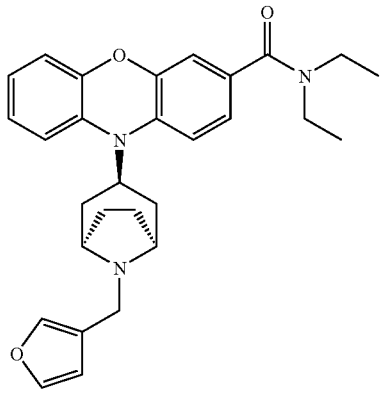

Exo-10-(8-Furan-3-ylmethyl-8-aza-bicyclo[3.2.1]oct-3-yl)-10H-phenoxazine-3-carboxylic acid diethylamide, 10u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, thiazol-2-ylmethyl carboxaldehyde for 2-pyridyl carboxaldehyde, tetrabutylammonium triacetoxyborohydride for sodium triacetoxyborohydride, and tetrahydrofuran for dichloroethane, the title compound exo-10-(8-furan-3-ylmethyl-8-aza-bicyclo[3.2.1]-oct-3-yl)-10H-phenoxazine-3-carboxylic acid diethylamide, 10u was obtained as a TFA salt after purification via reverse phase HPLC (eluent: CH$_3$CN in water containing 0.1% TFA). MS m/z (MH$^+$) 472.1.

11u

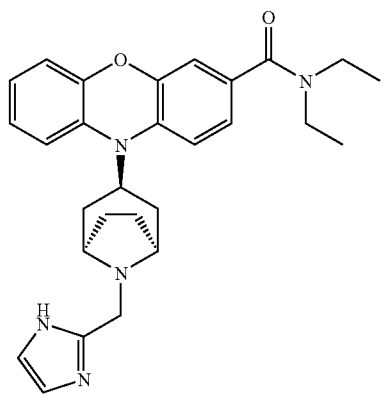

Exo-10-[8-(1H-Imidazol-2-ylmethyl)-8-aza-bicyclo[3.2.1]oct-3-yl]-10H-phenoxazine-3-carboxylic acid diethylamide, 11u Using an adaptation of Procedure 9, and substituting exo-10-(8-aza-bicyclo-[3.2.1]oct-3-yl)-10H-phenoxazine-3-carboxylic acid diethylamide, 2u for endo-10-(8-aza-bicyclo[3.2.1]oct-3-yl)-3-(1H-tetrazol-5-yl)-10H-phenoxazine, 5b, 1H-imidazol-2-ylmethyl carboxaldehyde for 2-pyridyl carboxaldehyde, tetrabutylammonium triacetoxyborohydride for sodium triacetoxyborohydride, and tetrahydrofuran for dichloroethane, the title compound exo-10-[8-(1H-imidazol-2-ylmethyl)-8-aza-bicyclo[3.2.1]oct-3-yl]-10H-phenoxazine-3-carboxylic acid diethylamide, 11u was obtained as a TFA salt after purification via reverse phase HPLC (eluent: CH$_3$CN in water containing 0.1% TFA). MS m/z (MH$^+$) 472.1.

Example V

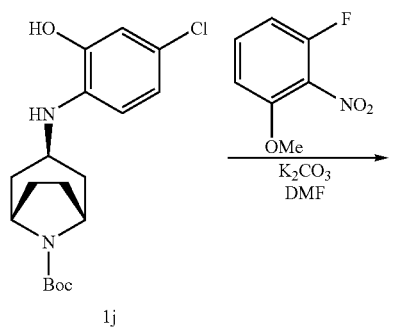

1j

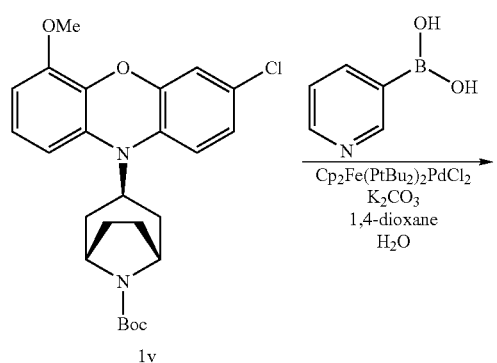

1v

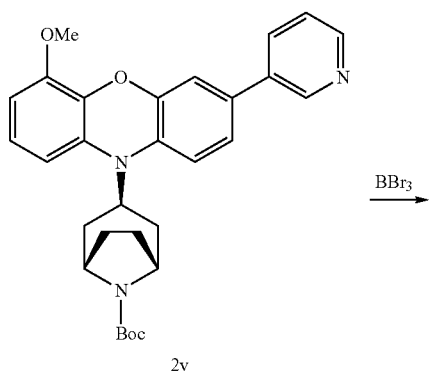

2v

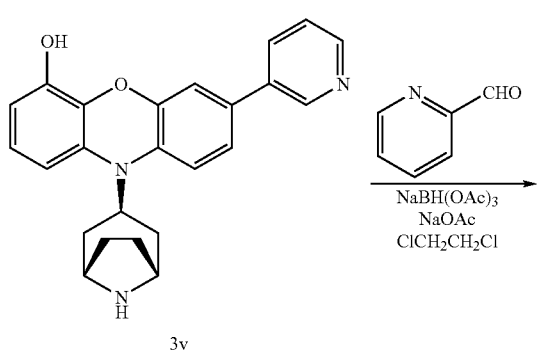

3v

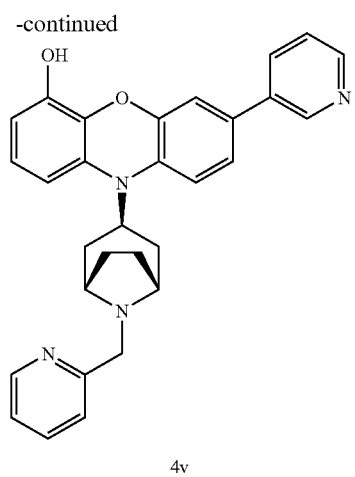

4v

Endo-3-(3-Chloro-6-methoxy-phenoxazin-10-yl)-8-aza-bicyclo[3.2.1]octane-8-carboxylic acid tert-butyl ester, 1v Using an adaptation of Procedure 2, and substituting 6-fluoro-2-methoxy-nitrobenzene, 1e for 4-fluoro-3-nitrobenzonitrile and endo-3-(4-chloro-2-hydroxy-phenylamino)-8-aza-bicyclo[3.2.1]octane-8-carboxylic acid tert-butyl ester, 1j for the TFA salt of 3-hydroxy-4-(8-methyl-8-aza-bicyclo[3.2.1]oct-3-ylamino)-benzoic acid methyl ester, 1a, the title compound endo-3-(3-chloro-6-methoxy-phenoxazin-10-yl)-8-aza-bicyclo[3.2.1]octane-8-carboxylic acid tert-butyl ester, 1v was obtained. MS m/z (MH$^+$) 457.2.

Endo-3-(6-Methoxy-3-pyridin-3-yl-phenoxazin-10-yl)-8-aza-bicyclo[3.2.1]octane-8-carboxylic acid tert-butyl ester, 2v Using an adaptation of the method described in Procedure 24, substituting endo-3-(3-chloro-6-methoxy-phenoxazin-10-yl)-8-aza-bicyclo[3.2.1]octane-8-carboxylic acid tert-butyl ester, 1v for endo-3-(3-chlorophenoxazin-10-yl)-8-aza-bicyclo[3.2.1]-octane-8-carboxylic acid tert-butyl ester, 3j, the title compound endo-3-(6-methoxy-3-pyridin-3-yl-phenoxazin-10-yl)-8-aza-bicyclo[3.2.1]octane-8-carboxylic acid tert-butyl ester, 2v was obtained. MS m/z (MH$^+$) 500.3.

Endo-10-(8-Aza-bicyclo[3.2.1]oct-3-yl)-7-pyridin-3-yl-10H-phenoxazin-4-ol, 3v

Using an adaptation of the method described in Procedure 16, substituting endo-3-(6-methoxy-3-pyridin-3-yl-phenoxazin-10-yl)-8-aza-bicyclo[3.2.1]octane-8-carboxylic acid tert-butyl ester, 2v for the TFA salt of 6-methoxy-10-(8-phenethyl-8-aza-bicyclo[3.2.1]oct-3-yl)-10H-phenoxazine-3-carboxylic acid diethylamide, 6e, the title compound endo-10-(8-aza-bicyclo[3.2.1]oct-3-yl)-7-pyridin-3-yl-10H-phenoxazin-4-ol, 3v was obtained as a TFA salt after purification via reverse phase chromatography (eluent: CH$_3$CN in water containing 0.1% TFA). MS m/z (MH$^+$) 386.1.

Endo-7-Pyridin-3-yl-10-(8-pyridin-2-ylmethyl-8-aza-bicyclo[3.2.1]oct-3-yl)-10H-phenoxazin-4-ol, 4v Using an adaptation of the method described in Procedure 1, substituting the TFA salt of endo-10-(8-aza-bicyclo[3.2.1]oct-3-yl)-7-pyridin-3-yl-10H-phenoxazin-4-ol, 3v for 4-amino-3-hydroxybenzoic acid methyl ester, and 2-pyridyl carboxaldehyde for 8-methyl-8-aza-bicyclo[3.2.1]octan-3-one, the title compound endo-7-pyridin-3-yl-10-(8-pyridin-2-ylmethyl-8-aza-bicyclo[3.2.1]oct-3-yl)-10H-phenoxazin-4-ol, 4v was obtained as a TFA salt after purification via reverse phase chromatography (eluent: $CH_3CN$ in water containing 0.1% TFA). MS m/z ($MH^+$) 477.2.

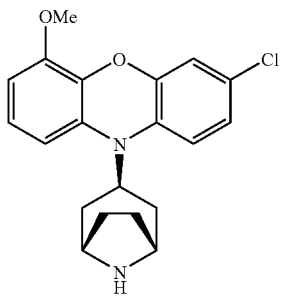

Endo-10-(8-Aza-bicyclo[3.2.1]oct-3-yl)-3-chloro-6-methoxy-10H-phenoxazine, 5v Using an adaptation of the method described in Procedure 25, substituting the TFA salt of endo-7-pyridin-3-yl-10-(8-pyridin-2-ylmethyl-8-aza-bicyclo[3.2.1]oct-3-yl)-10H-phenoxazin-4-ol, 4v for endo-3-(3-pyridin-3-yl-phenoxazin-10-yl)-8-aza-bicyclo[3.2.1]octane-8-carboxylic acid tert-butyl ester, 4j, the title compound endo-10-(8-aza-bicyclo[3.2.1]oct-3-yl)-3-chloro-6-methoxy-10H-phenoxazine, 5v was obtained as a TFA salt after purification via reverse phase chromatography (eluent: $CH_3CN$ in water containing 0.1% TFA). MS m/z ($MH^+$) 357.1.

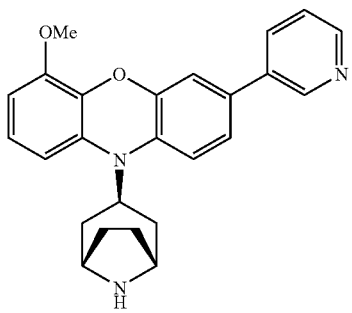

Endo-10-(8-Aza-bicyclo[3.2.1]oct-3-yl)-6-methoxy-3-pyridin-3-yl-10H-phenoxazine, 6v Using an adaptation of the method described in Procedure 25, substituting endo-3-(6-methoxy-3-pyridin-3-yl-phenoxazin-10-yl)-8-aza-bicyclo[3.2.1]octane-8-carboxylic acid tert-butyl ester, 2v for endo-3-(3-pyridin-3-yl-phenoxazin-10-yl)-8-aza-bicyclo[3.2.1]octane-8-carboxylic acid tert-butyl ester, 4j, the title compound endo-10-(8-aza-bicyclo[3.2.1]oct-3-yl)-6-methoxy-3-pyridin-3-yl-10H-phenoxazine, 6v was obtained as a TFA salt after purification via reverse phase chromatography (eluent: $CH_3CN$ in water containing 0.1% TFA). MS m/z ($MH^+$) 400.2.

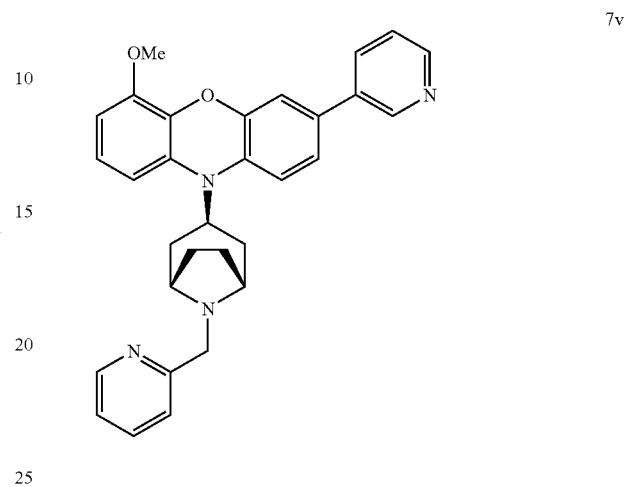

Endo-6-Methoxy-3-pyridin-3-yl-10-(8-pyridin-2-ylmethyl-8-aza-bicyclo[3.2.1]oct-3-yl)-10H-phenoxazine, 7v Using an adaptation of the method described in Procedure 1, substituting endo-3-(6-methoxy-3-pyridin-3-yl-phenoxazin-10-yl)-8-aza-bicyclo[3.2.1]octane-8-carboxylic acid tert-butyl ester, 2v for 4-amino-3-hydroxybenzoic acid methyl ester, and 2-pyridyl carboxaldehyde for 8-methyl-8-aza-bicyclo[3.2.1]octan-3-one, the title compound endo-6-methoxy-3-pyridin-3-yl-10-(8-pyridin-2-ylmethyl-8-aza-bicyclo[3.2.1]oct-3-yl)-10H-phenoxazine, 7v was obtained as a TFA salt after purification via reverse phase chromatography (eluent: $CH_3CN$ in water containing 0.1% TFA). MS m/z ($MH^+$) 491.2.

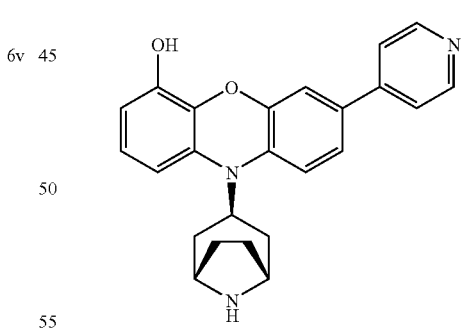

Endo-10-(8-Aza-bicyclo[3.2.1]oct-3-yl)-7-pyridin-4-yl-10H-phenoxazin-4-ol, 8v Using an adaptation of the methods described in Procedures 24 and 16, substituting endo-3-(3-chloro-6-methoxy-phenoxazin-10-yl)-8-aza-bicyclo[3.2.1]octane-8-carboxylic acid tert-butyl ester, 1v for endo-3-(3-chlorophenoxazin-10-yl)-8-aza-bicyclo[3.2.1]-octane-8-carboxylic acid tert-butyl ester, 3j, and 4-pyridylboronic acid for 3-pyridylboronic acid in Procedure 24, the title compound endo-10-(8-aza-bicyclo

[3.2.1]oct-3-yl)-7-pyridin-4-yl-10H-phenoxazin-4-ol, 8v was obtained as a TFA salt after purification via reverse phase chromatography (eluent: CH₃CN in water containing 0.1% TFA). MS m/z (MH⁺) 386.2.

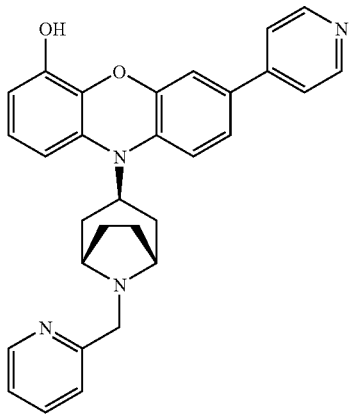

Endo-7-Pyridin-4-yl-10-(8-pyridin-2-ylmethyl-8-aza-bicyclo[3.2.1]oct-3-yl)-10H-phenoxazin-4-ol, 9v Using an adaptation of the method described in Procedure 1, substituting the TFA salt of endo-10-(8-aza-bicyclo[3.2.1]oct-3-yl)-7-pyridin-4-yl-10H-phenoxazin-4-ol, 8v for 4-amino-3-hydroxybenzoic acid methyl ester, and 2-pyridyl carboxaldehyde for 8-methyl-8-aza-bicyclo[3.2.1]octan-3-one, the title compound endo-7-pyridin-4-yl-10-(8-pyridin-2-ylmethyl-8-aza-bicyclo[3.2.1]oct-3-yl)-10H-phenoxazin-4-ol, 9v was obtained as a TFA salt after purification via reverse phase chromatography (eluent: CH₃CN in water containing 0.1% TFA). MS m/z (MH⁺) 477.3.

Endo-10-(8-Phenethyl-8-aza-bicyclo[3.2.1]oct-3-yl)-7-pyridin-4-yl-10H-phenoxazin-4-ol, 10v Using an adaptation of the method described in Procedure 1, substituting the TFA salt of endo-10-(8-aza-bicyclo[3.2.1]oct-3-yl)-7-pyridin-4-yl-10H-phenoxazin-4-ol, 8v for 4-amino-3-hydroxybenzoic acid methyl ester, and phenyl acetaldehyde for 8-methyl-8-aza-bicyclo[3.2.1]octan-3-one, the title compound endo-O-(8-phenethyl-8-aza-bicyclo[3.2.1]oct-3-yl)-7-pyridin-4-yl-10H-phenoxazin-4-ol, 10v was obtained as a TFA salt after purification via reverse phase chromatography (eluent: CH₃CN in water containing 0.1% TFA). MS m/z (MH⁺) 490.3.

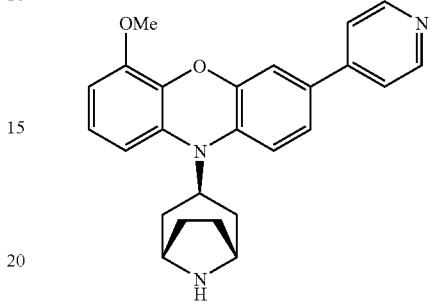

Endo-10-(8-Aza-bicyclo[3.2.1]oct-3-yl)-6-methoxy-3-pyridin-4-yl-10H-phenoxazine, 1v Using an adaptation of the methods described in Procedures 24 and 25, substituting endo-3-(3-chloro-6-methoxy-phenoxazin-10-yl)-8-aza-bicyclo[3.2.1]octane-8-carboxylic acid tert-butyl ester, 1v for endo-3-(3-chlorophenoxazin-10-yl)-8-aza-bicyclo[3.2.1]-octane-8-carboxylic acid tert-butyl ester, 3j, and 4-pyridylboronic acid for 3-pyridylboronic acid in Procedure 24, the title compound endo-10-(8-aza-bicyclo[3.2.1]oct-3-yl)-6-methoxy-3-pyridin-4-yl-10H-phenoxazine, 11v was obtained as a TFA salt after purification via reverse phase chromatography (eluent: CH₃CN in water containing 0.1% TFA). MS m/z (MH⁺) 400.2.

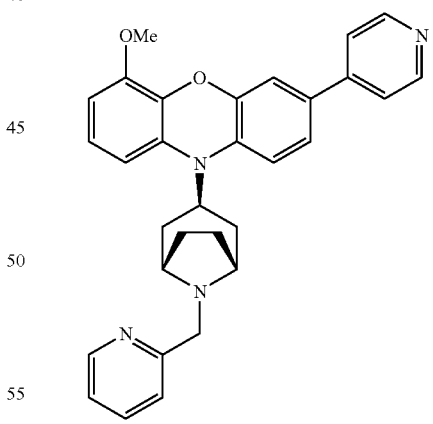

Endo-6-Methoxy-3-pyridin-4-yl-10-(8-pyridin-2-ylmethyl-8-aza-bicyclo[3.2.1]oct-3-yl)-10H-phenoxazine, 12v Using an adaptation of the method described in Procedure 1, substituting the TFA salt of endo-10-(8-aza-bicyclo[3.2.1]oct-3-yl)-6-methoxy-3-pyridin-4-yl-10H-phenoxazine, 11v for 4-amino-3-hydroxybenzoic acid methyl ester, and 2-pyridyl carboxaldehyde for 8-methyl-8-aza-bicyclo[3.2.1]octan-3-one, the title compound endo-6-methoxy-3-pyridin-4-yl-10-(8-pyridin-2-ylmethyl-8-aza-bicyclo[3.2.1]oct-3-yl)-10H-phenoxazine, 12v was obtained as a TFA salt after purification via reverse phase chromatography (eluent: CH$_3$CN in water containing 0.1% TFA). MS m/z (MH$^+$) 491.2.

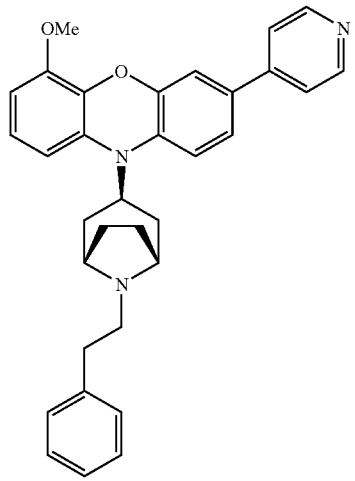

Endo-6-Methoxy-10-(8-phenethyl-8-aza-bicyclo [3.2.1]oct-3-yl)-3-pyridin-4-yl-10H-phenoxazine, 13v Using an adaptation of the method described in Procedure 1, substituting the TFA salt of endo-10-(8-aza-bicyclo[3.2.1]oct-3-yl)-6-methoxy-3-pyridin-4-yl-10H-phenoxazine, 11v for 4-amino-3-hydroxybenzoic acid methyl ester, and phenyl acetaldehyde for 8-methyl-8-aza-bicyclo[3.2.1]octan-3-one, the title compound endo-6-methoxy-10-(8-phenethyl-8-aza-bicyclo[3.2.1]oct-3-yl)-3-pyridin-4-yl-10H-phenoxazine, 13v was obtained as a TFA salt after purification via reverse phase chromatography (eluent: CH$_3$CN in water containing 0.1% TFA). MS m/z (MH$^+$) 504.3.

Example X

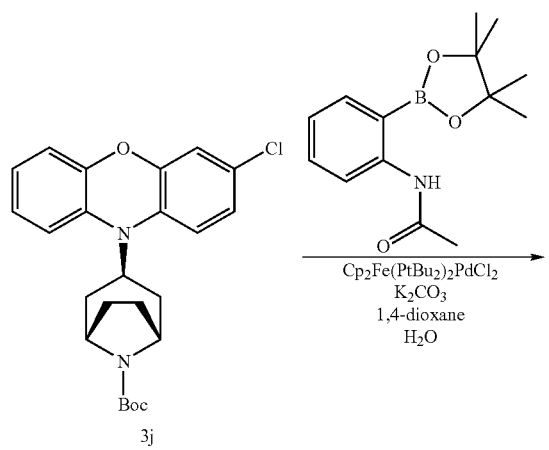

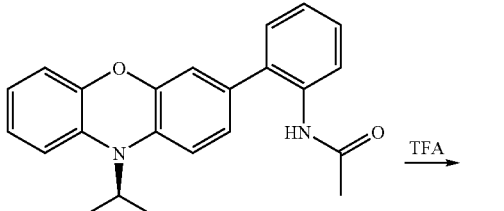

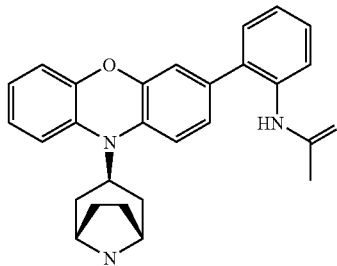 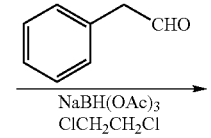

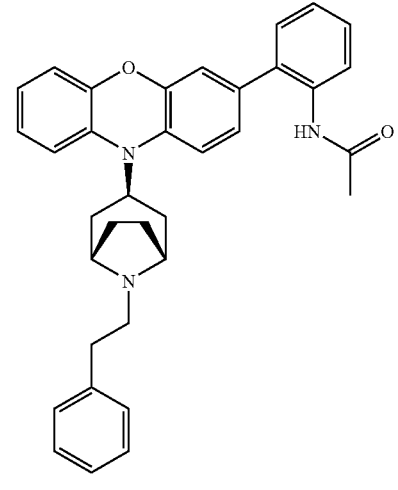

Endo-3-[3-(2-Acetylaminophenyl)-phenoxazin-10-yl]-8-aza-bicyclo[3.2.1]octane-8-carboxylic acid tert-butyl ester, 1x Using an adaptation of the method described in Procedure 24, substituting N-[2-(4,4,5,5-tetramethyl-[1,3,2]dioxaborolan-2-yl)-phenyl]-acetamide for 3-pyridyl boronic acid, the title compound endo-3-[3-(2-acetylaminophenyl)-phenoxazin-10-yl]-8-aza-bicyclo[3.2.1]octane-8-carboxylic acid tert-butyl ester, 1x was obtained as a TFA salt after purification via reverse phase chromatography (eluent: CH$_3$CN in water containing 0.1% TFA).

Endo-N-{2-[10-(8-Aza-bicyclo[3.2.1]oct-3-yl)-10H-phenoxazin-3-yl]-phenyl}-acetamide, 2x Using an adaptation of Procedure 25, substituting the TFA salt of endo-3-[3-(2-acetylaminophenyl)-phenoxazin-10-yl]-8-aza-bicyclo[3.2.1]octane-8-carboxylic acid tert-butyl ester, 1x for endo-3-(3-pyridin-3-yl-phenoxazin-10-yl)-8-aza-bicyclo[3.2.1]octane-8-carboxylic acid tert-butyl ester, 4j, the title compound endo-N-{2-[10-(8-aza-bicyclo[3.2.1]oct-3-yl)-10H-phenoxazin-3-yl]-phenyl}-acetamide, 2x was obtained as a TFA salt after purification via reverse phase HPLC (eluent: CH$_3$CN in water containing 0.1% TFA). MS m/z (MH$^+$) 426.2.

Endo-N-{2-[10-(8-Phenethyl-8-aza-bicyclo[3.2.1]oct-3-yl)-10H-phenoxazin-3-yl]-phenyl}-acetamide, 3x Using an adaptation of the method described in Procedure 1, substituting the TFA salt of endo-N-{2-[10-(8-aza-bicyclo[3.2.1]oct-3-yl)-10H-phenoxazin-3-yl]-phenyl}-acetamide, 2x for 4-amino-3-hydroxybenzoic acid methyl ester, and phenyl acetaldehyde for 8-methyl-8-aza-bicyclo[3.2.1]octan-3-one, the title compound endo-N-{2-[10-(8-phenethyl-8-aza-bicyclo[3.2.1]oct-3-yl)-10H-phenoxazin-3-yl]-phenyl}-acetamide, 3x was obtained as a TFA salt after purification via reverse phase chromatography (eluent: CH$_3$CN in water containing 0.1% TFA). MS m/z (MH$^+$) 530.3.

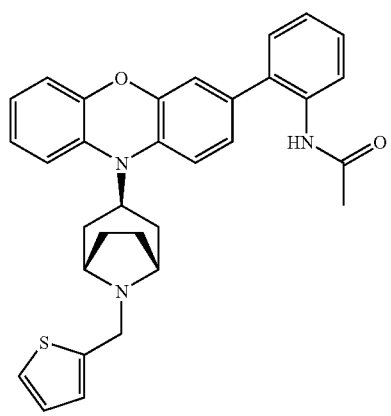

Endo-N-{2-[10-(8-Thiophen-2-ylmethyl-8-aza-bicyclo[3.2.1]oct-3-yl)-10H-phenoxazin-3-yl]-phenyl}-acetamide, 4x Using an adaptation of the method described in Procedure 1, substituting the TFA salt of endo-N-{2-[10-(8-aza-bicyclo[3.2.1]oct-3-yl)-10H-phenoxazin-3-yl]-phenyl}-acetamide, 2x for 4-amino-3-hydroxybenzoic acid methyl ester, and 2-thiophene carboxaldehyde for 8-methyl-8-aza-bicyclo[3.2.1]octan-3-one, the title compound endo-N-{2-[10-(8-thiophen-2-ylmethyl-8-aza-bicyclo[3.2.1]oct-3-yl)-10H-phenoxazin-3-yl]-phenyl}-acetamide, 4x was obtained as a TFA salt after purification via reverse phase chromatography (eluent: CH$_3$CN in water containing 0.1% TFA). MS m/z (MH$^+$) 522.2.

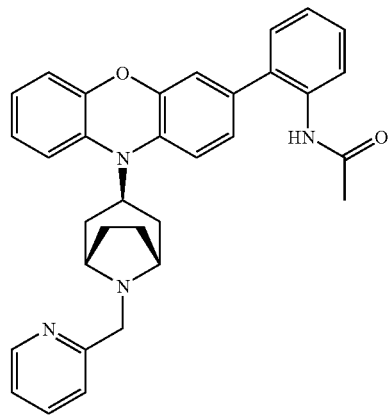

Endo-N-{2-[10-(8-Pyridin-2-ylmethyl-8-aza-bicyclo[3.2.1]oct-3-yl)-10H-phenoxazin-3-yl]-phenyl}-acetamide, 5x Using an adaptation of the method described in Procedure 1, substituting the TFA salt of endo-N-{2-[10-(8-aza-bicyclo[3.2.1]oct-3-yl)-10H-phenoxazin-3-yl]-phenyl}-acetamide, 2x for 4-amino-3-hydroxybenzoic acid methyl ester, and 2-pyridyl carboxaldehyde for 8-methyl-8-aza-bicyclo[3.2.1]octan-3-one, the title compound endo-N-{2-[10-(8-pyridin-2-ylmethyl-8-aza-bicyclo[3.2.1]oct-3-yl)-10H-phenoxazin-3-yl]-phenyl}-acetamide, 5x was obtained as a TFA salt after purification via reverse phase chromatography (eluent: CH$_3$CN in water containing 0.1% TFA). MS m/z (MH$^+$) 517.2.

Example Y

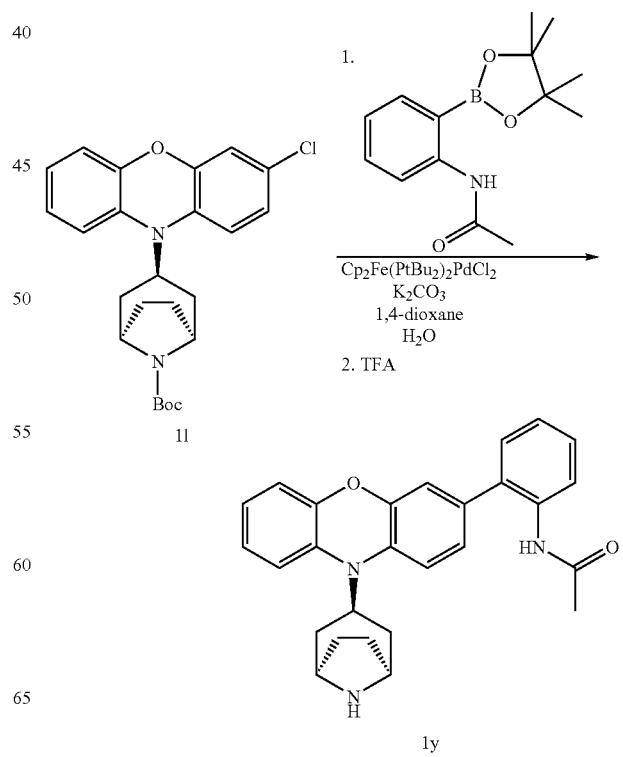

Exo-N-{2-[10-(8-Aza-bicyclo[3.2.1]oct-3-yl)-10H-phenoxazin-3-yl]-phenyl}-acetamide, 1y Using an adaptation of the methods described in Procedures 24 and 25, and substituting exo-3-(3-chlorophenoxazin-10-yl)-8-aza-bicyclo[3.2.1]octane-8-carboxylic acid tert-butyl ester, 1l for endo-3-(3-chlorophenoxazin-10-yl)-8-aza-bicyclo[3.2.1]octane-8-carboxylic acid tert-butyl ester, 3j, and N-[2-(4,4,5,5-tetramethyl-[1,3,2]dioxaborolan-2-yl)-phenyl]-acetamide for 3-pyridyl boronic acid in Procedure 24, the title compound exo-N-{2-[10-(8-aza-bicyclo[3.2.1]oct-3-yl)-10H-phenoxazin-3-yl]-phenyl}-acetamide, 1y was obtained as a TFA salt after purification via reverse phase chromatography (eluent: $CH_3CN$ in water containing 0.1% TFA). MS m/z (MH$^+$) 426.2.

Example Z

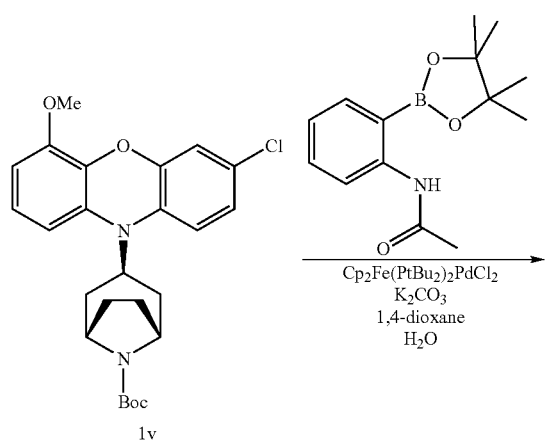

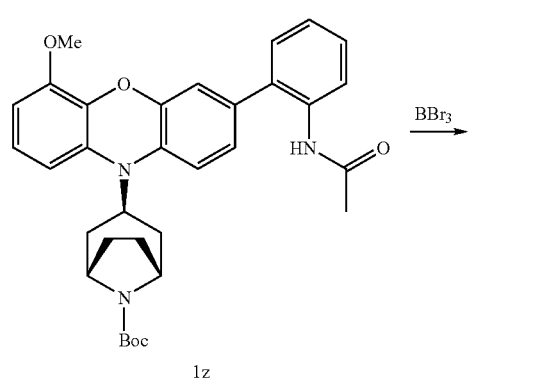

Endo-3-[3-(2-Acetylaminophenyl)-6-methoxy-phenoxazin-10-yl]-8-aza-bicyclo[3.2.1]octane-8-carboxylic acid tert-butyl ester, 1z Using an adaptation of the method described in Procedure 24, substituting N-[2-(4,4,5,5-tetramethyl-[1,3,2]dioxaborolan-2-yl)-phenyl]-acetamide for 3-pyridyl boronic acid, the title compound endo-3-[3-(2-acetylaminophenyl)-6-methoxy-phenoxazin-10-yl]-8-aza-bicyclo[3.2.1]octane-8-carboxylic acid tert-butyl ester, 1z was obtained as a TFA salt after purification via reverse phase chromatography (eluent: $CH_3CN$ in water containing 0.1% TFA).

Endo-N-{2-[10-(8-Aza-bicyclo[3.2.1]oct-3-yl)-6-hydroxy-10H-phenoxazin-3-yl]-phenyl}-acetamide, 2z Using an adaptation of the method described in Procedure 16, substituting the TFA salt of endo-3-[3-(2-acetylaminophenyl)-6-methoxy-phenoxazin-10-yl]-8-aza-bicyclo[3.2.1]octane-8-carboxylic acid tert-butyl ester, 1z for the TFA salt of 6-methoxy-10-(8-phenethyl-8-aza-bicyclo[3.2.1]oct-3-yl)-10H-phenoxazine-3-carboxylic acid diethylamide, 6e, the title compound endo-N-{2-[10-(8-aza-bicyclo[3.2.1]oct-3-yl)-6-hydroxy-10H-phenoxazin-3-yl]-phenyl}-acetamide, 2z was obtained as a TFA salt after purification via reverse phase chromatography (eluent: $CH_3CN$ in water containing 0.1% TFA). MS m/z (MH$^+$) 442.2.

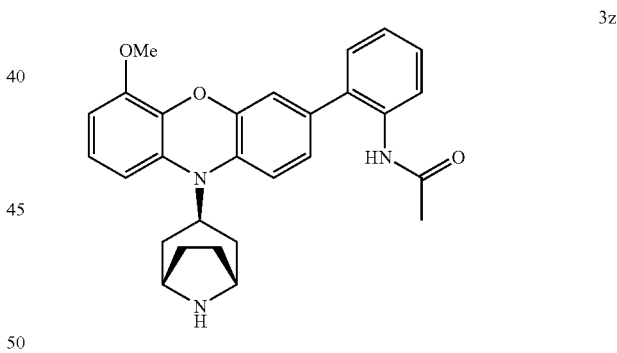

Endo-N-{2-[10-(8-Aza-bicyclo[3.2.1]oct-3-yl)-6-methoxy-10H-phenoxazin-3-yl]-phenyl}-acetamide, 3z Using an adaptation of the method described in Procedure 25, substituting the TFA salt of endo-3-[3-(2-acetylaminophenyl)-6-methoxy-phenoxazin-10-yl]-8-aza-bicyclo[3.2.1]octane-8-carboxylic acid tert-butyl ester, 1z for endo-3-(3-pyridin-3-yl-phenoxazin-10-yl)-8-aza-bicyclo[3.2.1]octane-8-carboxylic acid tert-butyl ester, 4j, the title compound endo-N-{2-[10-(8-aza-bicyclo[3.2.1]oct-3-yl)-6-methoxy-10H-phenoxazin-3-yl]-phenyl}-acetamide, 3z was

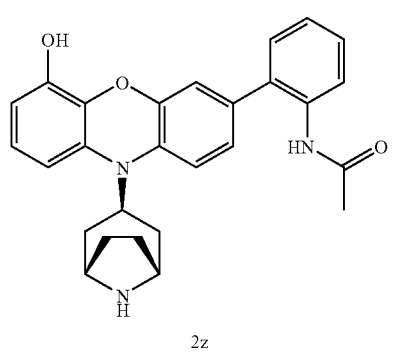

obtained as a TFA salt after purification via reverse phase chromatography (eluent: CH₃CN in water containing 0.1% TFA). MS m/z (MH⁺) 456.2.

Example AA

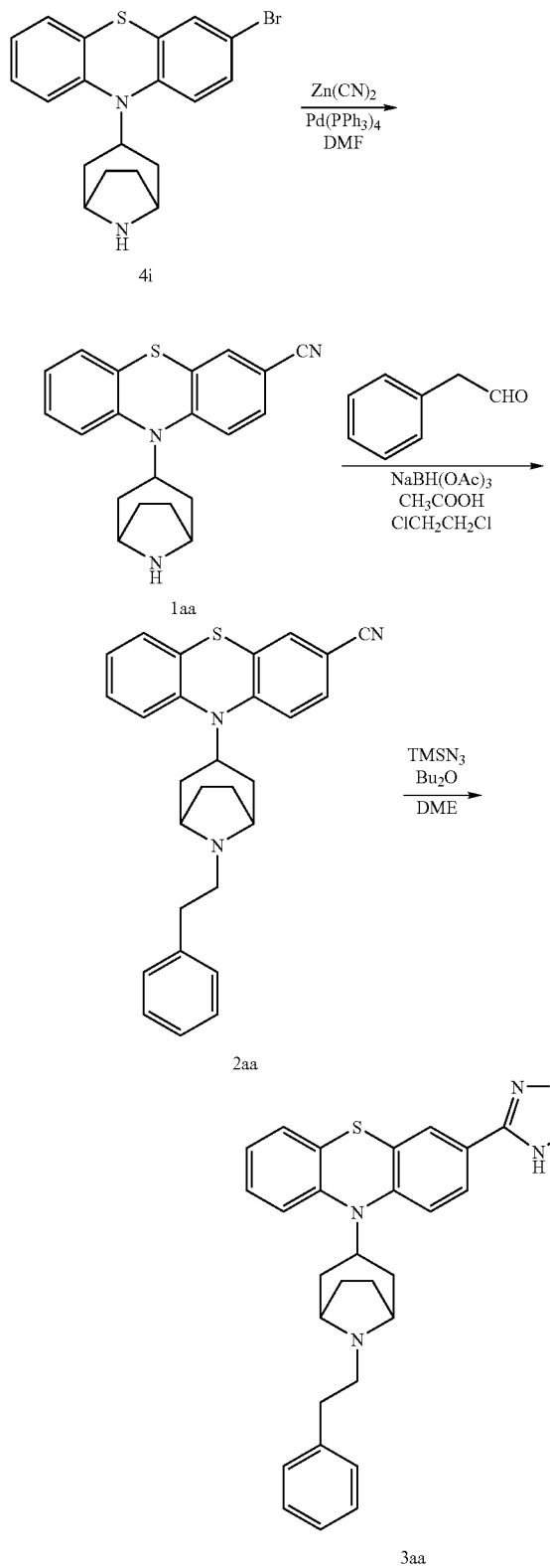

Procedure 28

10-(8-Aza-bicyclo[3.2.1]oct-3-yl)-10H-phenothiazine-3-carbonitrile, 1aa

To a solution of 10-(8-aza-bicyclo[3.2.1]oct-3-yl)-3-bromo-10H-phenothiazine, 4i (50 mg, 0.13 mmol) in DMF (750 µL) was added zinc cyanide (15 mg, 0.13 mmol) and tetrakistriphenylphosphine palladium (4 mg), the solution was purged with nitrogen, and the mixture was heated in the microwave for 5 min at 160° C. The mixture was allowed to cool to rt, and purified via reverse phase HPLC (eluent: CH₃CN in water containing 0.1% TFA) to yield title compound 10-(8-aza-bicyclo[3.2.1]oct-3-yl)-10H-phenothiazine-3-carbonitrile, 1aa as a TFA salt and as a mixture of endo and exo isomers. MS m/z (MH⁺) 334.1.

10-(8-Phenethyl-8-aza-bicyclo[3.2.1]oct-3-yl)-10H-phenothiazine-3-carbonitrile, 2aa Using an adaptation of the method described in Procedure 22, substituting the TFA salt of 10-(8-aza-bicyclo[3.2.1]oct-3-yl)-10H-phenothiazine-3-carbonitrile, 1 aa for 3-bromo-10-piperidin-4-yl-10H-phenothiazine, 4l, the title compound 10-(8-phenethyl-8-aza-bicyclo[3.2.1]oct-3-yl)-10H-phenothiazine-3-carbonitrile, 2aa was obtained as a TFA salt after purification via reverse phase chromatography (eluent: CH₃CN in water containing 0.1% TFA) and as a mixture of endo and exo isomers.

Procedure 29

10-(8-Phenethyl-8-aza-bicyclo[3.2.1]oct-3-yl)-3-(1H-tetrazol-5-yl)-10H-phenothiazine, 3aa To a solution of 10-(8-phenethyl-8-aza-bicyclo[3.2.1]oct-3-yl)-10H-phenothiazine-3-carbonitrile, 2aa (10 mg, 29 µmol) in dimethoxyethane was added trimethylsilyl azide (15 µL, 115 µmol) and dibutyltin oxide (1.5 mg), and the mixture was heated in a microwave for 15 min at 150° C. The mixture was allowed to cool to rt, and purified via reverse phase HPLC (eluent: CH₃CN in water containing 0.1% TFA) to yield title compound 10-(8-phenethyl-8-aza-bicyclo[3.2.1]oct-3-yl)-3-(1H-tetrazol-5-yl)-10H-phenothiazine, 3aa as a TFA salt and as a mixture of endo and exo isomers. MS m/z (MH⁺) 481.2.

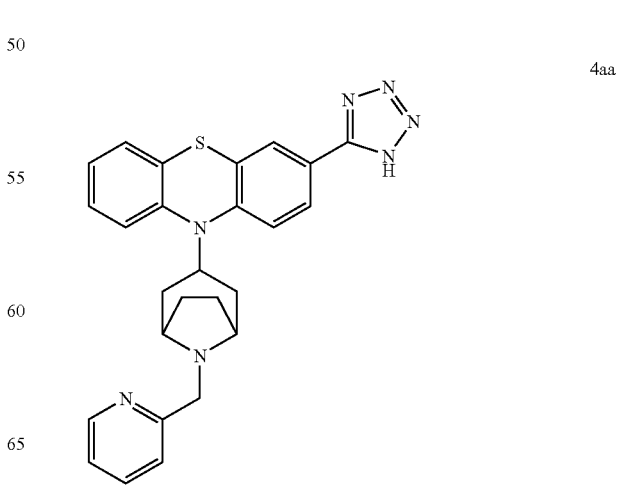

4aa

10-(8-Pyridin-2-ylmethyl-8-aza-bicyclo[3.2.1]oct-3-yl)-3-(1H-tetrazol-5-yl)-10H-phenothiazine, 4aa Using an adaptation of the methods described in Procedures 22 and 29, substituting the TFA salt of 10-(8-aza-bicyclo[3.2.1]oct-3-yl)-10H-phenothiazine-3-carbonitrile, 1 aa for 3-bromo-10-piperidin-4-yl-10H-phenothiazine, 4i and 2-pyridyl carboxaldehyde for 3-furyl carboxaldehyde in Procedure 22, the title compound 10-(8-pyridin-2-ylmethyl-8-aza-bicyclo[3.2.1]oct-3-yl)-3-(1H-tetrazol-5-yl)-10H-phenothiazine, 4aa was obtained as a TFA salt after purification via reverse phase chromatography (eluent: CH$_3$CN in water containing 0.1% TFA) and as a mixture of endo and exo isomers. MS m/z (MH$^+$) 468.2.

N,N-Diethyl-10-(8-phenethyl-8-aza-bicyclo[3.2.1]oct-3-yl)-10-H-phenothiazine-3-carboxamidine, 6aa Using an adaptation of the method described in Procedure 10, substituting the TFA salt of 10-(8-phenethyl-8-aza-bicyclo[3.2.1]oct-3-yl)-10H-phenothiazine-3-carbonitrile, 2aa for endo-3-(3-cyano-phenoxazin-10-yl)-8-aza-bicyclo[3.2.1]octane-8-carboxylic acid tert-butyl ester, 3b, the title compound N,N-diethyl-10-(8-phenethyl-8-aza-bicyclo[3.2.1]oct-3-yl)-10H-phenothiazine-3-carboxamidine, 6aa was obtained as a TFA salt after purification via reverse phase chromatography (eluent: CH$_3$CN in water containing 0.1% TFA) and as a mixture of endo and exo isomers. MS m/z (MH$^+$) 511.3.

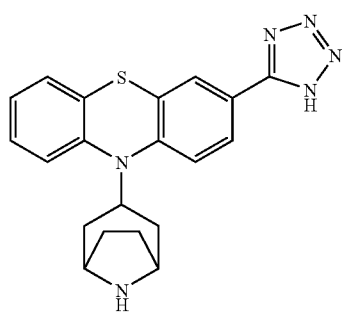

5aa

10-(8-Aza-bicyclo[3.2.1]oct-3-yl)-3-(1H-tetrazol-5-yl)-10H-phenothiazine, 5aa Using an adaptation of the method described in Procedure 29, substituting the TFA salt of 10-(8-aza-bicyclo[3.2.1]oct-3-yl)-10H-phenothiazine-3-carbonitrile, 1 aa for 10-(8-phenethyl-8-aza-bicyclo[3.2.1]oct-3-yl)-10H-phenothiazine-3-carbonitrile, 2aa, the title compound 10-(8-aza-bicyclo[3.2.1]oct-3-yl)-3-(1H-tetrazol-5-yl)-10H-phenothiazine, 5aa was obtained as a TFA salt after purification via reverse phase chromatography (eluent: CH$_3$CN in water containing 0.1% TFA) and as a mixture of endo and exo isomers.
MS m/z (MH$^+$) 377.2.

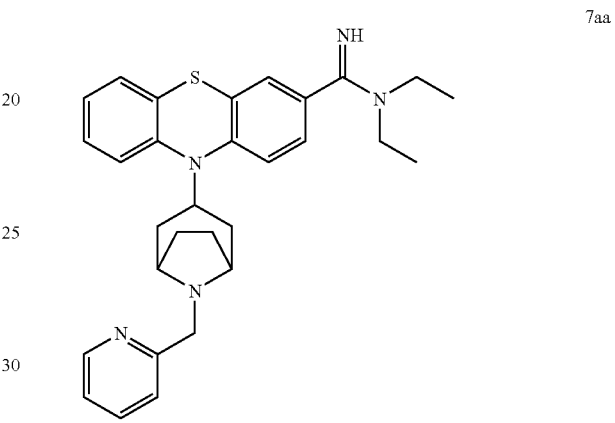

7aa

N,N-Diethyl-10-(8-pyridin-2-ylmethyl-8-aza-bicyclo[3.2.1]oct-3-yl)-10H-phenothiazine-3-carboxamidine, 7aa Using an adaptation of the methods described in Procedures 22 and 10, substituting the TFA salt of 10-(8-aza-bicyclo[3.2.1]oct-3-yl)-10H-phenothiazine-3-carbonitrile, 1 aa for endo-3-(3-cyano-phenoxazin-10-yl)-8-aza-bicyclo[3.2.1]octane-8-carboxylic acid tert-butyl ester, 3b, and 2-pyridyl carboxaldehyde for 3-furyl carboxaldehyde, the title compound N,N-diethyl-10-(8-pyridin-2-ylmethyl-8-aza-bicyclo[3.2.1]oct-3-yl)-10H-phenothiazine-3-carboxamidine, 7aa was obtained as a TFA salt after purification via reverse phase chromatography (eluent: CH$_3$CN in water containing 0.1% TFA) and as a mixture of endo and exo isomers.
MS m/z (MH$^+$) 498.3.

Example BB

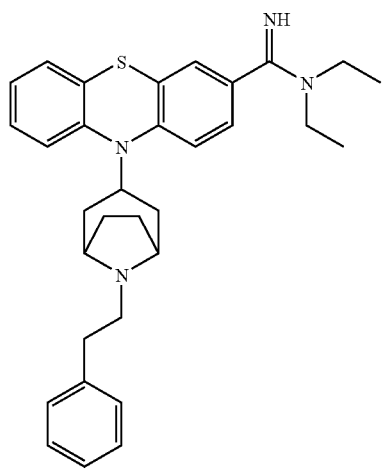

6aa

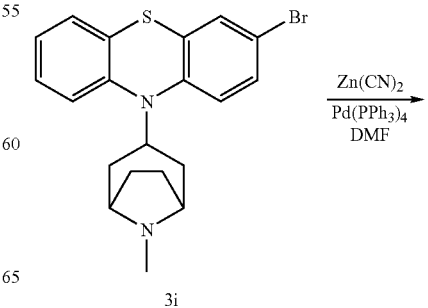

3i

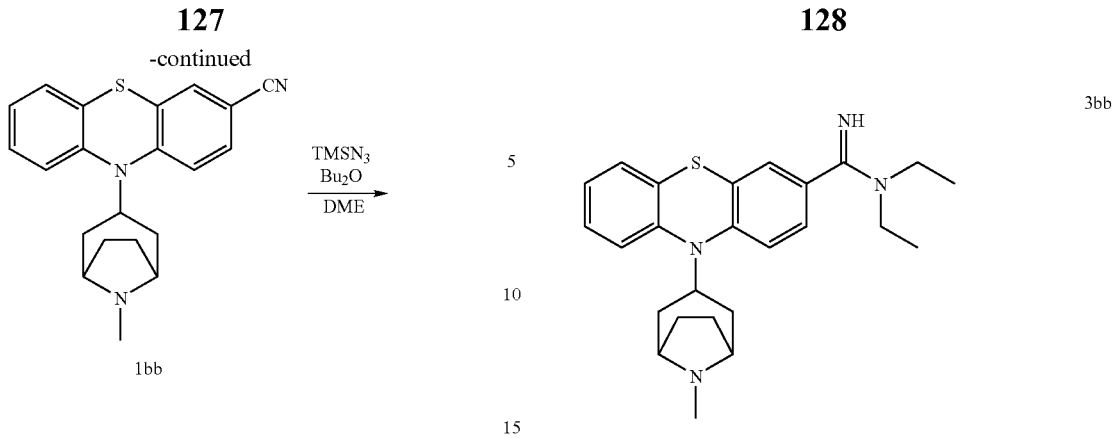

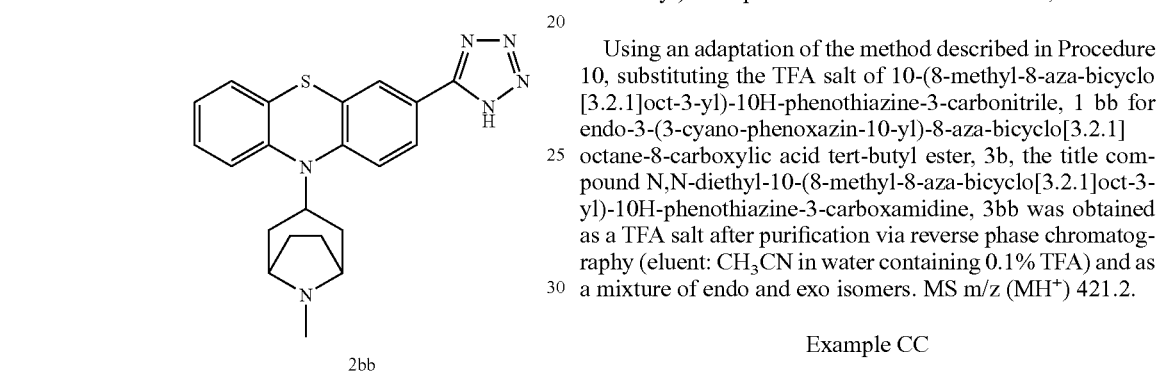

10-(8-Methyl-8-aza-bicyclo[3.2.1]oct-3-yl)-10H-phenothiazine-3-carbonitrile, 1bb Using an adaptation of the method described in Procedure 28, substituting 3-bromo-10-(8-methyl-8-aza-bicyclo[3.2.1]oct-3-yl)-10-H-phenothiazine, 3i for endo-3-(3-cyano-phenoxazin-10-yl)-8-aza-bicyclo[3.2.1]octane-8-carboxylic acid tert-butyl ester, 3b, the title compound 10-(8-methyl-8-aza-bicyclo[3.2.1]oct-3-yl)-10H-phenothiazine-3-carbonitrile, 1 bb was obtained as a TFA salt after purification via reverse phase chromatography (eluent: CH₃CN in water containing 0.1% TFA) and as a mixture of endo and exo isomers. MS m/z (MH⁺) 348.1.

10-(8-Methyl-8-aza-bicyclo[3.2.1]oct-3-yl)-3-(1H-tetrazol-5-yl)-10H-phenothiazine, 2bb Using an adaptation of the method described in Procedure 29, substituting the TFA salt of 10-(8-methyl-8-aza-bicyclo[3.2.1]oct-3-yl)-10H-phenothiazine-3-carbonitrile, 1 bb for 10-(8-phenethyl-8-aza-bicyclo[3.2.1]oct-3-yl)-10H-phenothiazine-3-carbonitrile, 2aa, the title compound 10-(8-methyl-8-aza-bicyclo[3.2.1]oct-3-yl)-3-(1H-tetrazol-5-yl)-10H-phenothiazine, 2bb was obtained as a TFA salt after purification via reverse phase chromatography (eluent: CH₃CN in water containing 0.1% TFA) and as a mixture of endo and exo isomers.

MS m/z (MH⁺) 391.1.

N,N-Diethyl-10-(8-methyl-8-aza-bicyclo[3.2.1]oct-3-yl)-10H-phenothiazine-3-carboxamidine, 3bb Using an adaptation of the method described in Procedure 10, substituting the TFA salt of 10-(8-methyl-8-aza-bicyclo[3.2.1]oct-3-yl)-10H-phenothiazine-3-carbonitrile, 1 bb for endo-3-(3-cyano-phenoxazin-10-yl)-8-aza-bicyclo[3.2.1]octane-8-carboxylic acid tert-butyl ester, 3b, the title compound N,N-diethyl-10-(8-methyl-8-aza-bicyclo[3.2.1]oct-3-yl)-10H-phenothiazine-3-carboxamidine, 3bb was obtained as a TFA salt after purification via reverse phase chromatography (eluent: CH₃CN in water containing 0.1% TFA) and as a mixture of endo and exo isomers. MS m/z (MH⁺) 421.2.

Example CC

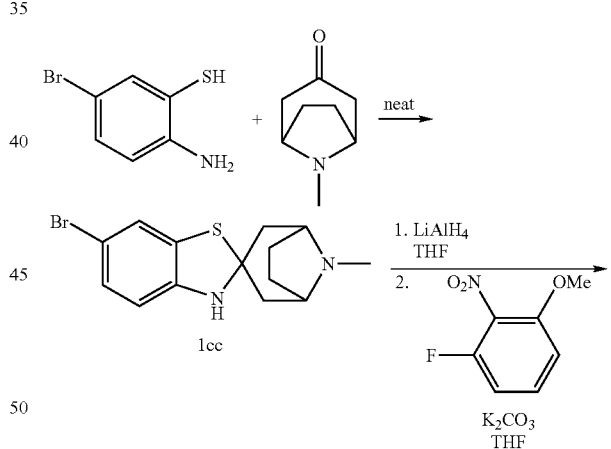

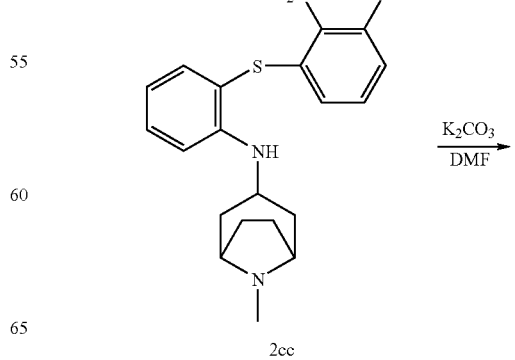

-continued

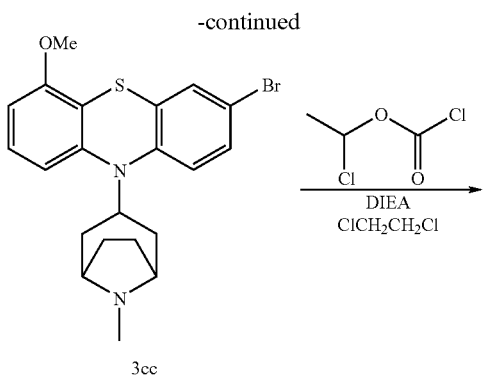

3cc

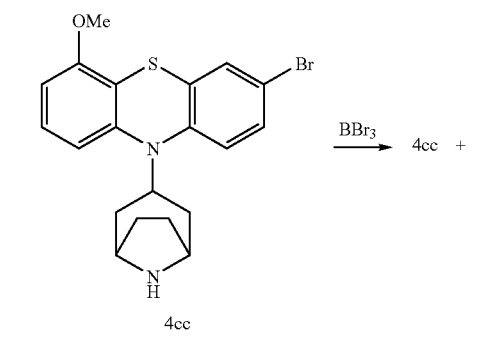

4cc

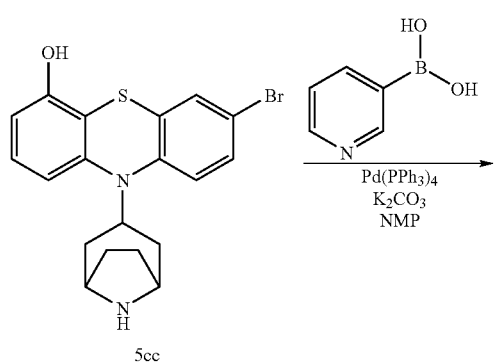

5cc

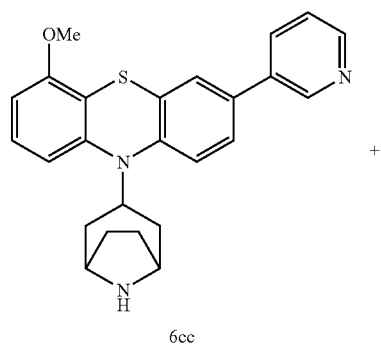

6cc

-continued

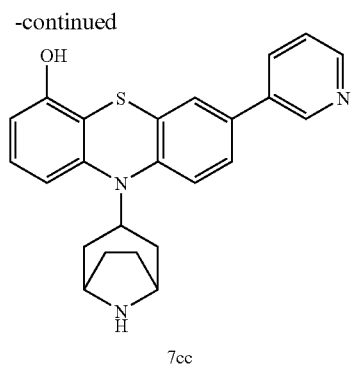

7cc

Spiro Compound, 1cc

Using an adaptation of the method described in Procedure 18, substituting for 2-amino-5-bromothiophenol for 2-aminothiophenol, the title compound 1cc was obtained.

[2-(3-Methoxy-2-nitro-phenylsulfanyl)-phenyl]-(8-methyl-8-aza-bicyclo[3.2.1]oct-3-yl)-amine, 2cc Using an adaptation of the method described in Procedure 19, substituting spiro compound, 1cc for spiro compound 11, the title compound [2-(3-methoxy-2-nitro-phenylsulfanyl)-phenyl]-(8-methyl-8-aza-bicyclo[3.2.1]oct-3-yl)-amine, 2cc was obtained a mixture of endo and exo isomers.

3-Bromo-6-methoxy-10-(8-methyl-8-aza-bicyclo[3.2.1]oct-3-yl)-10H-phenothiazine, 3cc Using an adaptation of the method described in Procedure 20, substituting [2-(3-methoxy-2-nitro-phenylsulfanyl)-phenyl]-(8-methyl-8-aza-bicyclo[3.2.1]oct-3-yl)-amine, 2cc for [2-(4-bromo-2-nitrophenylsulfanyl)-phenyl]-(8-methyl-8-aza-bicyclo[3.2.1]oct-3-yl)-amine, 21, the title compound 3-bromo-6-methoxy-10-(8-methyl-8-aza-bicyclo[3.2.1]oct-3-yl)-10H-phenothiazine, 3cc was obtained a mixture of endo and exo isomers.

10-(8-Aza-bicyclo[3.2.1]oct-3-yl)-3-bromo-6-methoxy-10H-phenothiazine, 4cc

Using an adaptation of the method described in Procedure 21, substituting 3-bromo-6-methoxy-10-(8-methyl-8-aza-bicyclo[3.2.1]oct-3-yl)-10H-phenothiazine, 3cc for 3-bromo-10-(8-methyl-8-aza-bicyclo[3.2.1]oct-3-yl)-10H-phenothiazine, 31, the title compound 10-(8-aza-bicyclo[3.2.1]oct-3-yl)-3-bromo-6-methoxy-10H-phenothiazine, 4cc was obtained a mixture of endo and exo isomers.

10-(8-Aza-bicyclo[3.2.1]oct-3-yl)-7-bromo-10H-phenothiazin-4-ol, 5cc

Using an adaptation of the method described in Procedure 16, substituting 10-(8-aza-bicyclo[3.2.1]oct-3-yl)-3-bromo-6-methoxy-10H-phenothiazine, 4cc for 6-methoxy-10-(8-phenethyl-8-aza-bicyclo[3.2.1]oct-3-yl)-10H-phenoxazine-3-carboxylic acid diethylamide, 6e, a mixture of title compound 10-(8-aza-bicyclo-[3.2.1]oct-3-yl)-7-bromo-10H-phenothiazin-4-ol, 5cc and starting material 10-(8-aza-bicyclo[3.2.1]oct-3-yl)-3-bromo-6-methoxy-10H-phenothiazine, 4cc was obtained a mixture of endo and exo isomers.

10-(8-Aza-bicyclo[3.2.1]oct-3-yl)-6-methoxy-3-pyridin-3-yl-10H-phenothiazine, 6cc and 10-(8-Aza-bicyclo[3.2.1]oct-3-yl)-7-pyridin-3-yl-10H-phenothiazin-4-ol, 7cc Using an adaptation of the method described in Procedure 23, substituting a mixture of 10-(8-aza-bicyclo[3.2.1]oct-3-yl)-3-bromo-6-methoxy-10H-phenothiazine, 4cc and 10-(8-aza-bicyclo-[3.2.1]oct-3-yl)-7-bromo-10H-phenothiazin-4-ol, 5cc for 3-bromo-10-(8-furan-3-ylmethyl-8-aza-bicyclo[3.2.1]oct-3-yl)-10H-phenothiazine, 51, a mixture of title compounds 10-(8-aza-bicyclo[3.2.1]oct-3-yl)-6-methoxy-3-pyridin-3-yl-10H-phenothiazine, 6cc and 10-(8-aza-bicyclo[3.2.1]oct-3-yl)-7-pyridin-3-yl-10H-phenothiazin-4-ol, 7cc was obtained. The compounds were separated via reverse phase HPLC (eluent: $CH_3CN$ in water containing 0.1% TFA) to yield 6cc [MS m/z (MH$^+$) 416.2] and 7cc [MS m/z (MH$^+$) 402.2], both as TFA salts and mixtures of endo and exo isomers.)

Example DD

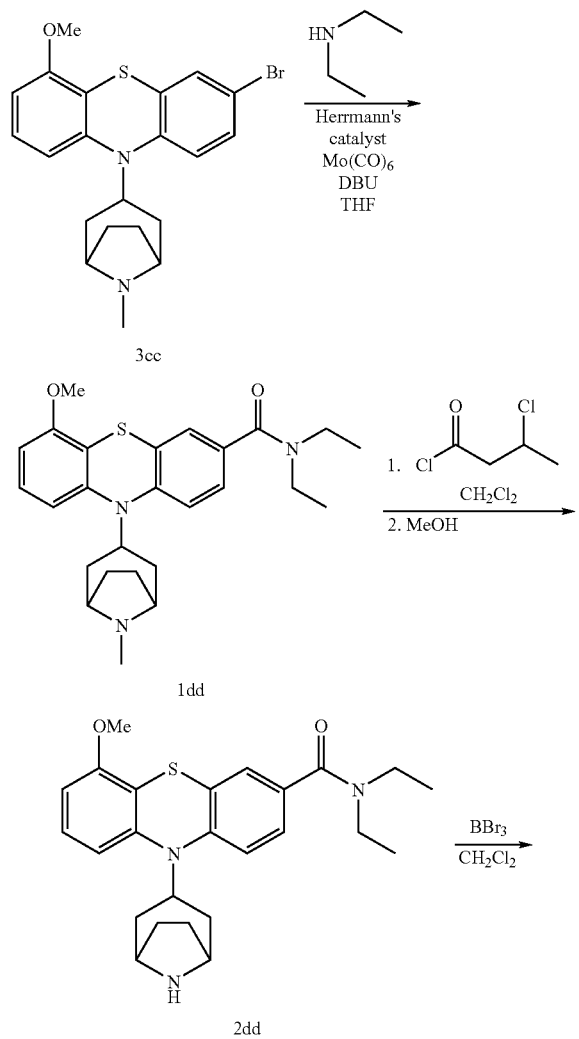

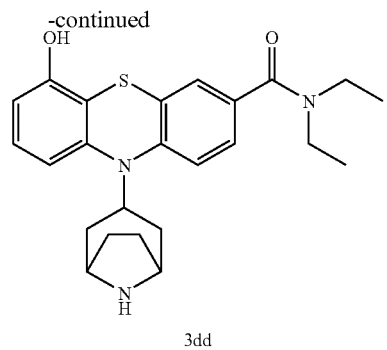

3dd

6-Methoxy-10-(8-methyl-8-aza-bicyclo[3.2.1]oct-3-yl)-10H-phenothiazine-3-carboxylic acid diethylamide, 1dd Using an adaptation of the method described in Procedure 26, substituting a mixture of endo and exo isomers of 3-bromo-6-methoxy-10-(8-methyl-8-aza-bicyclo[3.2.1]oct-3-yl)-10H-phenothiazine, 3cc for 3-bromo-10-piperidin-4-yl-10H-phenothiazine, 41, title compound 6-methoxy-10-(8-methyl-8-aza-bicyclo[3.2.1]oct-3-yl)-10H-phenothiazine-3-carboxylic acid diethylamide, 1dd was obtained as a mixture of endo and exo isomers.

10-(8-Aza-bicyclo[3.2.1]oct-3-yl)-6-methoxy-10H-phenothiazine-3-carboxylic acid diethylamide, 2dd Using an adaptation of the method described in Procedure 21, substituting 3-bromo-6-methoxy-10-(8-methyl-8-aza-bicyclo[3.2.1]oct-3-yl)-10H-phenothiazine, 3cc for 3-bromo-10-(8-methyl-8-aza-bicyclo[3.2.1]oct-3-yl)-10H-phenothiazine, 31, title compound 10-(8-aza-bicyclo[3.2.1]oct-3-yl)-6-methoxy-10H-phenothiazine-3-carboxylic acid diethylamide, 2dd was obtained as a TFA salt and as a mixture of endo and exo isomers.

10-(8-Aza-bicyclo[3.2.1]oct-3-yl)-6-hydroxy-10H-phenothiazine-3-carboxylic acid diethylamide, 3dd Using an adaptation of the method described in Procedure 16, substituting 10-(8-aza-bicyclo[3.2.1]oct-3-yl)-6-methoxy-10H-phenothiazine-3-carboxylic acid diethylamide, 2dd for 6-methoxy-10-(8-phenethyl-8-aza-bicyclo[3.2.1]oct-3-yl)-10H-phenoxazine-3-carboxylic acid diethylamide, 6e, a mixture of title compound 10-(8-aza-bicyclo[3.2.1]oct-3-yl)-6-hydroxy-10H-phenothiazine-3-carboxylic acid diethylamide, 3dd was obtained. MS m/z (MH$^+$) 424.2.

BIOLOGICAL EXAMPLES

Rat Brain Delta Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand ~4 nM [$^3$H]DPDPE or 0.15 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 µL of Betaplate Scint scintillation fluid (LKB) was added and the radioactivity quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program.

Rat Brain Mu Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 µL of Betaplate Scint scintillation fluid (LKB) was added and the radioactivity quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations tested). Percent inhibition was calculated as: [(total dpm-test compound dpm)/(total dpm-nonspecific dpm)]*100. Kd and Ki values were calculated using GraphPad PRISM data analysis program.

[$^{35}$S]GTPγS Binding Assay in NG108-15 Cell Membranes (Delta Opioid)

Methods: NG108-15 cell membranes can be purchased from Applied Cell Sciences (Rockville, Md.). 8 mg/mL of membrane protein suspended in 10 mM TRIS-HCl pH 7.2, 2 mM EDTA, 10% sucrose. Membranes can be maintained at 4-8° C. A 1 mL volume of membranes can be added into 10 mL cold binding assay buffer. The assay buffer contained 50 mM Tris, pH 7.6, 5 mM $MgCl_2$, 100 mM NaCl, 1 mM DTT and 1 mM EGTA. The membrane suspension can be homogenized twice with a Polytron, and centrifuged at 3000 rpm for 10 min. The supernatant can be then centrifuged at 18,000 rpm for 20 min. Ten mL assay buffer can be added into the pellet containing tube. The pellet and buffer can be mixed with a Polytron.

Incubation procedure: The pellet membranes (75 µg/mL) can be preincubated with SPA (10 mg/mL) at 25° C. for 45 min in the assay buffer. The SPA (5 mg/mL) coupled with membranes (37.5 µg/mL) can then be incubated with 0.1 nM [$^{35}$S] GTPγS in the same Tris buffer containing 100 µM GDP in total volume of 200 µL. Increasing concentrations of receptor agonists can be used to stimulate [$^{35}$S]-GTPγS binding. The basal binding can be tested in the absence of agonists and non-specific binding can be tested in the presence of 10 µM unlabeled GTPγS. The data can be analyzed on a Packard Top Count.

Data

% of Basal=(stimulated−non specific)*100/(basal−non specific).

$EC_{50}$ value values can be calculated using GraphPad Prism.

[$^{35}$S]GTPγS Binding Assays in CHO-hMOR Cell Membranes

Methods: CHO-hMOR cell membranes can be purchased from Receptor Biology, Inc. (Baltimore, Md.). About 10 mg/mL of membrane protein can be suspended in 10 mM TRIS-HCl pH 7.2, 2 mM EDTA, 10% sucrose, and the suspension kept on ice. A 1 mL volume of membranes can be added to 15 mL cold binding assay buffer containing 50 mM HEPES, pH 7.6, 5 mM $MgCl_2$, 100 mM NaCl, 1 mM DTT and 1 mM EDTA. The membrane suspension can be homogenized with a Polytron and centrifuged at 3,000 rpm for 10 min. The supernatant can then be centrifuged at 18,000 rpm for 20 min. The pellet can be resuspended in 10 mL assay buffer with a Polytron. The membranes can be preincubated with wheat germ agglutinin coated SPA beads (Amersham) at 25° C. for 45 min in the assay buffer. The SPA bead (5 mg/mL) coupled membranes (10 µg/mL) can be then incubated with 0.5 nM [$^{35}$S]GTPγS in the assay buffer. The basal binding can be that taking place in the absence of added test compound; this unmodulated binding can be considered as 100%, with agonist stimulated binding rising to levels significantly above this value. A range of concentrations of receptor agonist can be used to stimulate [$^{35}$S]GTPγS binding. Both basal and non-specific binding can be tested in the absence of agonist; non-specific binding determination included 10 µM unlabeled GTPγS.

Compounds can be tested for function as antagonists by evaluating their potential to inhibit agonist-stimulated GTPγS binding. Radioactivity can be quantified on a Packard TopCount. The following parameters can be calculated:

$$\% \text{ stimulation} = \frac{(\text{test compound } cpm - \text{non-specific } cpm)}{(\text{basal } cpm - \text{non-specific } cpm)} \times 100$$

$$\% \text{ inhibition} = \frac{\left(\frac{\% \text{ stimulation by 1 µM } DAMGO -}{\% \text{ stimulation by test compound}}\right)}{(\% \text{ stimulation by 1 µM } DAMGO - 100)} \times 100$$

EC$_{50}$ values can be calculated using GraphPad Prism.

| Biological Data | | |
|---|---|---|
| Compound Number | delta (Ki, nM) | mu (Ki, nM) |
| 4t | 0.1 | |
| 4aa | 0.1 | |
| 6b | 0.1 | 168.45 |
| 6d | 0.1 | 336 |
| 9t | 0.10 | |
| 8t | 0.18 | |
| 4v | 0.3 | |
| 2z | 0.62 | |
| 10t | 1.14 | |
| 7e | 2.2 | |
| 7t | 2.43 | |
| 7u | 3.27 | |
| 8v | 5.2 | |
| 3v | 8.3 | |
| 8j | 18.8 | |
| 8u | 20.70 | |
| 3t | 25.1 | |
| 3z | 27.63 | |
| 12v | 36.3 | |
| 6u | 44.49 | |
| 3c | 48.1 | 525 |
| 7v | 56.6 | |
| 5t | 56.7 | |
| 5x | 81.82 | |
| 2t | 86.6 | |
| 6e | 99.5 | |
| 7j | 103.6 | |
| 7i | 122.84 | 554.3 |
| 9v | 136.3 | |
| 4x | 161.3 | |
| 2u | 196.5 | |
| 6t | 231.0 | |
| 5k | 246.7 | |
| 6v | 263.2 | |
| 6i | 282.35 | 1055.7 |
| 4e | 320.9 | |
| 5aa | 321.1 | |
| 11i | 366.9 | 170.985 |
| 4a | 373 | 6761 |
| 3r | 396.8 | 682.2 |
| 11v | 399.5 | |
| 5b | 406 | 6849 |
| 5j | 409.4 | |
| 2x | 414.6 | |
| 4l | 424.6 | |
| 8i | 443.5 | 889.4 |
| 4k | 444.8 | |
| 5u | 477.80 | |
| 3m | 480.1 | |
| 12i | 491.45 | 1450 |
| 2c | 492 | 9448 |
| 5l | 539.2 | |
| 4u | 542.55 | |
| 13i | 551.6 | 3740 |
| 6a | 575 | 819 |
| 2h | 598 | 2889 |
| 17i | 629 | 1533.5 |
| 15i | 629.55 | 168.9 |
| 2m | 634.2 | |
| 9i | 649.35 | 538.4 |
| 1r | 651.95 | 2758 |
| 2k | 695.5 | |
| 2a | 697 | 5152 |
| 3l | 729.1 | |
| 2r | 863.65 | 4340 |
| 4p | 864.5 | |
| 4m | 868.9 | |
| 4i | 881 | 6613 |
| 1aa | 930.9 | |
| 18i | 940.75 | 8073 |
| 10i | 949.05 | 317.3 |
| 6l | 1269.1 | |
| 5m | 1278.5 | |

-continued

| Biological Data | | |
|---|---|---|
| Compound Number | delta (Ki, nM) | mu (Ki, nM) |
| 3u | 1356.30 | |
| 16i | 1453 | 2654 |
| 3x | 1585.0 | |
| 1y | 1601.8 | |
| 14i | 1603.5 | 598.75 |
| 3f | 1752 | 1435 |
| 8b | 1896 | >10000 |
| 1g | 2041 | 4285 |
| 5a | 2116 | 6091 |
| 5v | 2260.0 | |
| 3i | 2532 | 3185 |
| 7d | 2633 | 123 |
| 2f | 2644.5 | 2752 |
| 4c | 3106 | 89.0 |
| 6j | 3261.5 | |
| 3k | 3388.0 | |
| 3p | 5123.0 | |
| 19i | 5191 | 254 |
| 7b | 5475 | 288 |
| 7l | 6211.5 | |
| 9j | 11865.0 | |
| 10j | 13321.5 | |
| 6k | 14223.5 | |
| 10v | >10000 | |
| 13v | >10000 | |

The invention claimed is:
1. A compound of Formula (I):

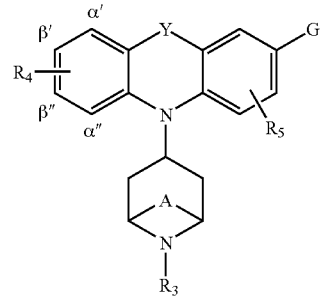

Formula (I)

wherein:
G is —C(Z)N(R$_1$)R$_2$, C$_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of C$_{1-8}$alkanyl, C$_{2-8}$alkenyl, C$_{2-8}$alkynyl, C$_{1-8}$alkanyloxy, hydroxy(C$_{1-8}$)alkanyl, carboxy(C$_{1-8}$)alkanyl, C$_{1-8}$alkanylcarbonylamino, halogen, hydroxy, cyano, nitro, oxo, thioxo, amino, C$_{1-6}$alkanylamino, di(C$_{1-6}$alkanyl)amino, C$_{1-8}$alkanylthio, C$_{1-8}$alkanylsulfonyl, C$_{1-8}$alkanylsulfonylamino, aminocarbonyl, aminothiocarbonyl, aminocarbonylamino, aminothiocarbonylamino, C$_{1-8}$alkanylaminocarbonyl, di(C$_{1-8}$alkanyl)aminocarbonyl, and C$_{1-6}$alkanyloxycarbonylamino;
R$_1$ is a substituent selected from the group consisting of hydrogen, C$_{1-8}$alkanyl, C$_{2-8}$alkenyl, and C$_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl;

wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl, and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$) alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein $C_{6-10}$aryl is optionally substituted with one to three substituents independently selected from the group consisting of $C_{1-6}$alkanyl, $C_{1-6}$alkoxy, halogen, and hydroxy; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl and fluoroalkanyloxy; or optionally; when $R_4$ is two substituents attached to adjacent carbon atoms, the two substituents together form a single fused moiety; wherein the fused moiety is —(CH$_2$)$_{3-5}$—, —O(CH$_2$)$_{2-4}$—, —(CH$_2$)$_{2-4}$O—, —O(CH$_2$)$_{1-3}$O—, or —S—C(NH$_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —(CH$_2$)$_m$—, wherein m is 2 or 3;

Y is S;

Z is O, S, NH, N($C_{1-6}$alkanyl), N(OH), N(O$C_{1-6}$alkanyl), or N(phenyl);

and enantiomers, diastereomers, tautomers, or pharmaceutically acceptable salts thereof.

2. The compound according to claim 1 wherein G is —C(Z)N(R$_1$)R$_2$, phenyl, or a heterocycle selected from the group consisting of tetrazolyl, oxadizolyl, furyl, quinolinyl, thienyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino.

3. The compound according to claim 1 wherein G is —C(Z)N(R$_1$)R$_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino.

4. The compound according to claim 1 wherein G is —C(Z)N(R$_1$)R$_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl.

5. The compound according to claim 1 wherein G is —C(Z)N(R$_1$)R$_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G are optionally substituted with one to three substituents independently selected from the group consisting of C$_{1-4}$alkanyl, C$_{1-4}$alkanyloxy, hydroxy(C$_{1-4}$)alkanyl, C$_{1-4}$alkanylcarbonylamino, hydroxy, cyano, oxo, thioxo, and aminocarbonyl.

6. The compound according to claim 1 wherein G is —C(Z)N(R$_1$)R$_2$, phenyl, or a heterocycle selected from the group consisting of tetrazolyl, oxadizolyl, furyl, quinolinyl, thienyl, and pyridinyl; wherein phenyl and the heterocycles of G are optionally substituted with one to three substituents independently selected from the group consisting of C$_{1-4}$alkanyl, C$_{1-4}$alkanyloxy, hydroxy(C$_{1-4}$)alkanyl, C$_{1-4}$alkanylcarbonylamino, hydroxy, cyano, oxo, thioxo, and aminocarbonyl.

7. The compound according to claim 1 wherein G is —C(Z)N(R$_1$)R$_2$, tetrazolyl, pyridinyl, oxadiazolyl optionally substituted with oxo, or phenyl optionally substituted with (C$_{1-8}$) alkanylcarbonylamino.

8. The compound according to claim 1 wherein G is —C(Z)N(R$_1$)R$_2$, 1H-tetrazol-4-yl, 4H-[1,2,4]-oxadiazol-5-oxo-3-yl, 2-methylcarbonylaminophenyl, pyridin-3-yl or pyridin-4-yl.

9. The compound according to claim 1 wherein R$_1$ is a substituent selected from the group consisting of hydrogen and C$_{1-4}$alkanyl.

10. The compound according to claim 1 wherein R$_1$ is selected from the group consisting of hydrogen, methyl, ethyl, and propyl.

11. The compound according to claim 1 wherein R$_1$ is selected from the group consisting of hydrogen, methyl, and ethyl.

12. The compound according to claim 1 wherein R$_2$ is selected from the group consisting of hydrogen; C$_{1-4}$alkanyl; phenyl; and C$_{1-6}$cycloalkanyl; wherein C$_{1-4}$alkanyl is optionally substituted with one to three substituents independently selected from the group consisting of phenyl, amino, C$_{1-6}$alkanylamino, di(C$_{1-6}$alkanyl)amino, C$_{1-4}$alkanyloxy, hydroxy, fluoro, chloro, cyano, aminocarbonyl, C$_{1-8}$alkanylaminocarbonyl, di(C$_{1-8}$alkanyl)aminocarbonyl, and phenoxy; and wherein any phenyl-containing substituents and C$_{1-6}$cycloalkanyl substituents of R$_2$ are optionally substituted with one to three substituents independently selected from the group consisting of C$_{1-8}$alkanyl, C$_{1-8}$alkanyloxy, trifluoromethyl, phenyl, fluoro, hydroxy, C$_{1-8}$alkanylthio, C$_{1-8}$alkanylsulfonyl, and C$_{1-8}$alkanylsulfonylamino; or R$_1$ and R$_2$ taken together with the nitrogen to which they are attached form a 5-7 membered cycloheteroalkyl optionally substituted with one to three substituents independently selected from the group consisting of C$_{1-4}$alkanyl, hydroxy(C$_{1-4}$)alkanyl, hydroxy, amino, C$_{1-6}$alkanylamino, di(C$_{1-6}$alkanyl)amino, and fluoro.

13. The compound according to claim 1 wherein R$_2$ is selected from the group consisting of hydrogen, C$_{1-4}$alkanyl, phenyl, and C$_{1-6}$cycloalkanyl; wherein C$_{1-4}$alkanyl is optionally substituted with one to three substituents independently selected from the group consisting of phenyl, C$_{1-4}$alkanyloxy, hydroxy, fluoro, aminocarbonyl, C$_{1-8}$alkanylaminocarbonyl, di(C$_{1-8}$alkanyl)aminocarbonyl, and phenoxy; and wherein any phenyl-containing substituent of R$_2$ is optionally substituted with one to three substituents independently selected from the group consisting of C$_{1-6}$alkanyl, C$_{1-6}$alkanyloxy, fluoro, hydroxy, and C$_{1-6}$alkanylthio; or R$_1$ and R$_2$ taken together with the nitrogen to which they are attached form a pyrrolidinyl or piperidinyl ring wherein said pyrrolidinyl or piperidinyl is optionally substituted with a substituent selected from the group consisting of C$_{1-4}$alkanyl and hydroxy.

14. The compound according to claim 1 wherein R$_2$ is selected from the group consisting of hydrogen, C$_{1-4}$alkanyl and phenyl; wherein C$_{1-4}$alkanyl is optionally substituted with one to three substituents independently selected from the group consisting of phenyl, C$_{1-4}$alkanyloxy, hydroxy, fluoro, and phenoxy; and wherein any phenyl-containing substituent of R$_2$ is optionally substituted with one to three substituents independently selected from the group consisting of C$_{1-6}$alkanyl, C$_{1-6}$alkanyloxy, fluoro, and hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from the group consisting of C$_{1-3}$alkanyl and hydroxy.

15. The compound according to claim 1 wherein R$_2$ is selected from the group consisting of hydrogen and C$_{1-4}$alkanyl; wherein C$_{1-4}$alkanyl is optionally substituted with phenyl; or R$_1$ and R$_2$ taken together with the nitrogen to which they are attached form a pyrrolidinyl wherein said pyrrolidinyl is optionally substituted with hydroxy.

16. The compound according to claim 1 wherein R$_2$ is selected from the group consisting of hydrogen, methyl, ethyl, and phenethyl; or R$_1$ and R$_2$ taken together with the nitrogen to which they are attached form pyrrolidin-1-yl, 3-hydroxypyrrolidin-1-yl or 3-(S)-hydroxypyrrolidin-1-yl.

17. The compound according to claim 1 wherein R$_3$ is selected from the group consisting of hydrogen, C$_{1-8}$alkanyl, C$_{2-8}$alkenyl, C$_{2-8}$alkynyl, C$_{1-8}$alkanyloxy(C$_{1-8}$)alkanyl, C$_{1-8}$alkanylthio(C$_{1-8}$)alkanyl, hydroxyC$_{1-8}$alkanyl, thioformyl, phenylimino(C$_{1-8}$)alkanyl, phenyl(C$_{1-8}$)alkanyl, and heteroaryl(C$_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of C$_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—.

18. The compound according to claim 1 wherein R$_3$ is selected from the group consisting of hydrogen, C$_{1-8}$alkanyl, C$_{2-8}$alkenyl, C$_{2-8}$alkynyl, C$_{1-8}$alkanyloxy(C$_{1-8}$)alkanyl, C$_{1-8}$alkanylthio(C$_{1-8}$)alkanyl, hydroxyC$_{1-8}$alkanyl, thioformyl, phenylimino(C$_{1-8}$)alkanyl, phenyl(C$_{1-8}$)alkanyl, and heteroaryl(C$_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, thiazolyl, isoquinolinyl, tetrazolyl; wherein phenyl and heteroaryl are optionally substituted with one to three substituents independently selected from the group consisting of C$_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—.

19. The compound according to claim 1 wherein R$_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group.

20. The compound according to claim 1 wherein $R_3$ is selected from the group consisting of hydrogen, methyl, methylbutenyl, propenyl, benzyl, phenethyl, and heteroaryl ($C_{1-8}$)alkanyl wherein the heteroaryl is selected from the group consisting of imidazolyl, furanyl, pyridinyl, thienyl, and thiazolyl.

21. The compound according to claim 1 wherein $R_3$ is selected from the group consisting of hydrogen, methyl, 3-methyl-2-butenyl, 2-propenyl, benzyl, 2-phenethyl, pyridin-2-ylmethyl, fur-3-ylmethyl, thiophene-2-ylmethyl, 1H-imidazol-2-ylmethyl, and thiazol-2-ylmethyl.

22. The compound according to claim 1 wherein $R_3$ is hydrogen, methyl, allyl, or heteroarylmethyl wherein heteroaryl is selected from the group consisting of benzo[1,3]dioxolyl, imidazolyl, furanyl, pyridinyl, and thienyl.

23. The compound according to claim 1 wherein $R_4$ is one to three substituents independently selected from the group consisting of hydrogen; $C_{1-6}$alkanyl; $C_{1-6}$alkanyloxy; $C_{6-10}$arylamino wherein $C_{6-10}$aryl is optionally substituted with one to three substituents independently selected from the group consisting of $C_{1-6}$alkanyl; $C_{1-6}$alkoxy, halogen, and hydroxy; formylamino; pyridinylamino; aminocarbonyl; $C_{1-6}$alkanylaminocarbonyl; $C_{1-6}$alkanylcarbonylamino; halogen; hydroxy; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; and thienyl.

24. The compound according to claim 1 wherein $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy.

25. The compound according to claim 1 wherein $R_4$ is one to two substituents independently selected from the group consisting of hydrogen, methyl, methoxy, bromo, fluoro, α'- or β'-phenyl, α'- or β'-pyridinyl, α'- or β'-furanyl, and hydroxy.

26. The compound according to claim 1 wherein $R_4$ is one to two substituents independently selected from the group consisting of hydrogen, methyl, phenyl, bromo, fluoro, methoxy, aminocarbonyl, chloro and hydroxy.

27. The compound according to claim 1 wherein $R_4$ is hydrogen, α'-methoxy, or α'-hydroxy.

28. The compound according to claim 1 wherein $R_4$ is hydrogen.

29. The compound according to claim 1 wherein $R_4$ is α'-hydroxy.

30. The compound according to claim 1 wherein $R_5$ is one to two substituents independently selected from the group consisting of hydrogen and halogen.

31. The compound according to claim 1 wherein $R_5$ is hydrogen.

32. The compound according to claim 1 wherein A is —$(CH_2)_{2-3}$—.

33. The compound according to claim 1 wherein A is —$(CH_2)_2$—.

34. The compound according to claim 1 wherein Z is O, NH, N($C_{1-6}$alkanyl), N(OH), N(O$C_{1-6}$alkanyl), or N(phenyl).

35. The compound according to claim 1 wherein Z is O, NH, or N(OH).

36. The compound according to claim 1 wherein Z is O or NH.

37. The compound according to claim 1 wherein
G is —C(Z)N($R_1$)$R_2$, phenyl, or a heterocycle selected from the group consisting of tetrazolyl, oxadizolyl, furyl, quinolinyl, thienyl, or pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;
$R_1$ is $C_{1-4}$ alkanyl, or hydrogen;
$R_2$ is hydrogen or $C_{1-4}$ alkanyl optionally substituted with phenyl;
or $R_1$ and $R_2$ taken together with the nitrogen to which they are attached form a pyrrolidinyl ring optionally substituted with hydroxy;
Z is NH or oxygen;
$R_3$ is pyridinyl($C_{1-8}$)alkanyl, furyl($C_{1-8}$)alkanyl, $C_{1-8}$ alkanyl, hydrogen, $C_{2-8}$ alkenyl, thienyl($C_{1-8}$)alkanyl, imidazolyl($C_{1-8}$)alkanyl, phenyl($C_{1-8}$)alkanyl, or thiazolyl ($C_{1-8}$)alkanyl;
$R_4$ is hydrogen, $C_{1-6}$ alkanyl, $C_{1-6}$ alkanyloxy, hydroxy, halogen, aminocarbonyl, or phenyl;
$R_5$ is hydrogen;
A is $CH_2CH_2$;
Z is O or NH; and
enantiomers, diastereomers, tautomers, and pharmaceutically acceptable salts thereof.

38. The compound according to claim 37 wherein G is —C(Z)N($R_1$)$R_2$; tetrazolyl; oxadiazolyl optionally substituted with oxo; furyl; quinolinyl; thienyl; phenyl optionally substituted with ($C_{1-8}$)alkanylcarbonylamino; or pyridinyl.

39. The compound according to claim 37 wherein when $R_1$ and $R_2$ taken together with the nitrogen to which they are attached form a pyrrolidinyl ring optionally substituted with hydroxy, Z is oxygen.

40. The compound according to claim 1 wherein:
G is —C(Z)N($R_1$)$R_2$; tetrazolyl; oxadiazolyl optionally substituted with oxo; phenyl optionally substituted with ($C_{1-8}$)alkanylcarbonylamino; or pyridinyl;
$R_1$ is $C_{1-4}$ alkanyl, or hydrogen;
$R_2$ is hydrogen or $C_{1-4}$ alkanyl optionally substituted with phenyl;
or $R_1$ and $R_2$ taken together with the nitrogen to which they are attached form a pyrrolidinyl ring optionally substituted with hydroxyl;
Z is NH or oxygen;
$R_3$ is pyridinyl($C_{1-8}$)alkanyl, furyl($C_{1-8}$)alkanyl, $C_{1-8}$ alkanyl, hydrogen, $C_{2-8}$ alkenyl, thienyl($C_{1-8}$)alkanyl, imidazolyl($C_{1-8}$)alkanyl, phenyl($C_{1-8}$)alkanyl, or thiazolyl ($C_{1-8}$)alkanyl;
$R_4$ is hydrogen, α'-hydroxy, or α'-methoxy;
$R_5$ is hydrogen;
A is $CH_2CH_2$;
Z is O or NH; and
enantiomers, diastereomers, tautomers, and pharmaceutically acceptable salts thereof.

41. The compound according to claim 1 wherein:

G is —C(Z)N(R$_1$)R$_2$, 1H-tetrazol-4-yl, 4H-[1,2,4]-oxadiazol-5-oxo-3-yl, 2-methylcarbonylaminophenyl, pyridin-3-yl or pyridin-4-yl, R$_1$ is hydrogen, ethyl, or methyl, R$_2$ is methyl, ethyl, phenethyl, or hydrogen;

or R$_1$ and R$_2$ taken together with the nitrogen to which they are attached form pyrrolidin-1-yl, 3-hydroxypyrrolidin-1-yl, or 3-(S)-hydroxypyrrolidin-1-yl;

Z is NH or oxygen,

R$_3$ is pyridin-2-ylmethyl, fur-3-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, benzyl, R$_4$ is hydrogen, α'-methoxy, or α'-hydroxy, R$_5$ is hydrogen A is CH$_2$CH$_2$;

Z is O or NH; and enantiomers, diastereomers, tautomers, and pharmaceutically acceptable salts thereof.

42. A compound of Formula (I):

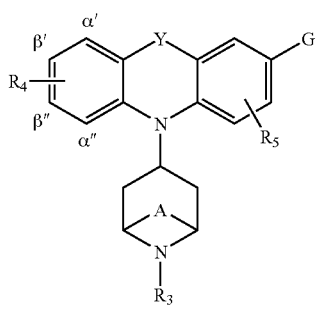

Formula (I)

wherein:

G is independently selected from —C(Z)N(R$_1$)R$_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of C$_{1-8}$alkanyl, C$_{1-8}$alkanyloxy, hydroxy(C$_{1-8}$)alkanyl, carboxy(C$_{1-8}$)alkanyl, C$_{1-8}$alkanylcarbonylamino, halogen, hydroxy, cyano, oxo, thioxo, amino, C$_{1-6}$alkanylamino, di(C$_{1-6}$alkanyl)amino, C$_{1-8}$alkanylthio, aminocarbonyl, aminothiocarbonyl, C$_{1-8}$alkanylaminocarbonyl, di(C$_{1-8}$alkanyl)aminocarbonyl, and C$_{1-6}$alkanyloxycarbonylamino; provided that when G is pyridin-3-yl or thien-3-yl and R$^3$ is hydrogen, R$^4$ is other than hydrogen;

R$^1$ is hydrogen or C$_{1-4}$alkanyl;

R$_2$ is selected from the group consisting of hydrogen; C$_{1-4}$alkanyl; phenyl; and C$_{1-6}$cycloalkanyl; wherein C$_{1-4}$alkanyl is optionally substituted with one to three substituents independently selected from the group consisting of phenyl, amino, C$_{1-6}$alkanylamino, di(C$_{1-6}$alkanyl)amino, C$_{1-4}$alkanyloxy, hydroxy, fluoro, chloro, cyano, aminocarbonyl, C$_{1-8}$alkanylaminocarbonyl, di(C$_{1-8}$alkanyl)aminocarbonyl, and phenoxy; and wherein any phenyl-containing substituent of R$_2$ and C$_{1-6}$cycloalkanyl substituents of R$_2$ are optionally substituted with one to three substituents independently selected from the group consisting of C$_{1-8}$alkanyl, C$_{1-8}$alkanyloxy, trifluoromethyl, phenyl, fluoro, hydroxy, C$_{1-8}$alkanylthio, C$_{1-8}$alkanylsulfonyl, and C$_{1-8}$alkanylsulfonylamino; or R$_1$ and R$_2$ taken together with the nitrogen to which they are attached form a 5-7 membered heterocycloalkyl wherein said heterocycloalkyl is optionally substituted with one to three substituents independently selected from the group consisting of C$_{1-8}$alkanyl, hydroxy(C$_{1-8}$)alkanyl, and hydroxy;

R$_3$ is selected from the group consisting of hydrogen, C$_{1-8}$alkanyl, C$_{2-8}$alkenyl, C$_{2-8}$alkynyl, C$_{1-8}$alkanyloxy(C$_{1-8}$)alkanyl, C$_{1-8}$alkanylthio(C$_{1-8}$)alkanyl, hydroxyC$_{1-8}$alkanyl, thioformyl, phenylimino(C$_{1-8}$)alkanyl, phenyl(C$_{1-8}$)alkanyl, and heteroaryl(C$_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of C$_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

R$_4$ is one to three substituents independently selected from the group consisting of hydrogen; C$_{1-6}$alkanyl; C$_{1-6}$alkanyloxy; C$_{6-10}$arylamino wherein C$_{6-10}$aryl is optionally substituted with one to three substitutents independently selected from the group consisting of C$_{1-6}$alkanyl; C$_{1-6}$alkoxy, halogen, and hydroxy; formylamino; pyridinylamino; aminocarbonyl; C$_{1-6}$alkanylaminocarbonyl; C$_{1-6}$alkanylcarbonylamino; halogen; hydroxy; C$_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; and thienyl;

R$_5$ is one to two substituents independently selected from the group consisting of hydrogen and halogen;

A is CH$_2$CH$_2$;

Y is S;

Z is O, NH, N(C$_{1-6}$alkanyl), N(OH), N(OC$_{1-6}$alkanyl), or N(phenyl); and enantiomers, diastereomers, tautomers, and pharmaceutically acceptable salts thereof.

43. A compound of Formula (I):

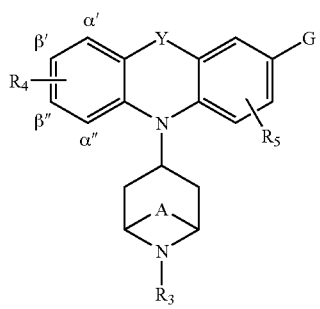

Formula (I)

wherein:
G is selected from —C(Z)N(R₁)R₂, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of C₁₋₄alkanyl, C₁₋₄alkanyloxy, hydroxy(C₁₋₄)alkanyl, carboxy(C₁₋₄)alkanyl, C₁₋₄alkanylcarbonylamino, hydroxy, cyano, oxo, thioxo, amino, C₁₋₆alkanylamino, di(C₁₋₆alkanyl)amino, C₁₋₈alkanylthio, aminocarbonyl, aminothiocarbonyl, C₁₋₈alkanylaminocarbonyl, and di(C₁₋₈alkanyl)aminocarbonyl;

R₁ is selected from the group consisting of hydrogen, methyl, ethyl, and propyl;

R₂ is selected from the group consisting of hydrogen, C₁₋₄alkanyl, phenyl, and C₁₋₆cycloalkanyl; wherein C₁₋₄alkanyl is optionally substituted with one to three substituents independently selected from the group consisting of phenyl, C₁₋₄alkanyloxy, hydroxy, fluoro, aminocarbonyl, C₁₋₈alkanylaminocarbonyl, di(C₁₋₈alkanyl)aminocarbonyl, and phenoxy; and wherein any phenyl-containing substituent of R₂ is optionally substituted with one to three substituents independently selected from the group consisting of C₁₋₆alkanyl, C₁₋₆alkanyloxy, fluoro, hydroxy, and C₁₋₆alkanylthio; or R₁ and R₂ taken together with the nitrogen to which they are attached form pyrrolidinyl or piperidinyl ring wherein said pyrrolidinyl or piperidinyl is optionally substituted with a substituent selected from the group consisting of C₁₋₃alkanyl and hydroxy;

R₃ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl(C₁₋₈)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group;

R₄ is one to two substituents independently selected from the group consisting of hydrogen, C₁₋₄alkanyl, C₁₋₄alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

R₅ is hydrogen;

A is CH₂CH₂;

Y is S;

Z is O, NH, or N(OH); and
enantiomers, diastereomers, tautomers, and pharmaceutically acceptable salts thereof.

44. The compound according to claim 43 wherein G is —C(Z)N(R₁)R₂, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G are optionally substituted with one to three substituents independently selected from the group consisting of C₁₋₄alkanyl, C₁₋₄alkanyloxy, hydroxy(C₁₋₄)alkanyl, C₁₋₄alkanylcarbonylamino, hydroxy, cyano, oxo, thioxo, and aminocarbonyl.

45. The compound according to claim 43 wherein G is —C(Z)N(R₁)R₂, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl.

46. The compound according to claim 43 wherein G is —C(Z)N(R₁)R₂, 1H-tetrazol-4-yl, 4H-[1,2,4]-oxadiazol-5-oxo-3-yl, 2-methylcarbonylaminophenyl, pyridin-3-yl or pyridin-4-yl.

47. The compound according to claim 43 wherein R₂ is selected from the group consisting of hydrogen, C₁₋₄alkanyl and phenyl; wherein C₁₋₄alkanyl is optionally substituted with one to three substituents independently selected from the group consisting of phenyl, C₁₋₄alkanyloxy, hydroxy, fluoro, and phenoxy; and wherein any phenyl-containing substituent is optionally substituted with one to three substituents independently selected from the group consisting of C₁₋₆alkanyl, C₁₋₆alkanyloxy, fluoro, and hydroxy; or R₁ and R₂ taken together with the nitrogen to which they are attached form a pyrrolidinyl or piperidinyl ring wherein said pyrrolidinyl or piperidinyl is optionally substituted with a substituent selected from C₁₋₃alkanyl or hydroxy; and R₃ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-yl methyl.

48. The compound according to claim 43 wherein R₁ is hydrogen, ethyl, or methyl; R₂ is methyl, ethyl, phenethyl, or hydrogen; or R₁ and R₂ taken together with the nitrogen to which they are attached form pyrrolidin-1-yl, 3-hydroxypyrrolidin-1-yl, or 3-(S)-hydroxypyrrolidin-1-yl.

49. A compound of Formula (I):

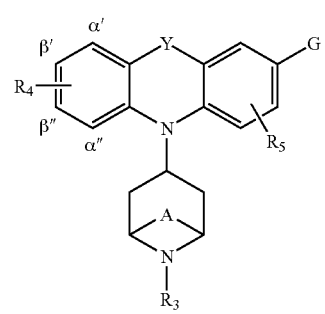

Formula (I)

wherein:
G is selected from —C(Z)N(R₁)R₂, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl;

R₁ is hydrogen, methyl, or ethyl;

R₂ is selected from the group consisting of hydrogen, C₁₋₄alkanyl and phenyl; wherein C₁₋₄alkanyl is optionally substituted with one to three substituents independently selected from the group consisting of phenyl, C₁₋₄alkanyloxy, hydroxy, fluoro, and phenoxy; and wherein any phenyl-containing substituent of R₂ is optionally substituted with one to three substituents independently selected from the group consisting of C$_{1-6}$alkanyl, C$_{1-6}$alkanyloxy, fluoro, and hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from C$_{1-3}$alkanyl or hydroxy;

R$_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl(C$_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group;

R$_4$ is one to three substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

R$_5$ is hydrogen;

A is CH$_2$CH$_2$;

Y is S;

Z is O or NH; and enantiomers, diastereomers, tautomers, and pharmaceutically acceptable salts thereof.

50. The compound according to claim 49 wherein R$_2$ is a substituent selected from the group consisting of hydrogen, C$_{1-4}$alkanyl and phenyl; wherein C$_{1-4}$alkanyl is optionally substituted with one to three substituents independently selected from the group consisting of phenyl, C$_{1-4}$alkanyloxy, hydroxy, and 2,6-dimethyl-phenoxy; and wherein any phenyl-containing substituent of R$_2$ is optionally substituted with one to three substituents independently selected from the group consisting of C$_{1-6}$alkanyl, C$_{1-6}$alkanyloxy, fluoro, and hydroxy; or R$_1$ and R$_2$ taken together with the nitrogen to which they are attached form a pyrrolidinyl or piperidinyl ring wherein said pyrrolidinyl or piperidinyl is optionally substituted with a substituent selected from C$_{1-3}$alkanyl or hydroxy.

51. The compound according to claim 49 wherein R$_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-ylmethyl; and R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy.

52. The compound according to claim 49 wherein R$_3$ is a substituent selected from the group consisting of benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl; R$_4$ is one to two substituents independently selected from the group consisting of hydrogen, methyl, methoxy, bromo, fluoro, α'- or β'-phenyl, α'- or β'-pyridinyl, α'- or β'-furanyl, and hydroxy.

53. The compound according to claim 49 wherein R$_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl; and R$_4$ is a substituent independently selected from the group consisting of hydrogen, methyl, methoxy, bromo, fluoro, α'- or β'-phenyl, α'- or β'-pyridinyl, α'- or β'-furanyl, and hydroxy.

54. A compound according to claim 1 that is:
N-{2-[10-(8-Allyl-8-aza-bicyclo[3.2.1]oct-3-yl)-10H-phenothiazine-3-yl]-phenyl}-acetamide;
N-{2-[10-(8-Phenethyl-8-aza-bicyclo[3.2.1]oct-3-yl)-10H-phenothiazin-3-yl]-phenyl}-acetamide;
N-(2-{10-[8-(1H-Imidazol-2-ylmethyl)-8-aza-bicyclo[3.2.1]oct-3-yl]-10H-phenothiazin-3-yl}-phenyl)-acetamide;
N-{2-[10-(8-Methyl-8-aza-bicyclo[3.2.1]oct-3-yl)-10H-phenothiazin-3-yl]-phenyl}-acetamide;
10-(8-Aza-bicyclo[3.2.1]oct-3-yl)-3-pyridin-3-yl-10H-phenothiazine;
N-{2-[10-(8-Aza-bicyclo[3.2.1]oct-3-yl)-10H-phenothiazin3-yl]-phenyl}-acetamide; or
10-(8-Allyl-8-aza-bicyclo[3.2.1]oct-3-yl)-3-pyridin-3-yl-10H-phenothiazine.

55. A compound according to claim 1 that is:
[10-(8-Furan-3-ylmethyl-8-aza-bicyclo[3.2.1]oct-3-yl)-10H-phenothiazin-3-yl]-pyrrolidin-1-yl-methanone;
[10-(8-Phenethyl-8-aza-bicyclo[3.2.1]oct-3-yl)-10H-phenothiazin-3-yl]-pyrrolidin-1-yl-methanone;
{10-[8-(3-Methyl-but-2-enyl)-8-aza-bicyclo[3.2.1]oct-3-yl]-10H-phenothiazin-3-yl}-pyrrolidin-1-yl-methanone;
[10-(8-Furan-3-ylmethyl-8-aza-bicyclo[3.2.1]oct-3-yl)-10H-phenothiazin-3-yl]-(3-hydroxy-pyrrolidin-1-yl)-methanone;
(3-Hydroxy-pyrrolidin-1-yl)-[10-(8-phenethyl-8-aza-bicyclo[3.2.1]oct-3-yl)-10H-phenothiazin-3-yl]-methanone;
{10-[8-(3-Methyl-but-2-enyl)-8-aza-bicyclo[3.2.1]oct-3-yl]-10H-phenothiazin-3-yl}-(3-methyl-pyrrolidin-1-yl)-methanone;
[10-(8-Methyl-8-aza-bicyclo[3.2.1]oct-3-yl)-10H-phenothiazin-3-yl]-pyrrolidin-1-yl-methanone;
(3-Hydroxy-pyrrolidin-1-yl)-[10-(8-methyl-8-aza-bicyclo[3.2.1]oct-3-yl)-10H-phenothiazin-3-yl]-methanone; or
10-(8-Methyl-8-aza-bicyclo[3.2.1]oct-3-yl)-10H-phenothiazine-3-carboxylic acid ethylamide.

56. A compound according to claim 1 that is:
10-(8-Phenethyl-8-aza-bicyclo[3.2.1]oct-3-yl)-3-(1H-tetrazol-5-yl)-10H-phenothiazine;
10-(8-Pyridin-2-ylmethyl-8-aza-bicyclo[3.2.1]oct-3-yl)-3-(1H-tetrazol-5-yl)-10H-phenothiazine;
10-(8-Aza-bicyclo[3.2.1]oct-3-yl)-3-(1H-tetrazol-5-yl)-10H-phenothiazine;
N,N-Diethyl-10-(8-phenethyl-8-aza-bicyclo[3.2.1]oct-3-yl)-10H-phenothiazine-3-carboxamidine;
N,N-Diethyl-10-(8-pyridin-2-ylmethyl-8-aza-bicyclo[3.2.1]oct-3-yl)-10H-phenothiazine-3-carboxamidine;
10-(8-Methyl-8-aza-bicyclo[3.2.1]oct-3-yl)-3-(1H-tetrazol-5-yl)-10H-phenothiazine;
N,N-Diethyl-10-(8-methyl-8-aza-bicyclo[3.2.1]oct-3-yl)-10H-phenothiazine-3-carboxamidine;
10-(8-Aza-bicyclo[3.2.1]oct-3-yl)-6-methoxy-3-pyridin-3-yl-10H-phenothiazine;
10-(8-Aza-bicyclo[3.2.1]oct-3-yl)-7-pyridin-3-yl-10H-phenothiazin-4-ol;

6-Methoxy-10-(8-methyl-8-aza-bicyclo[3.2.1]oct-3-yl)-10H-phenothiazine-3-carboxylic acid diethylamide;

10-(8-Aza-bicyclo[3.2.1]oct-3-yl)-6-methoxy-10H-phenothiazine-3-carboxylic acid diethylamide; or 10-(8-Aza-bicyclo[3.2.1]oct-3-yl)-6-hydroxy-10H-phenothiazine-3-carboxylic acid diethylamide.

57. A compound according to claim 1 that is:

10-(8-Pyridin-2-ylmethyl-8-aza-bicyclo[3.2.1]oct-3-yl)-3-(1H-tetrazol-5-yl)-10H-phenothiazine.

58. A composition comprising the dextrorotatory enantiomer of a compound according to claim 1 admixed with a pharmaceutically acceptable carrier, excipient or diluent, wherein said composition is substantially free from the levorotatory isomer of said compound.

59. A composition comprising the levororotatory enantiomer of a compound according to claim 1 admixed with a pharmaceutically acceptable carrier, excipient or diluent, herein said composition is substantially free from the dextrorotatory isomer of said compound.

60. A composition comprising the exo isomer of a compound according to claim 1 admixed with a pharmaceutically acceptable carrier, excipient or diluent, wherein said composition is substantially free from the endo isomer of said compound.

61. A composition comprising the endo isomer of a compound according to claim 1 admixed with a pharmaceutically acceptable carrier, excipient or diluent, wherein said composition is substantially free from the exo isomer of said compound.

62. A pharmaceutical composition comprising a compound or salt according to claim 1 admixed with a pharmaceutically acceptable carrier, excipient or diluent.

63. A veterinary composition comprising a compound or salt according to claim 1 admixed with a veterinarily acceptable carrier, excipient or diluent.

64. A pharmaceutical composition comprising a compound or salt according to claim 40 admixed with a pharmaceutically acceptable carrier, excipient or diluent.

65. A veterinary composition comprising a compound or salt according to claim 40 admixed with a veterinarily acceptable carrier, excipient or diluent.

66. A pharmaceutical composition comprising a compound or salt according to claim 41 admixed with a pharmaceutically acceptable carrier, excipient or diluent.

67. A veterinary composition comprising a compound or saslt according to claim 41 admixed with a veterinarily acceptable carrier, excipient or diluent.

68. A pharmaceutical composition comprising a compound or salt according to claim 42 admixed with a pharmaceutically acceptable carrier, excipient or diluent.

69. A veterinary composition comprising a compound or salt according to claim 42 admixed with a veterinarily acceptable carrier, excipient or diluent.

70. A pharmaceutical composition comprising a compound or salt according to claim 43 admixed with a pharmaceutically acceptable carrier, excipient or diluent.

71. A veterinary composition comprising a compound or salt according to claim 43 admixed with a veterinarily acceptable carrier, excipient or diluent.

72. A pharmaceutical composition comprising a compound or salt according to claim 49 admixed with a pharmaceutically acceptable carrier, excipient or diluent.

73. A veterinary composition comprising a compound or salt according to claim 49 admixed with a veterinarily acceptable carrier, excipient or diluent.

74. A pharmaceutical composition comprising a compound or salt according to claim 54 admixed with a pharmaceutically acceptable carrier, excipient or diluent.

75. A veterinary composition comprising a compound or salt according to claim 54 admixed with a veterinarily acceptable carrier, excipient or diluent.

76. A pharmaceutical composition comprising a compound or salt according to claim 55 admixed with a pharmaceutically acceptable carrier, excipient or diluent.

77. A veterinary composition comprising a compound or salt according to claim 55 admixed with a veterinarily acceptable carrier, excipient or diluent.

78. A pharmaceutical composition comprising a compound or salt according to claim 56 admixed with a pharmaceutically acceptable carrier, excipient or diluent.

79. A veterinary composition comprising a compound or salt according to claim 56 admixed with a veterinarily acceptable carrier, excipient or diluent.

80. A pharmaceutical composition comprising a compound or salt according to claim 57 admixed with a pharmaceutically acceptable carrier, excipient or diluent.

81. A veterinary composition comprising a compound or salt according to claim 57 admixed with a veterinarily acceptable carrier, excipient or diluent.

* * * * *